United States Patent
Radic et al.

(10) Patent No.: US 11,820,749 B2
(45) Date of Patent: Nov. 21, 2023

(54) CENTRALLY ACTIVE AND ORALLY BIOAVAILABLE UNCHARGED BISOXIME ANTIDOTES FOR ORGANOPHOSPHATE POISONING AND METHODS FOR MAKING AND USING THEM

(71) Applicants: The Regents of the University of California, Oakland, CA (US); Oak Ridge National Laboratory, Oak Ridge, TN (US)

(72) Inventors: Zoran Radic, San Diego, CA (US); Carlo Ballatore, La Jolla, CA (US); Lukas Gorecki, Hradec Kralovy (CZ); Palmer Taylor, La Jolla, CA (US); Andrey Kovalevsky, Oak Ridge, TN (US); Xiaolin Cheng, Oak Ridge, TN (US)

(73) Assignees: The Regents of the University of California, Oakland, CA (US); Oak Ridge National Laboratory, Oak Ridge, TN (US)

( * ) Notice: Subject to any disclaimer, the term of this patent is extended or adjusted under 35 U.S.C. 154(b) by 168 days.

(21) Appl. No.: 17/613,775

(22) PCT Filed: May 21, 2020

(86) PCT No.: PCT/US2020/034051
§ 371 (c)(1),
(2) Date: Nov. 23, 2021

(87) PCT Pub. No.: WO2020/237079
PCT Pub. Date: Nov. 26, 2020

(65) Prior Publication Data
US 2022/0227724 A1    Jul. 21, 2022

Related U.S. Application Data

(60) Provisional application No. 62/852,191, filed on May 23, 2019.

(51) Int. Cl.
C07D 295/13 (2006.01)
A61P 39/02 (2006.01)
C07D 211/56 (2006.01)

(52) U.S. Cl.
CPC .......... C07D 295/13 (2013.01); A61P 39/02 (2018.01); C07D 211/56 (2013.01)

(58) Field of Classification Search
CPC ...... C07D 295/13; C07D 211/56; A61P 39/02
See application file for complete search history.

(56) References Cited

U.S. PATENT DOCUMENTS

| | | |
|---|---|---|
| 6,251,949 B1 | 6/2001 | Masui et al. |
| 2013/0035351 A1 | 2/2013 | McHardy et al. |
| 2015/0361060 A1* | 12/2015 | Taylor ................. C07D 209/56 514/315 |

OTHER PUBLICATIONS

International Preliminary Report on Patentability for PCT/US2020/034051, dated Dec. 2, 2021.
Pubchem, Substance Record for SID 334202635. Available date: Apr. 25, 2017. [retrieved on Sep. 14, 2020]. Retrieved from the Internet: <https://pubchem.nr:hi.nlm nih.gov/substance/ 334202635>. entire document.

* cited by examiner

Primary Examiner — Timothy R Rozof
(74) Attorney, Agent, or Firm — Greer, Burns & Crain, LTD.; Gregory P. Einhorn

(57) ABSTRACT

In alternative embodiments, provided are uncharged bisoxime antidotes that cross the blood-brain barrier (BBB) to catalyze the hydrolysis of organophosphate (OP)-inhibited human acetylcholinesterase (hAChE) in the central nerve system (CNS). In alternative embodiments, provided are pumps, devices, subcutaneous infusion devices, continuous subcutaneous infusion devices, infusion pens, needles, reservoirs, ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector, comprising a compound as provided herein.

20 Claims, 52 Drawing Sheets

FIG. 33

| Rank | Structure | Comp. # | Docking score | | | | |
|---|---|---|---|---|---|---|---|
| | | | HON-NOH | -ON-NO- | HON-NO- | -ON-NOH | average |
| 1 | | 5 | 0.3 | -2.4 | -2.3 | -2.3 | -1.7 |
| 2 | | 7 | -1.1 | -1.4 | -1.9 | 3.7 | -0.2 |
| 3 | | 11 | -0.2 | 1.7 | 0.4 | 0.2 | 0.5 |
| 4 | | 16 | -1.9 | -2.2 | 3.6 | 3.2 | 0.7 |
| 5 | | 17 | 0.1 | -1.0 | -1.9 | 5.7 | 0.7 |
| 6 | | 3 | 1.7 | -0.2 | 4.0 | 0.2 | 1.4 |
| 7 | | 14 | 0.5 | 0.1 | 5.8 | 0.3 | 1.7 |
| 8 | | 10 | -0.0 | 6.2 | 1.3 | 0.3 | 1.9 |
| 9 | | 12 | 0.9 | 0.3 | 1.6 | 5.1 | 2.0 |
| 10 | | 6 | 0.1 | -1.4 | 4.6 | 4.6 | 2.0 |
| 11 | | 8 | 2.6 | 0.5 | 1.1 | 3.8 | 2.0 |
| 12 | | 1 | 5.4 | 3.8 | 0.9 | -1.0 | 2.3 |
| 13 | | 9 | 0.4 | 7.9 | 1.0 | 0.8 | 2.5 |
| 14 | | 15 | -0.3 | 4.8 | 0.2 | 6.4 | 2.8 |
| 15 | | 2 | -0.5 | -0.1 | 6.7 | 7.8 | 3.5 |
| 16 | | 4 | 2.9 | 0.0 | 6.6 | 7.1 | 4.2 |
| 17 | | 13 | 0.2 | 8.0 | 0.5 | 8.8 | 4.4 |

FIG. 34

| Oxime | | | pKa | | | logD$_{7.4}$ | logP$_{neut}$ | MW | TPSA | HBD | CNS MPO |
|---|---|---|---|---|---|---|---|---|---|---|---|
| | | Acid 1 | Acid 2 | Base 1 | Base 2 | | | | | | |
| | LG-703 | 8.80 | 9.43 | 4.51 | 7.96 | -1.44 | -0.77 | 328 | 130 | 4.5 | 4.0 |
| | LG-804 | 8.99 | 9.59 | 5.25 | 8.35 | -1.45 | -0.61 | 356 | 130 | 4.5 | 3.8 |
| | LG-700 | 8.72 | 9.23 | 2.87 | 7.16 | -0.55 | -0.34 | 314 | 130 | 4.0 | 4.0 |
| | LG-823 | 8.90 | 9.45 | - | 8.17 | -0.52 | -0.62 | 313 | 127 | 4.5 | 3.9 |
| | LG-750 | 8.72 | 9.39 | 3.17 | 7.42 | -1.42 | -1.10 | 328 | 130 | 4.4 | 4.0 |
| | LG-829 | 9.08 | 9.86 | - | 8.57 | -1.29 | -0.19 | 327 | 127 | 4.6 | 3.7 |
| | LG-747 | 8.77 | 9.42 | 3.69 | 7.67 | -1.16 | -0.70 | 342 | 130 | 4.4 | 4.0 |
| | RS194B | - | 9.66 | - | 8.56 | -0.54 | 0.58 | 213 | 65 | 2.7 | 4.9 |

FIG. 38

| Oxime | Paraoxon | | | Sarin | | | Cyclosarin | | | VX | | |
|---|---|---|---|---|---|---|---|---|---|---|---|---|
| | $k_2$ | $K_{ox}$ | $k_r$ | $k_2$ | $K_{ox}$ | $k_r$ | $k_2$ | $K_{ox}$ | $k_r$ | $k_2$ | $K_{ox}$ | $k_r$ |
| LG-703 | 0.14 | 2.0 | 69 | 0.80 | 0.90 | 890 | 0.50 | 2.9 | 170 | 1.3 | 1.2 | 1100 |
| LG-804 | 0.14 | 1.7 | 86 | 0.73 | 0.45 | 1700 | 0.57 | 4.5 | 130 | 1.1 | 0.63 | 1800 |
| LG-700 | 0.012 | 0.065 | 180 | 0.15 | 0.16 | 910 | 0.046 | 0.25 | 190 | 0.14 | 0.16 | 880 |
| LG-750 | 0.081 | 1.1 | 71 | 0.91 | 1.9 | 480 | 0.32 | 1.4 | 220 | 0.59 | 0.43 | 1400 |
| LG-747 | 0.053 | 0.45 | 120 | 0.33 | 0.25 | 1300 | 0.055 | 0.51 | 110 | 0.44 | 0.11 | 3900 |
| LG-823 | 0.10 | 1.4 | 72 | 0.55 | 0.35 | 1600 | 0.26 | 0.89 | 300 | 0.65 | 0.45 | 1500 |
| LG-829 | 0.17 | 1.9 | 87 | 0.78 | 0.37 | 2100 | >0.5 | >2.0 | 100 | 0.98 | 0.43 | 2300 |
| RS194B | 0.080 | 0.97 | 83 | 0.60 | 1.0 | 590 | 0.17 | 1.3 | 140 | 0.6 | 0.53 | 1100 |
| 2PAM | 0.27 | 1.8 | 150 | 1.1 | 0.34 | 3200 | 0.73 | 6.6 | 110 | 0.65 | 0.25 | 2600 |

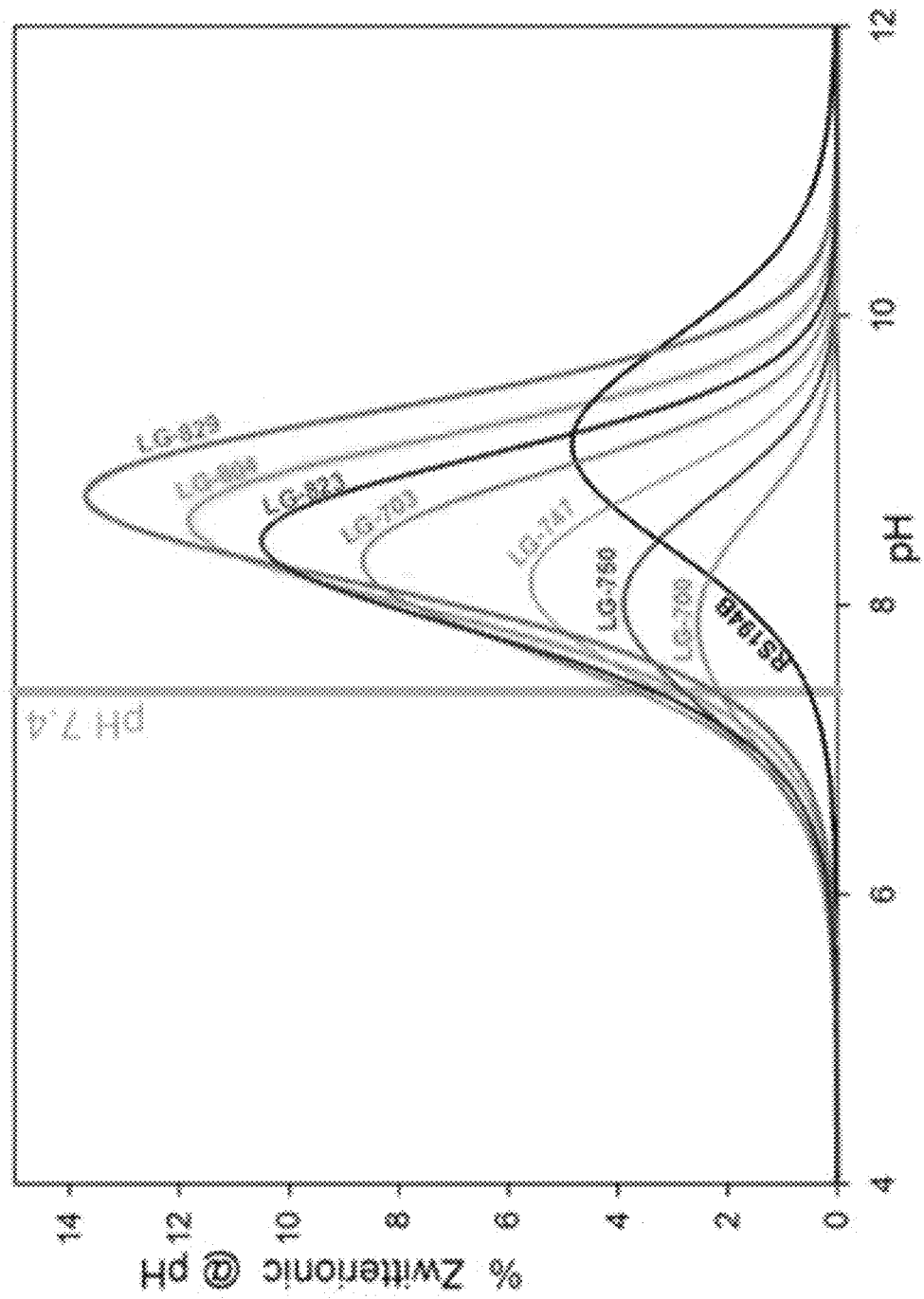

CENTRALLY ACTIVE AND ORALLY BIOAVAILABLE UNCHARGED BISOXIME ANTIDOTES FOR ORGANOPHOSPHATE POISONING AND METHODS FOR MAKING AND USING THEM

RELATED APPLICATIONS

This application is a national phase application claiming benefit of priority under 35 U.S.C. § 371 to Patent Convention Treaty (PCT) International Application serial number PCT/US2020/034051, filed May 21, 2020, which claims the benefit of priority to U.S. Provisional Application No. 62/852,191, filed May 23, 2019, now expired. The aforementioned applications are expressly incorporated herein by reference in their entirety and for all purposes.

STATEMENT AS TO FEDERALLY SPONSORED RESEARCH

This invention was made with government support under NS083451 and NS098998 awarded by the National Institutes of Health. The government has certain rights in the invention.

TECHNICAL FIELD

This invention generally relates to antidote chemistry for organophosphates and their detoxification. In alternative embodiments, provided are uncharged bis-oxime antidotes that cross the blood-brain barrier (BBB) to catalyze the hydrolysis of organophosphate (OP)-inhibited human acetylcholinesterase (hAChE) in the central nervous system (CNS).

BACKGROUND

Nucleophilic oxime reactivators of organophosphate (OP) inhibited acetylcholinesterase (AChE; EC 3.1.1.7) are the only reactivating antidotes against OP intoxication in nerve agent or OP pesticide exposure. Within the past decade it has become increasingly clear that for rapid and effective recovery from an OP intoxication antidote action is needed in both peripheral and in central tissue.

One of principles for ensuring that antidotes cross biological membranes and reach central nervous system is that they form an uncharged molecular species by fast equilibration. An acetamido oxime RS194B (see U.S. patent application publication no. US/2019/0119237 A1) is one of uncharged but ionizable antidotes with demonstrated capacity to cross blood-brain-barrier and biological membranes and effectively recover activity of OP inhibited hAChE, both in vitro and in vivo. Reactivation kinetics of RS194B, however, reveals relatively weak affinity for productive binding of this monoxime, as reflected in millimolar concentration ranges of the Kox constant. An improvement in affinity and reduction of the Kox constant could lead to enhanced antidotal efficacy of the compound at lower doses. A possible molecular basis for the large Kox value may come from sufficient reversible binding to the inactive OP-hAChE conjugate in a kinetically silent orientation with respect to reactivation reaction.

SUMMARY

In alternative embodiments, provided are compounds having one of the following structures or compositions having one or more compounds of the following structures, or equivalents thereof, or an isomer, optical isomer or a stereoisomer thereof, a racemate or racemic mixture thereof, an enantiomer, an individual diastereomer or a diastereomeric mixture thereof, or an analog thereof, or a crystalline product or crystalline intermediate thereof, or a pharmaceutically acceptable salt thereof, or prodrug thereof, or a bioisostere thereof; or a composition comprising an isolated, substantially isolated or purified compound consisting essentially of, or consisting of:

(a) a compound having the formula:

(i)

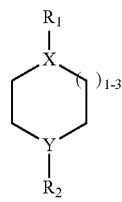

wherein X and Y are independently selected from C and N, and wherein $R_1$ and $R_2$ are independently selected from:

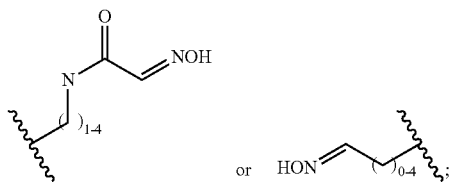

(ii)

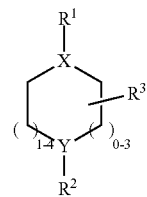

wherein X and Y are independently selected from C and N, wherein $R_1$ and $R_2$ are independently selected from:

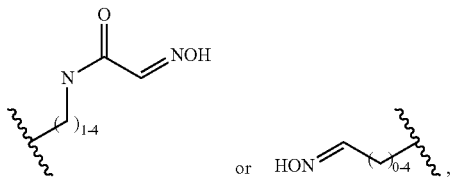

and $R_3$ is independent selected from:

an alkyl, an alkenyl, an alkynyl, an alkyloxy, an alkylamino, an alkylthio, a cycloalkyl, a heterocycloalkyl, a phenyl, a heteroaryl, an acyl, a sulfonyl, a lactam, a sultam, a cyano, a hydroxy and a halogen; or (iii)

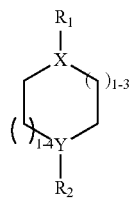

wherein X and Y are independently selected from C and N, and wherein $R_1$ and $R_2$ are independently selected from:

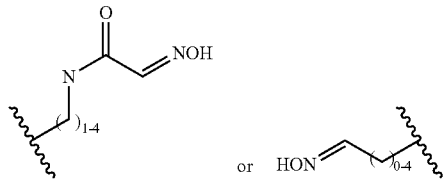

or
(b) a compound having the formula:

(i)

(LG-829)

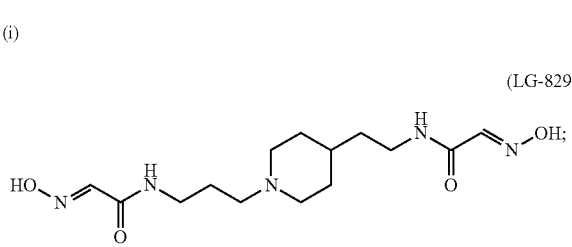

(ii) a compound having the formula:

(LG-823)

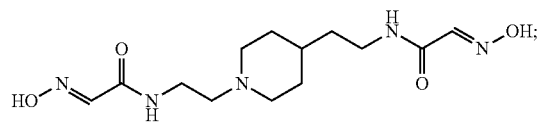

(iii) a compound having the formula:

(LG-804)

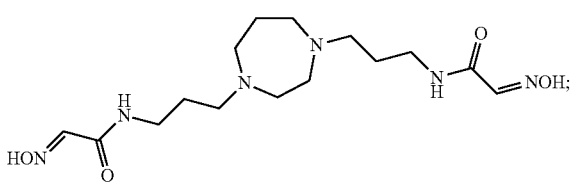

(iv) a compound having the formula:

(LG-703)

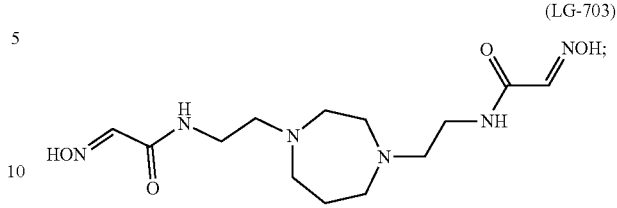

(v) a compound having the formula:

(LG-750)

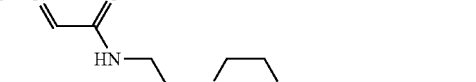

(vi) a compound having the formula: or (LG-747)

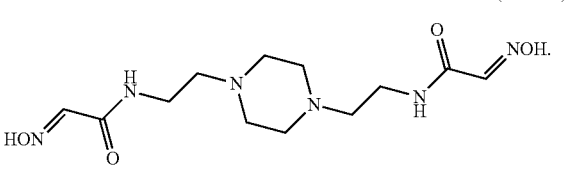

or
(vii) a compound having the formula:

(LG-700)

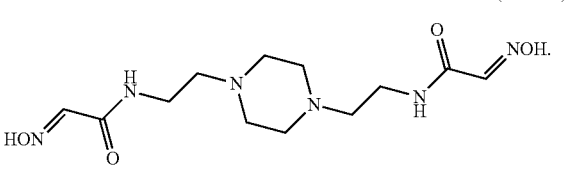

In alternative embodiments, provided are pharmaceutical compositions or formulations comprising a compound or composition as provided herein, wherein optionally the formulation is a solid, liquid, aerosol, mist, powder or emulsion formulation. In alternative embodiments, the formulations further comprise a pharmaceutically acceptable excipient, and optionally the pharmaceutically acceptable excipient comprises a sterile saline, a sterile buffer and/or a sterile water.

In alternative embodiments, provided are pharmaceutical compositions or formulations comprising a compound or composition as provided herein, wherein optionally the pharmaceutical composition is formulated for enteral or parenteral administration.

In alternative embodiments, pharmaceutical compositions or formulations as provided herein are formulated as or in or on: a liquid, a powder, an emulsion, a lyophilized powder, a spray, a cream, a lotion, a controlled release formulation, a tablet, a pill, a capsule, a gel, a geltab, a patch, an implants, an applicator stick, a solutions, a suspension, an ointment, a paste, a jelly, a paint, a powder, a mists an aerosol, an elixirs, a syrup, a liposome, a nanoliposome, a nanoparticle or a particle.

In alternative embodiments, provided are products of manufacture comprising: a compound as provided herein, or a formulation or pharmaceutical composition as provided herein, or a product of manufacture comprising and fabricated or manufactured to deliver to an individual in need thereof: a compound as provided herein, or a formulation or pharmaceutical composition as provided herein.

In alternative embodiments, the product of manufacture is fabricated or manufactured as a pump, a device, a subcutaneous infusion device, a continuous subcutaneous infusion device, an infusion pen, a needle, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector, comprising: a compound as provided herein, or a formulation or pharmaceutical composition as provided herein; or, fabricated to deliver to an individual in need thereof a compound as provided herein, or a formulation or pharmaceutical composition as provided herein.

In alternative embodiments, product of manufactures are fabricated or manufactured as a nebulizer or inhaler comprising: a compound as provided herein, or a formulation or pharmaceutical composition as provided herein; or, fabricated to deliver to an individual in need thereof a compound as provided herein, or a formulation or pharmaceutical composition as provided herein.

In alternative embodiments, provided are: a pump, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector, comprising a compound as provided herein, or a formulation as provided herein, or a pharmaceutical composition as provided herein.

In alternative embodiments, provided are methods for treating, ameliorating or protecting (preventing) an organophosphate toxicity or poisoning or toxic exposure, or for treating, ameliorating or protecting (preventing) organophosphate inhibition of an acetylcholinesterase (AChE), comprising:

administering to a patient or an individual in need thereof, a compound as provided herein, or a formulation as provided herein, or a pharmaceutical composition as provided herein, wherein optionally the compound or formulation is administered enterally or parenterally, wherein optionally the compound or formulation is administered orally, parenterally, by inhalation spray, nasally, topically, intrathecally, intrathecally, intracerebrally, epidurally, intracranially or rectally, or administering the compound as provided herein, or the formulation as provided herein, or the pharmaceutical composition as provided herein, using a pump, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector as provided herein.

In alternative embodiments of methods as provided herein, the organophosphate toxicity, poisoning or toxic exposure is caused by exposure of the patient or individual to an alkyl methylphosphonate or related nerve agent, a phosphoramidate (or amidophosphate), a phosphorodiamidate (or diamidophosphate), or an alkylphosphorate insecticide, and optionally the organophosphate (OP) is or is a component of a toxin, an herbicide, an insecticide, or a nerve gas or nerve agent, and optionally the organophosphate (OP) is or comprises a parathion, a malathion, a methyl parathion, a chlorpyrifos, a diazinon, a dichlorvos, a phosmet, a fenitrothion, a tetrachlorvinphos, an azamethiphos or an azinphos methyl, or the nerve agent is a soman (O-Pinacolyl methylphosphonofluoridate), a tabun (ethyl N,N dimethyl-phosphoramido-cyanidate) or a sarin ((RS)-propan-2-yl methylphosphonofluoridate).

In alternative embodiments of methods as provided herein, the acetylcholinesterase (AChE) is in the central nerve system (CNS), or the acetylcholinesterase (AChE) is a human acetylcholinesterase (hAChE).

In alternative embodiments, provided are methods for treating, preventing or ameliorating excessive acetylcholine stimulation in the brain, comprising:

administering to a patient or an individual in need thereof, a compound as provided herein, or a formulation as provided herein, or a pharmaceutical composition as provided herein, wherein optionally the compound or formulation is administered enterally or parenterally, wherein optionally the compound or formulation is administered orally, parenterally, by inhalation spray, nasally, topically, intrathecally, intrathecally, intracerebrally, epidurally, intracranially or rectally, or administering the compound as provided herein, or the formulation as provided herein, or a pharmaceutical composition as provided herein, using product of manufacture as provided herein, for example, using an inhaler, a nebulizer, a pump, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector as provided herein.

In alternative embodiments of methods as provided herein, the excessive acetylcholine stimulation in the brain, the CNS or the PNS is caused by a drug, a drug overdose, or a poisoning or a toxic exposure to a drug, and optionally the drug overdose causing the excessive acetylcholine stimulation is caused at least in part by (e.g., poisoning or exposure to): a carbamate (wherein optionally the carbamate is or comprises physostigmine or eserine (e.g., ANTILIRIUM™), neostigmine (e.g., BLOXIVERZ™, PROSTIGMIN™, or VAGOSTIGMIN™), pyridostigmine (e.g., MESTINON™), carbaryl, carbaril or 1-naphthyl methylcarbamate, e.g., SEVIN™)); or, an organophosphate agent such as a pesticide or poison (wherein optionally the organophosphate agent is or comprises diisopropyl-fluorophosphate (DFP) or isoflurophate, and/or echothiophate (e.g., PHOSPHOLINE IODIDE™ or PHOSPHOLINE™)

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

The drawings set forth herein are illustrative of exemplary embodiments provided herein and are not meant to limit the scope of the invention as encompassed by the claims.

FIG. 1A-D illustrate X-ray structures of RS194B in complex with (FIG. 1A showing image and FIG. 1C showing schematic) native hAChE and (FIG. 1B showing image and FIG. 1D showing schematic) VX-hAChE conjugate; stabilizing H-bonding is indicated by dashed lines in FIG. 1A and FIG. 1B, and are from the P3$_1$ complex; 2F$_O$-F$_C$ electron density maps (blue) contoured at 16 level are given for each of the complexes illustrated in FIG. 1C and FIG. 1D, as described in detail in Example 1, below.

FIG. 33 illustrates Table 2, showing the in silico design and evaluation of uncharged bis-oximes by computational docking into the VX-hAChE X-ray structure, as described in detail in Example 1, below.

FIG. 34 illustrates Table 3, acidity, lipophilicity and CNS MPO analyses of seven exemplary uncharged bis-oximes as provided herein, as described in detail in Example 1, below.

Figure 35A:
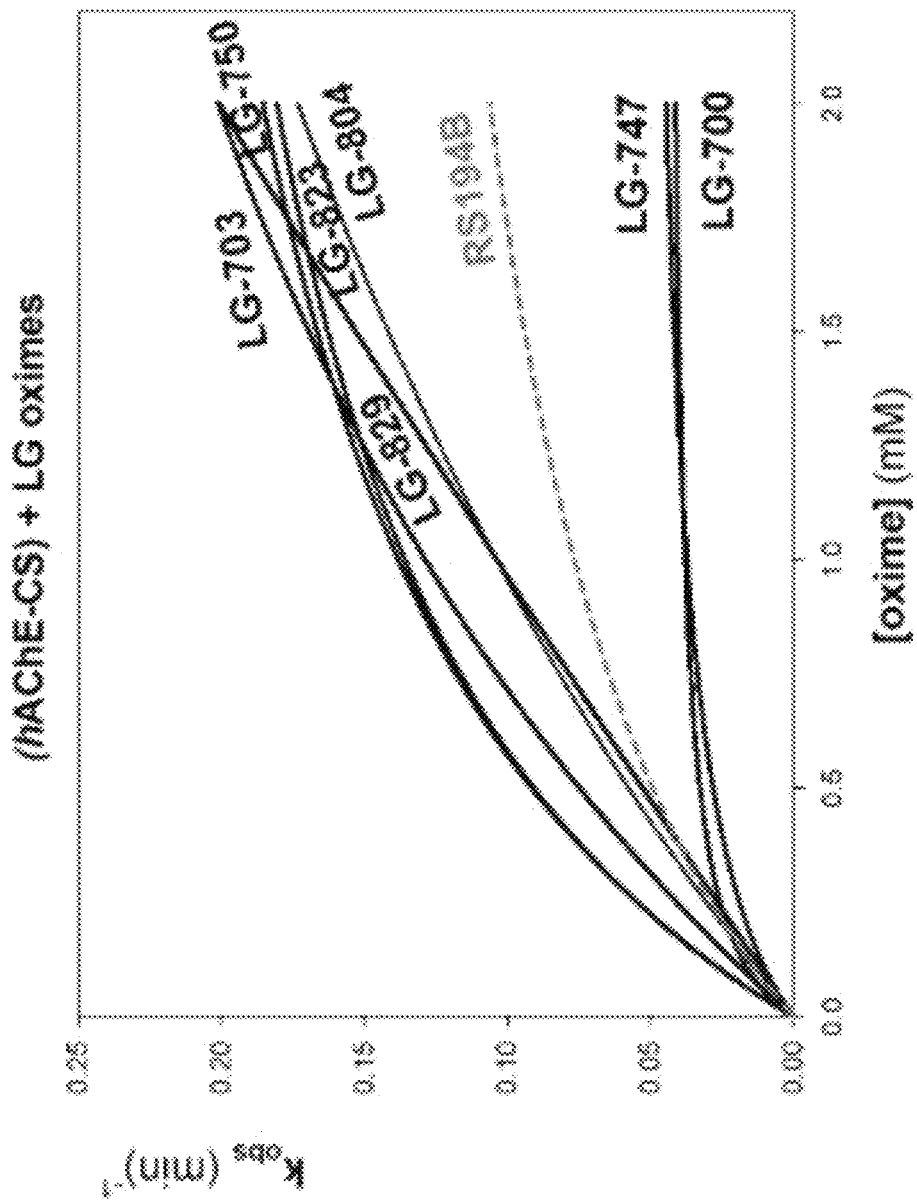
Figure 35B:
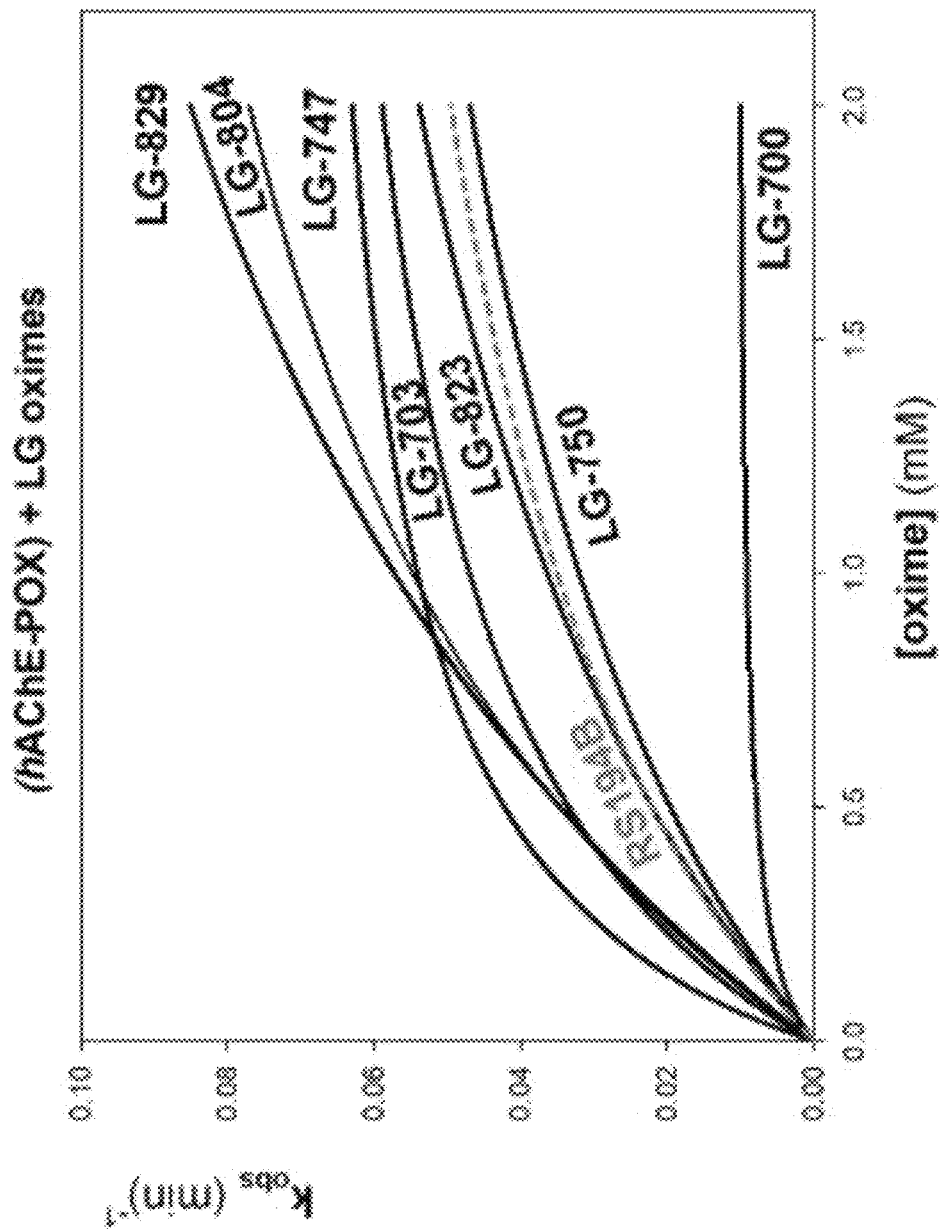
Figure 35C:
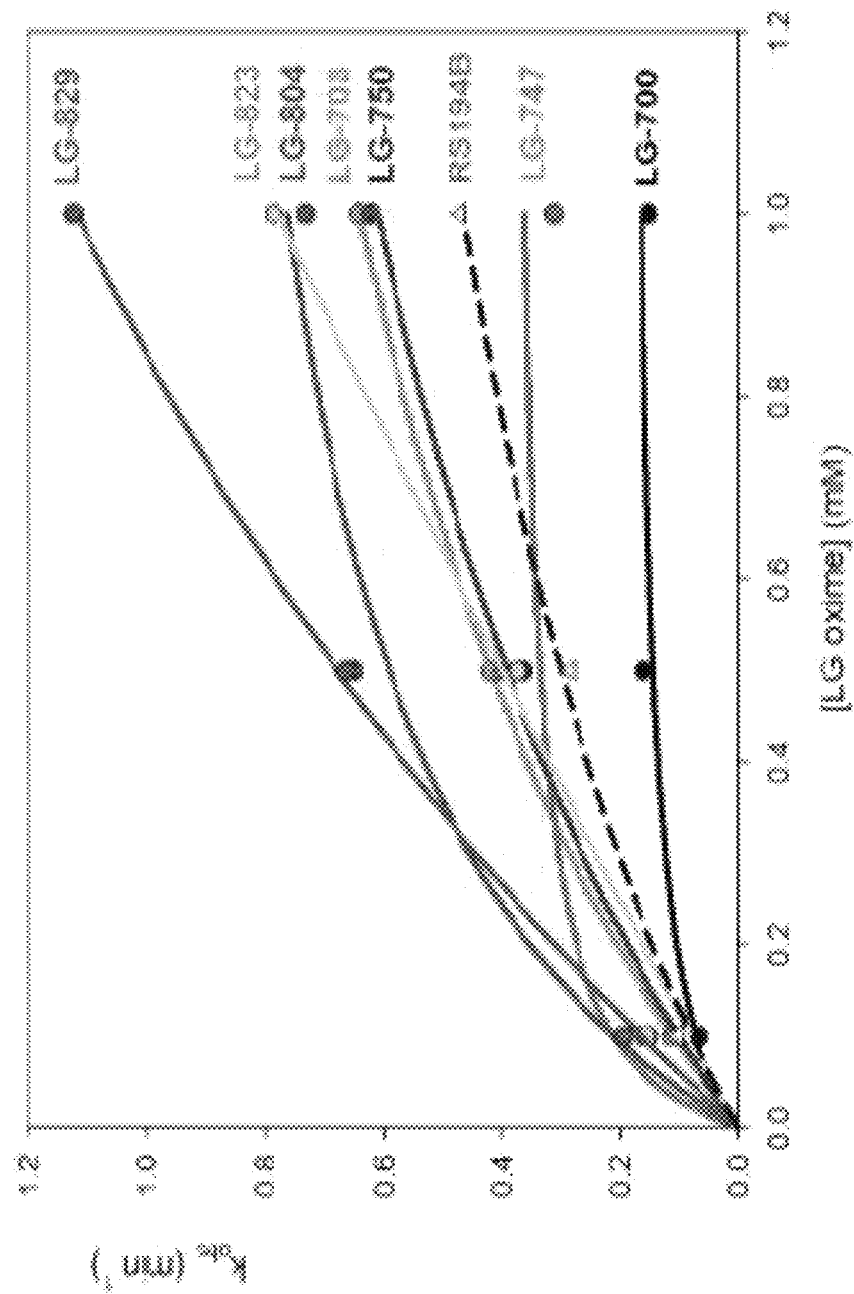
Figure 35D:
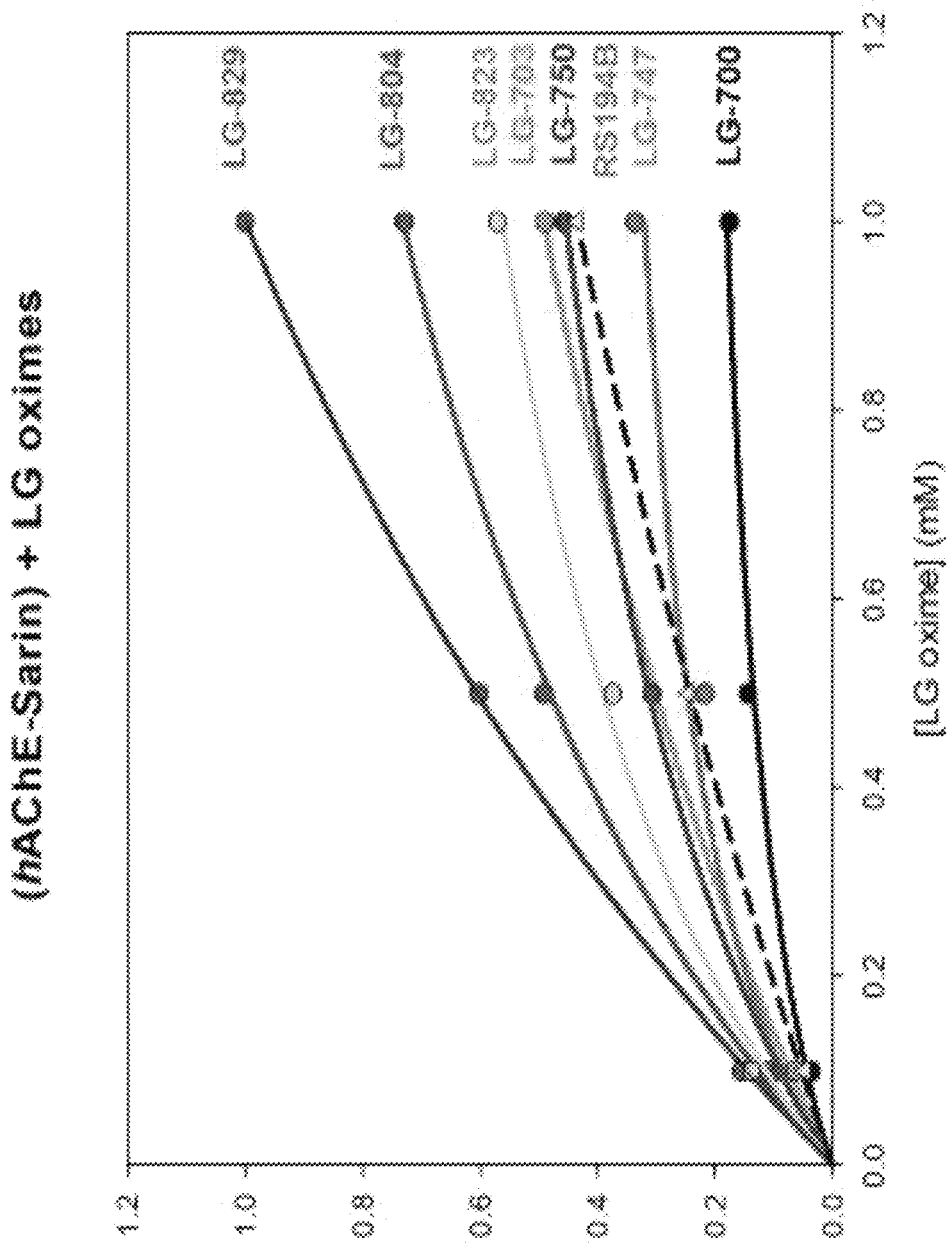

FIG. 35A-D graphically illustrate data showing in vitro reactivation kinetics of four OP-hAChE conjugates (FIG. 35A, hAChE-CS+LG oximes; FIG. 35B, hAChE-PDX+LG oximes; FIG. 35C, hAChE-VX+LG oximes; FIG. 35A, hAChE-sarin+LG oximes) by seven exemplary uncharged LG bisoximes compared to the monoxime RS194B (dashed curves), as described in detail in Example 1, below.

Figure 36A:
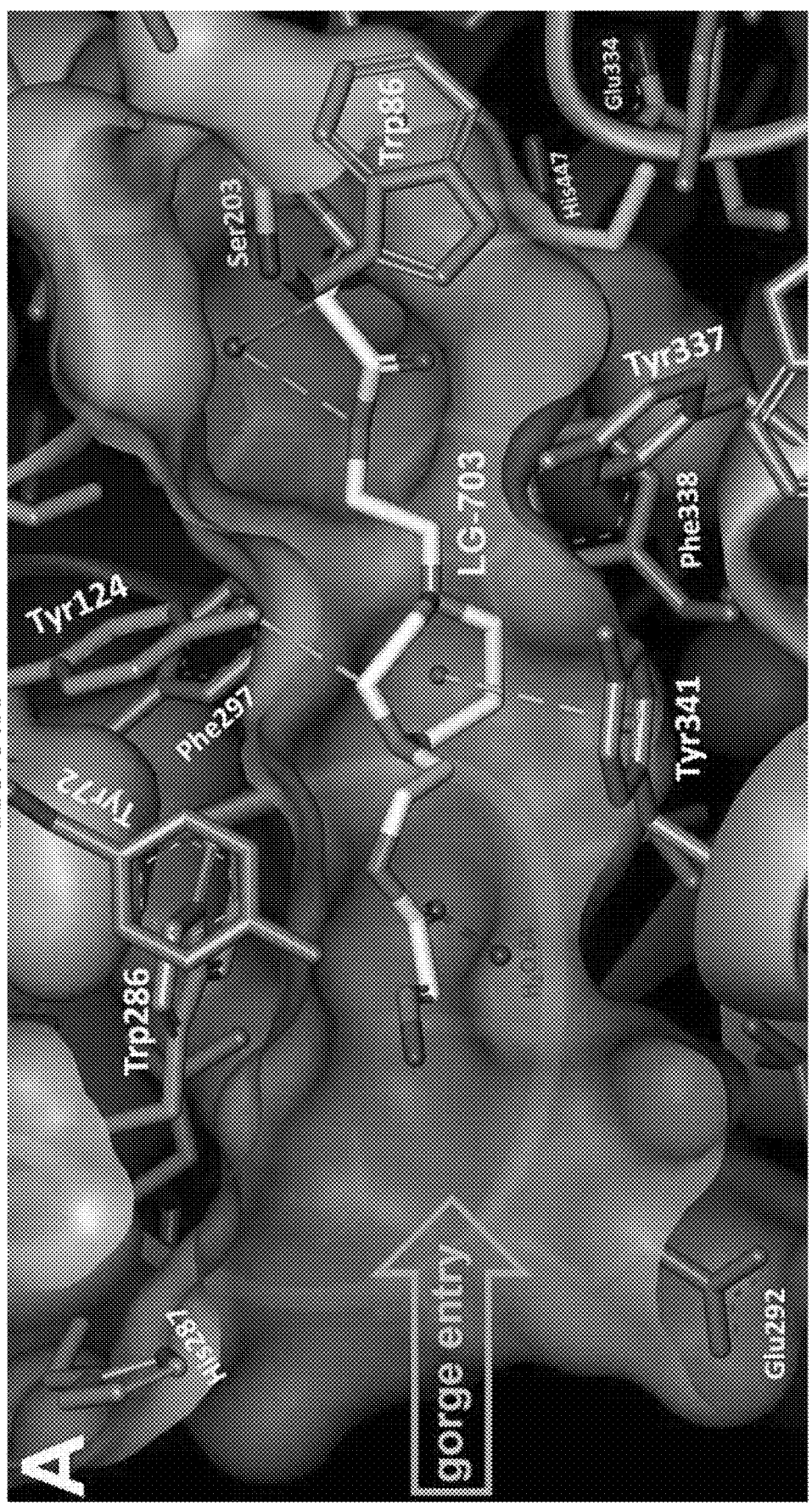
Figure 36B:
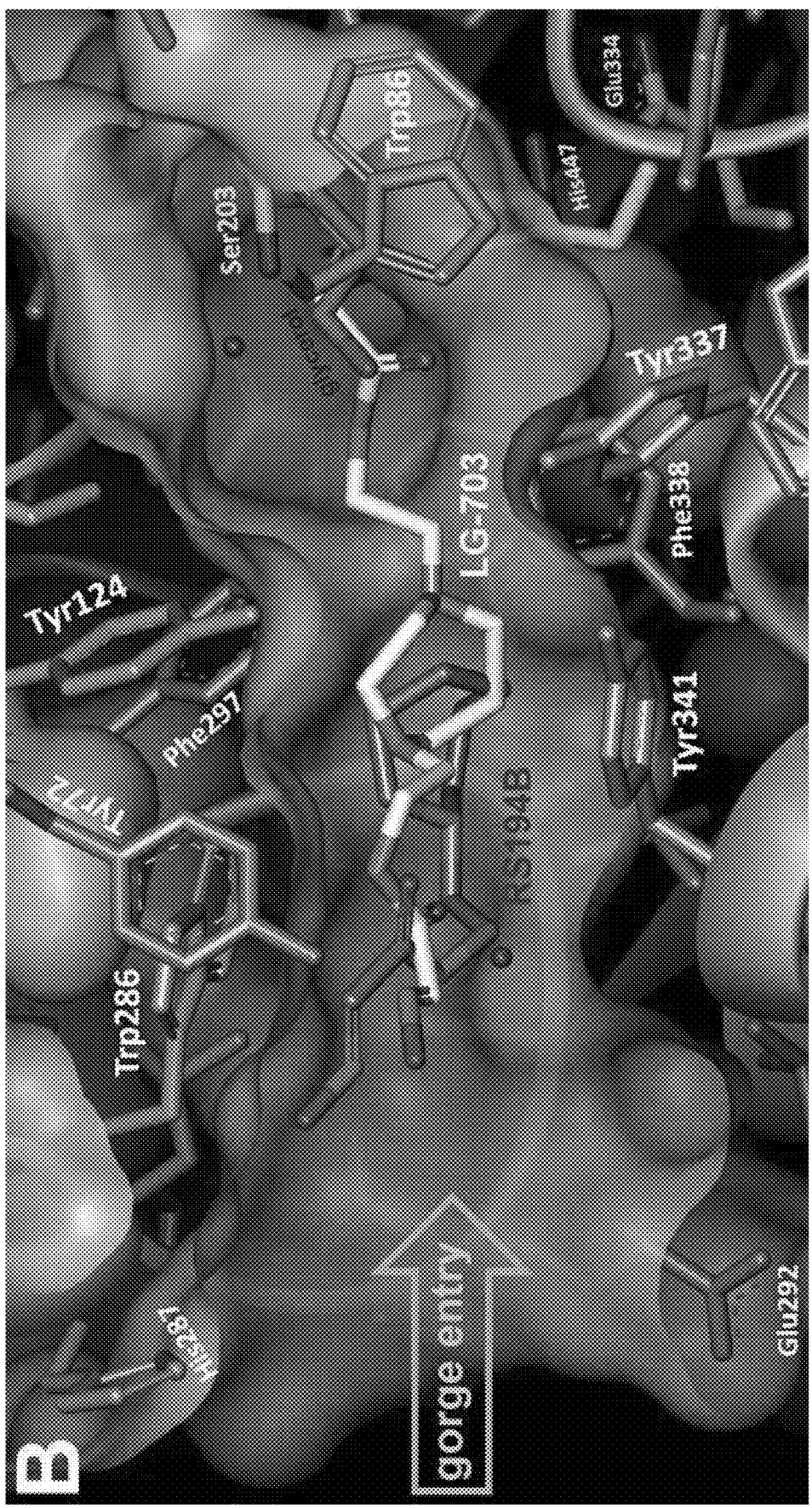
Figure 36C:
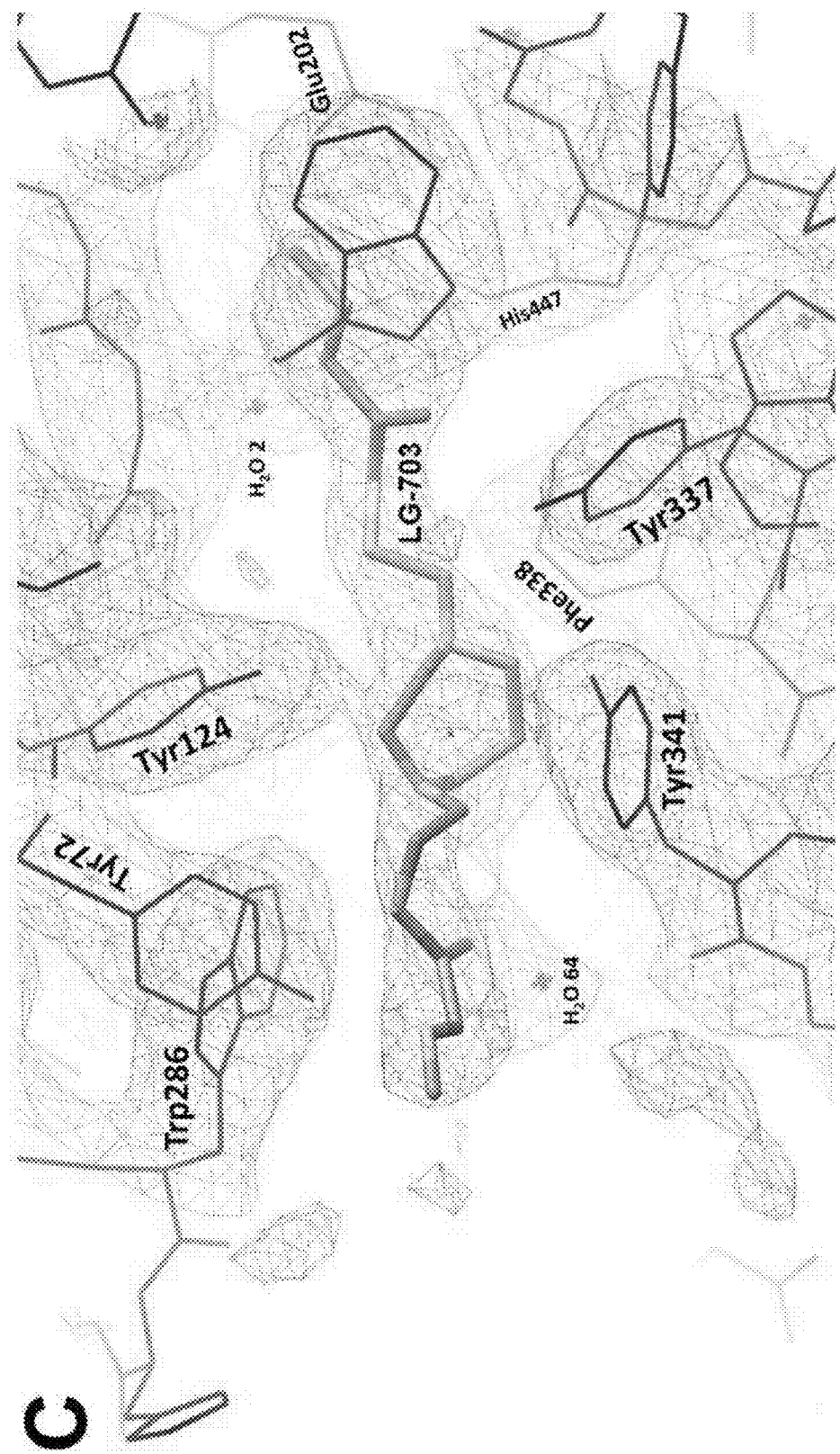

FIG. 36A-C schematically illustrate an x-ray structure of one of the exemplary LG compounds as provided herein (exemplary compound LG-703) as it fits into the acetylcholinesterase (hAChE) enzyme gorge entry, showing that it directs one of its two reactive O groups in direction where the organophosphate (OP) VX binds: FIG. 36A shows exemplary compound LG-703 in the enzyme active site gorge; FIG. 36B shows exemplary compound LG-703 with compound RS194B in the enzyme active site gorge; and FIG. 36C is a schematic of FIG. 36A, as described in detail in Example 1, below.

Figure 37A:
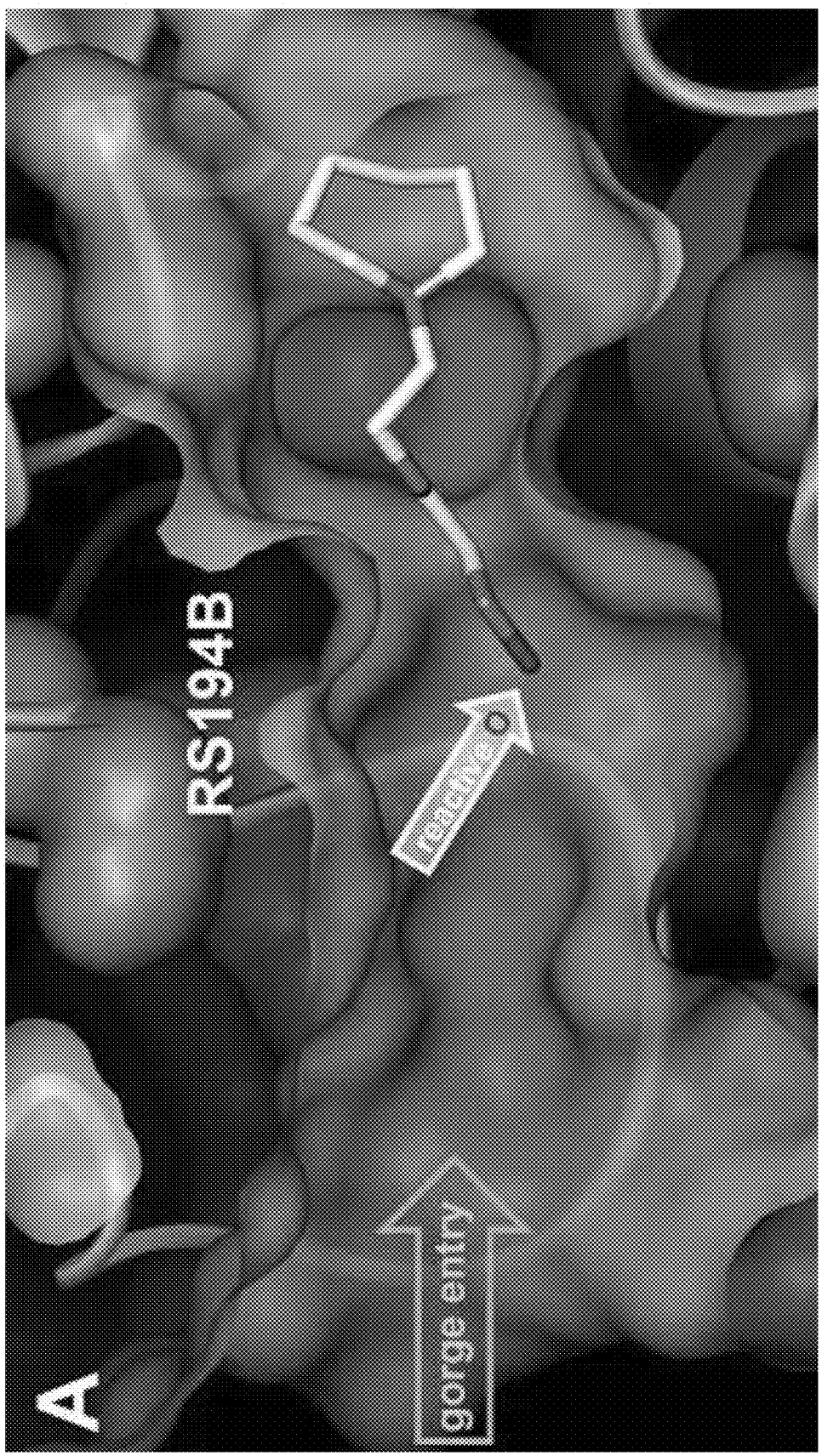
Figure 37B:
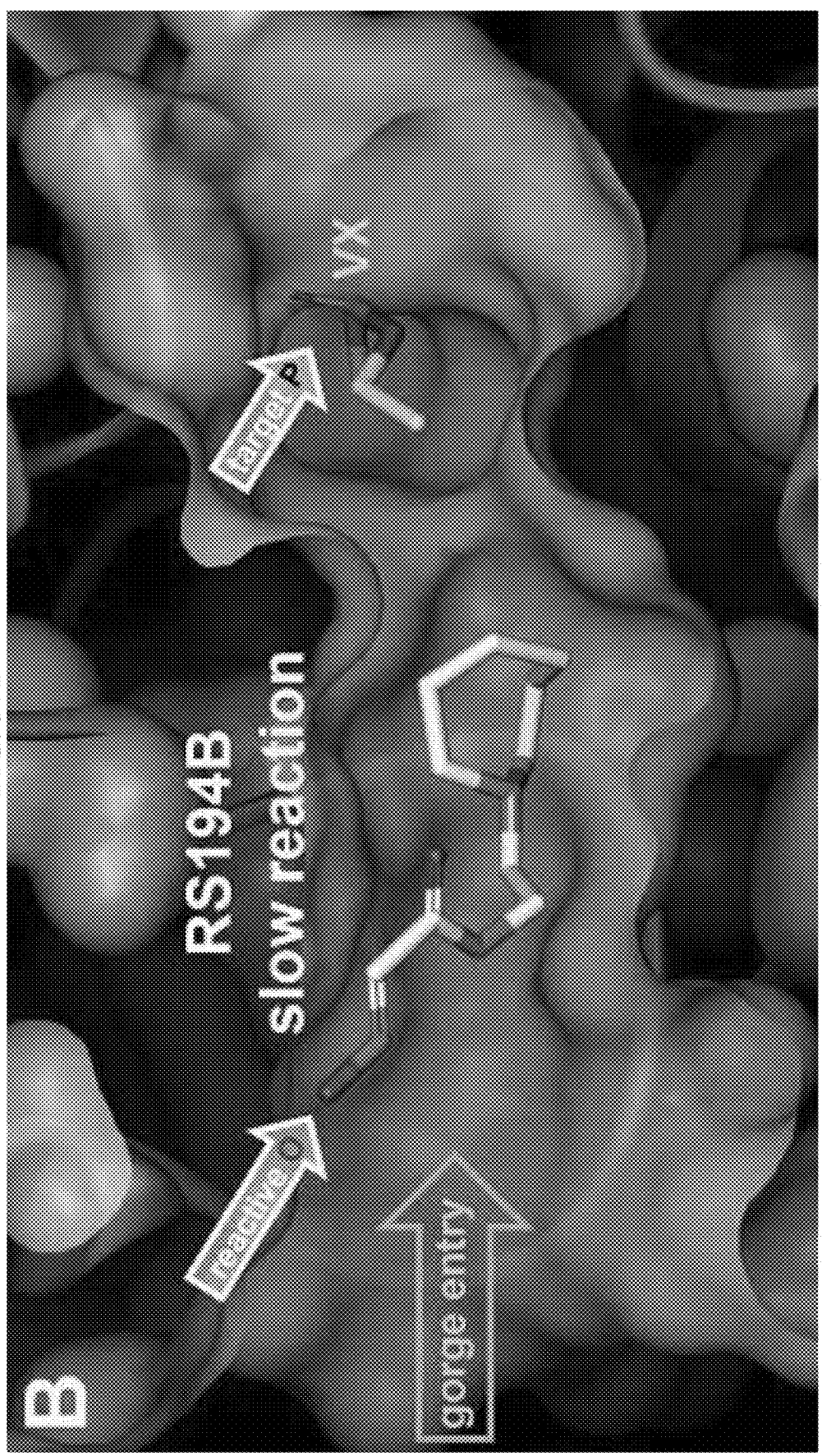
Figure 37C:
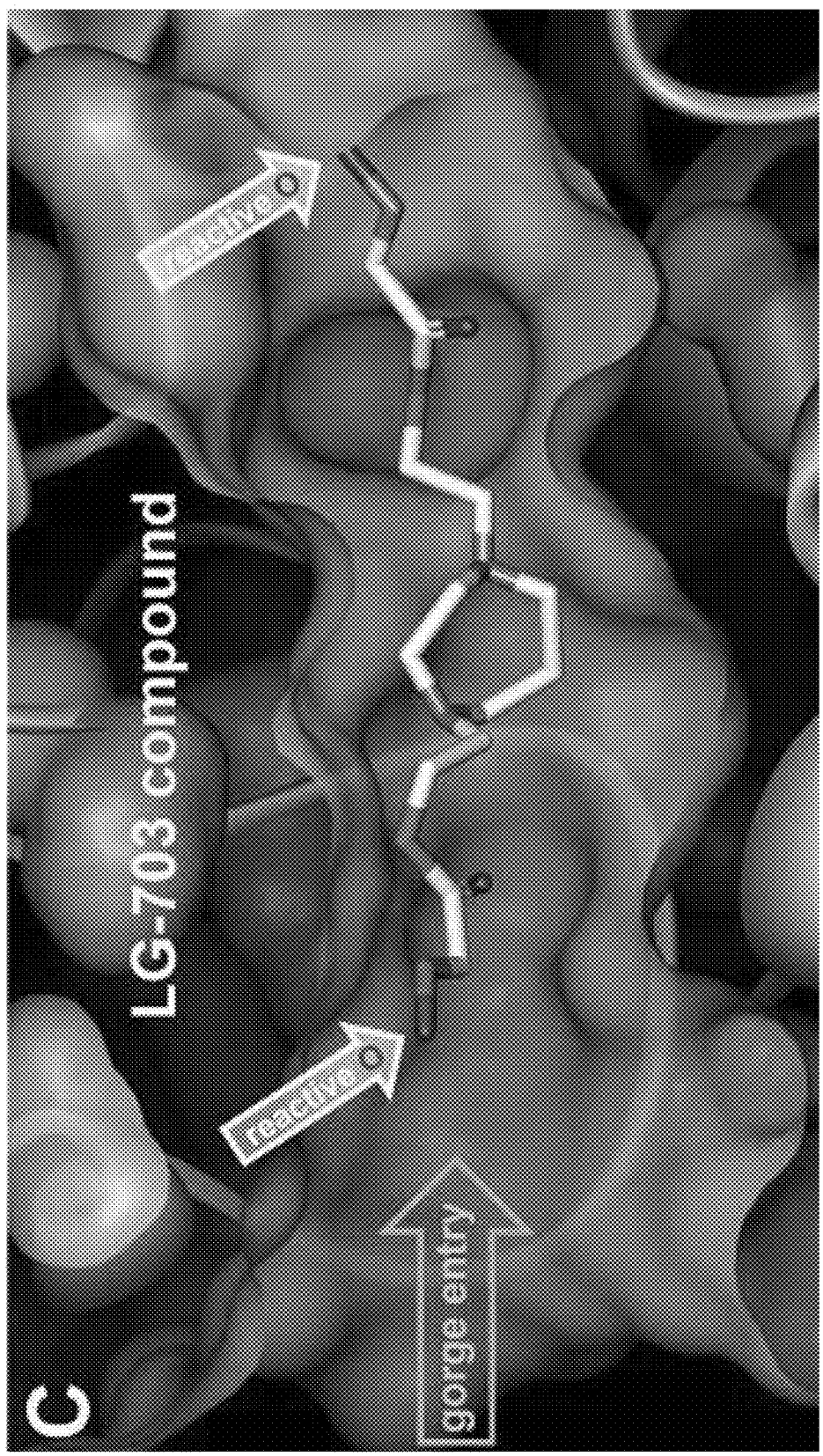
Figure 37D:
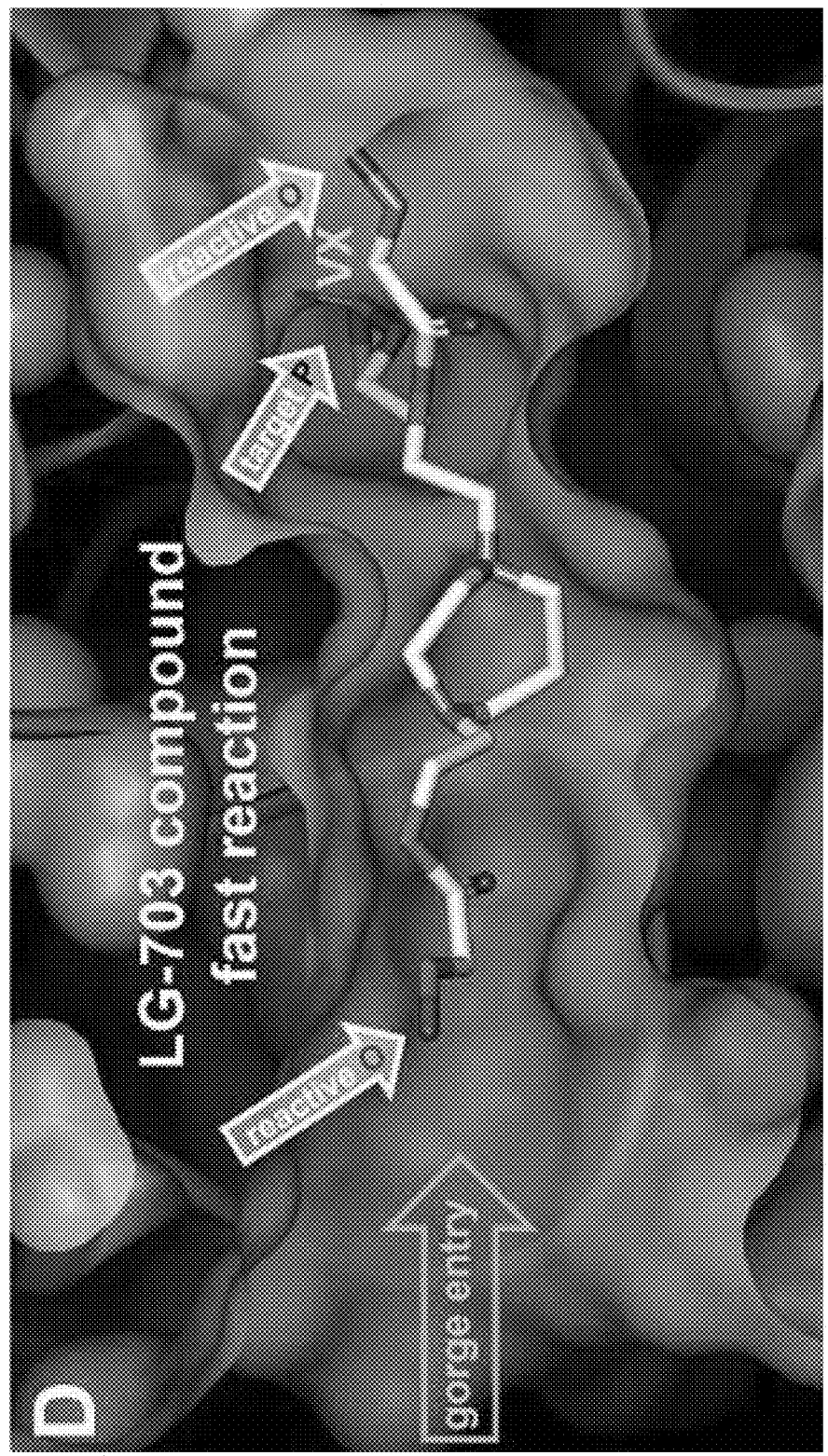

FIG. 37A-D illustrate images showing the productive re-orientation of the "reactive O" of the oxime group in acetylcholinesterase (hAChE) enzyme active site gorge by exemplary LG compounds as provided herein, as compared to RS194B; reactive O points towards gorge entry in X-ray structures of both FIG. 37A: RS194B*hAChE complex and FIG. 37B: RS194B*VX-hAChE conjugate complex, while FIG. 37C: one of two Reactive O atoms of the LG-703 assumes productive orientation towards interior of the gorge in the LG-703*hAChE complex and FIG. 37D: "target P" of the VX as shown in the superposition of LG-703 into the VX-hAChE conjugate X-ray structure, as described in detail in Example 1, below.

FIG. 38 illustrates Table 4, kinetic constants for in vitro reactivation by LG bis-oximes and RS194B monoxime; maximal reactivation rate constant $k_2$ (min$^{-1}$), Michaelis-Menten type constant $K_{ox}$ (mM), and the overall second order reactivation rate constant $k_r$ (M$^{-1}$ min$^{-1}$) were calculated by non-linear regression from curves in FIG. 35; different shading for LG bis-oximes indicates difference in the central heterocycle (yellow-homopiperazines; white-piperazines; blue-piperidines).

Figure 39:
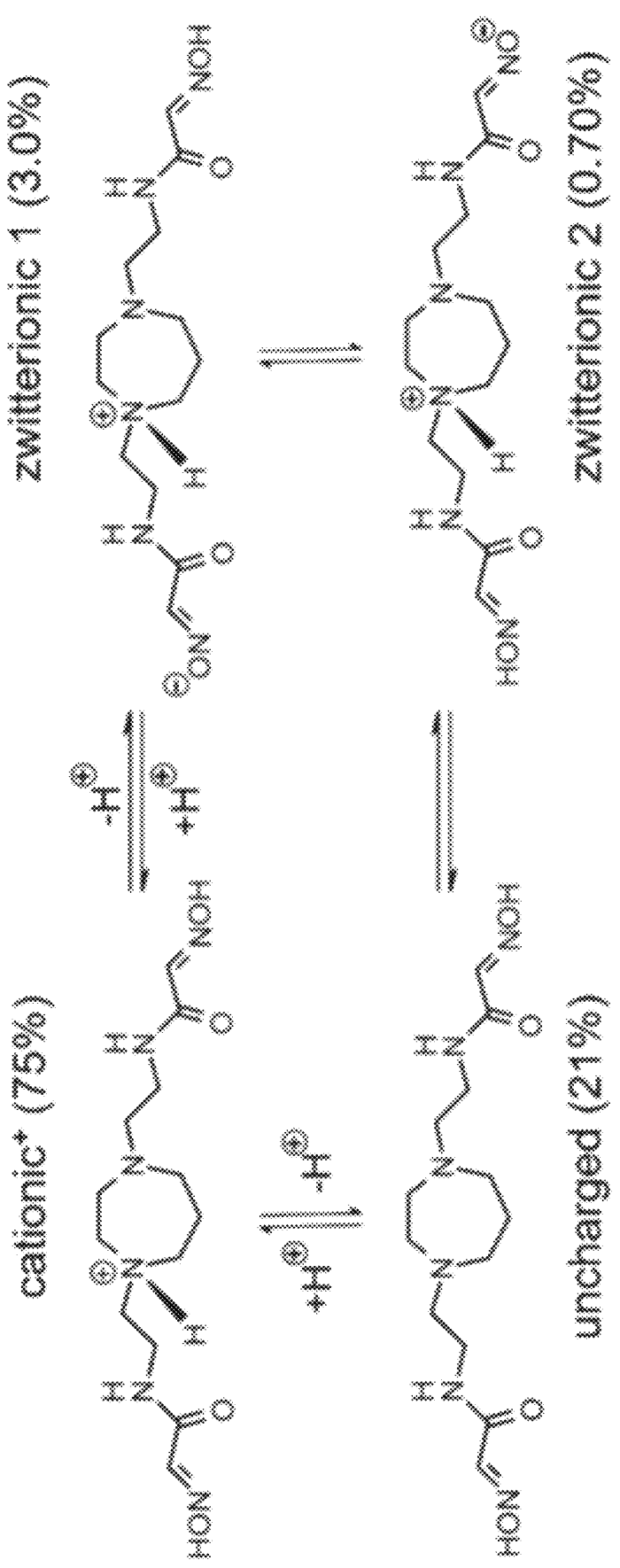

FIG. 39 illustrates ionization equilibria and abundance at pH 7.4, of four most abundant individual ionization forms for bis-oxime LG-703 (out of sixteen possible forms).

Figure 40A:
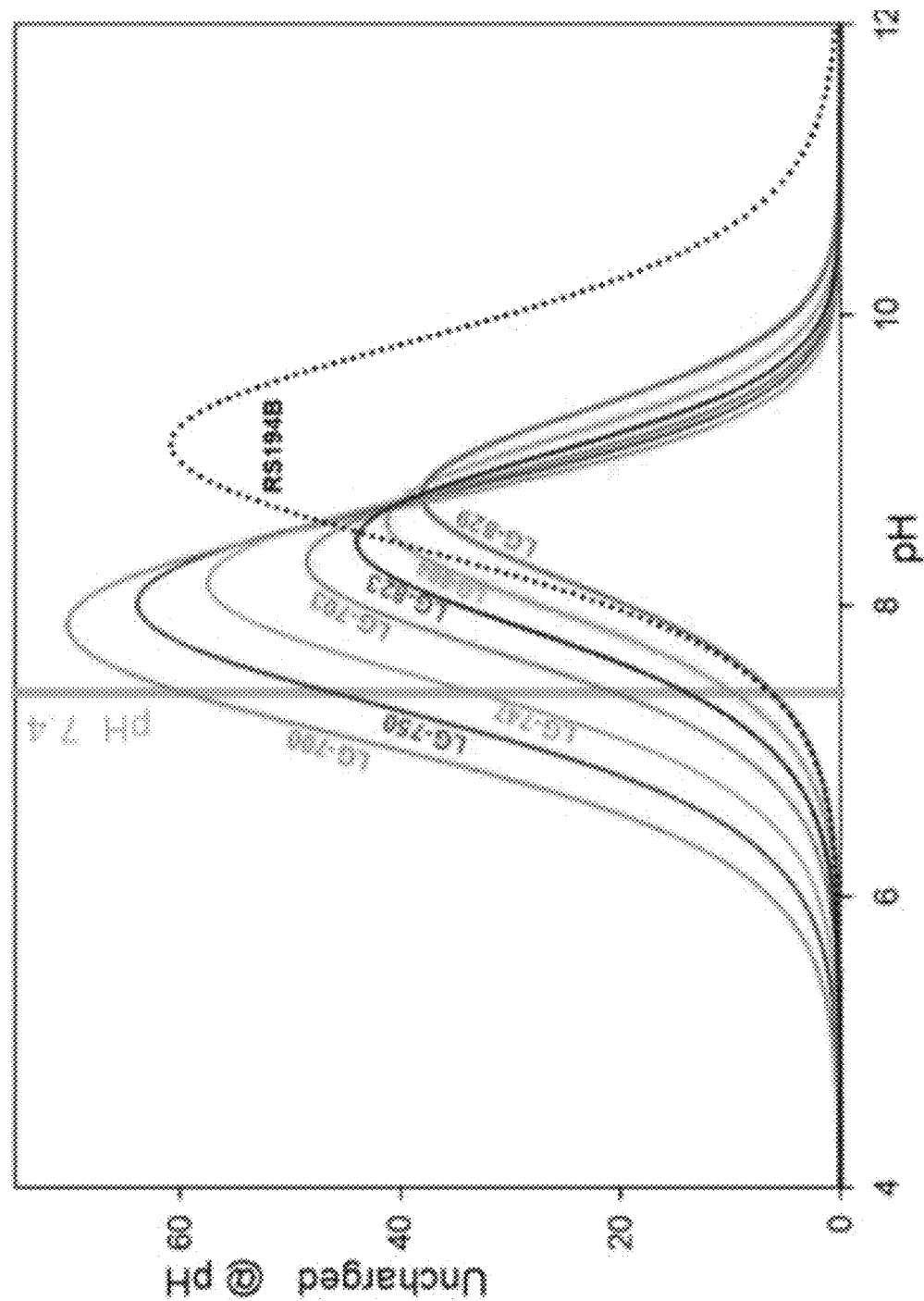

FIG. 40A-B graphically illustrate pH dependent abundance of ionization species for all LG bis-oximes compared to monoxime RS194B; FIG. 40A shows uncharged oxime species and FIG. 45B shows zwitterionic oxime species; curves were calculated using $pK_a$ values from FIG. 34.

Like reference symbols in the various drawings indicate like elements.

DETAILED DESCRIPTION

In alternative embodiments, provided are uncharged bis-oxime antidotes that cross the blood-brain barrier (BBB) to catalyze the hydrolysis of organophosphate (OP)-inhibited human acetylcholinesterase (hAChE) in the central nerve system (CNS) to reactivate the hAChE, including products of manufacture and kits, and methods, comprising or using these compositions.

Novel compounds were designed and synthesized that can recover activity of OP-inhibited human acetylcholinesterase (AChE) (for example, inhibited by a nerve agent or an OP pesticide) target enzyme in OP intoxication more efficiently than existing antidotes in use, including the seven exemplary compounds LG-829; LG-823; LG-804; LG-703; LG-750; LG-747; and, LG-700.

Because they are not charged molecules, compounds as provided herein (including the exemplary LG-829; LG-823; LG-804; LG-703; LG-750; LG-747; and, LG-700) have predisposition for crossing biological membranes including the blood-brain barrier (BBB), to diffuse into CNS and recover activity of CNS (e.g., brain) AChE. Standard antidotes, such as 2-PAM or the pyridinium or imidazolium aldoximes or various pro-drugs forming pyridinium aldoximes, are not capable of crossing the BBB at an appreciable rate and reactivating brain AChE. Ability to cross the BBB at an appreciable rate, a property of exemplary compounds as provided herein, is critical for full and fast recovery from OP intoxication.

Existing uncharged antidotes, such as RS194B have similar capacity but to a smaller extent, and only one reactive center compared to two centers in the new compounds as provided herein. Our in vitro data show that compounds as provided herein can act up to several-fold faster compared to existing the experimental uncharged RS194B antidote.

Our novel compounds as provided herein (including the exemplary LG-829; LG-823; LG-804; LG-703; LG-750; LG-747; and, LG-700) have two reactive centers in their structure and therefore act faster and have capacity to recover AChE activity from human blood/diaphragm and brain in shorter time than existing antidotes with just one reactive center (such as RS194B). Fast recovery of AChE activity is critical for saving lives of OP intoxicated individuals.

Compounds as provided herein (including the exemplary LG-829; LG-823; LG-804; LG-703; LG-750; LG-747; and, LG-700) are uncharged and will cross biological membranes including blood-brain barrier (BBB), unlike 2PAM.

In alternative embodiments, compounds as provided herein are uncharged and have either three or four ionizable groups. In solution, such as human blood, ionization equilibria can be established where the compound will be either uncharged, have one or two protonated centers or have both one or two protonated centers with two anionic centers. Three forms should be dominant: uncharged, singly protonated and zwitterionic singly protonated with one anionic center. The bis-oxime compounds have desirable capacity to form more than one kind of zwitterionic form (see FIG. 39) at higher concentration than RS194B (see FIG. 40). The uncharged form will cross the BBB, then re-equilibrate to form protonated form that will bind to the inhibited molecular target (OP-hAChE). Protonated molecular forms with one reactive anionic center will chemically react within molecular target and will recover its inhibited activity.

In alternative embodiments, compounds as provided herein have two "reactive anionic O" centers that react faster than RS194B that has only one such center. While the invention is not limited by any particular mechanism of action, compounds as provided herein can direct one of their two "reactive O" groups closely towards their target P atom of an OP inhibitor (VX in panels B and D) resulting in recovery of enzyme function.

We have demonstrated by our own X-ray structures (see FIG. A, 1B, 1C and 1D, and FIG. 37A and 37B) that RS194B compound most of the time directs its reactive group away from its target P of the OP (VX) (FIG. 1A and 1B). Our x-ray structure of one exemplary LG compound as provided herein (exemplary compound LG-703) shows that it directs one of its two reactive O groups in direction where OP (VX) binds (see FIG. 36A, 36B, and 36C; and FIG. 37D), explaining why this and other exemplary LG compounds as provided herein recover enzyme activity faster and more efficiently than RS194B compound.

FIG. 37 illustrates an image showing the productive re-orientation of the "reactive O" of the oxime group in exemplary LG compounds as provided herein compared to RS194B. Reactive O points towards gorge entry in X-ray structures of both FIG. 37A: RS194B*hAChE complex and FIG. 37B: RS194B*VX-hAChE conjugate complex, while FIG. 37C: one of two Reactive O atoms of the LG-703 assumes productive orientation towards interior of the gorge in the LG-703 *hAChE complex and FIG. 37D: "target P" of the VX as shown in the superposition of LG-703 into the VX-hAChE conjugate X-ray structure.

As discussed in Example 1, below, we have in vitro efficacy functional data for reactivation rates analyzed with deconstructed kinetic constants for the seven exemplary compounds LG-829; LG-823; LG-804; LG-703; LG-750; LG-747; and, LG-700, in reactivation of four OP inhibited hAChE forms: paraoxon-hAChE, VX-hAChE, sarin-hAChE and cyclosarin-hAChE. Also as discussed in Example 1, we have X-ray structural data confirming a proposed mechanism of exemplary compound reaction at the molecular level, see FIG. 1, FIG. 36 and FIG. 37. By this mechanism LG bis-oximes, whenever bound to the OP-hAChE, point at least one of their two nucleophilic reactive groups towards their reactivation target, OP conjugated Ser203 of hAChE, while RS194B compound points its single reactive group most of the time away from this intended reactivation target.

In alternative embodiments, the term "alkyl" refers to a saturated chain containing only carbon atoms, which may be linear or branched. Alkyl groups may be further substituted at any atom independently with additional alkyl, alkyloxy, alkylamino, alkylthio, acyl, sulfonyl, cycloalkyl, heterocycloalkyl, phenyl or heteroaryl groups as defined herein. Alkyl groups may be substituted at any atom independently with heteroatoms chosen from N, O or S, which may be further substituted independently with additional hydrogen, alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. When the heteroatom is N, O or S, it may form a double bond to the chain as in a ketone or an oxime. When the heteroatom is S, it may be oxidized at S with one or more O atoms, as a sulfoxide or sulfone. Alkyl groups may be substituted at any atom independently with halogens chosen from F, Cl, Br or I, and may be disubstituted as in, for example, a —$CF_2$-group in the chain, or trisubstituted as in, for example, a $CF_3$ group at the terminus of the chain. Alkyl groups may be fused through a single disubstituted atom in the chain to a ring to form a cycloalkyl or heterocycloalkyl structure. Alkyl group size is defined, for example, as $C_{1-6}$, which refers to the number of atoms in the group. Some non-limitative examples of linear alkyl groups include methyl, ethyl, propyl, butyl, pentyl or hexyl. Some non-limitative examples of branched alkyl groups include isopropyl, isobutyl, sec-butyl, tert-butyl or tert-amyl.

In alternative embodiments, the term "alkenyl" refers to a fully or partially unsaturated chain containing only carbon atoms, which may be linear or branched, containing at least one carbon-carbon double bond. Alkenyl groups may be further substituted at any atom independently with additional alkyl, alkyloxy, alkylamino, alkylthio, acyl, sulfonyl, cycloalkyl, heterocycloalkyl, phenyl or heteroaryl groups as defined herein. Alkenyl groups may be substituted at any atom independently with heteroatoms chosen from N, O or S, which may be further substituted independently with additional alkyl, alkyloxy, alkylamino, alkylthio, acyl, sulfonyl, cycloalkyl, heterocycloalkyl, phenyl or heteroaryl groups. When the heteroatom is N, it may be substituted twice independently with alkyl, alkyloxy, alkylamino, alkylthio, acyl, sulfonyl, cycloalkyl, heterocycloalkyl, phenyl or heteroaryl groups. When the heteroatom is N, O or S, it may form a double bond to the chain as in a ketone or an oxime. When the heteroatom is S, it may be oxidized at S with one or more O atoms, as a sulfoxide or sulfone. Alkenyl groups may be substituted at any atom independently with halogens chosen from F, Cl, Br or I, and may be disubstituted as in, for example, a —$CF_2$-group in the chain or a =$CF_2$ group at the terminus of the chain, or trisubstituted as in, for example, a $CF_3$ group at the terminus of the chain. Alkenyl groups may be fused through a single disubstituted atom in the chain to a ring to form a cycloalkyl or heterocycloalkyl structure. Alkenyl group size is defined, for example, as $C_{1-6}$, which refers to the number of atoms in the group. Some non-limitative examples of linear alkenyl groups include vinyl, allyl, allenyl or 2-propenyl. Some non-limitative examples of branched alkyl groups include isopropenyl or methallyl.

In alternative embodiments, the term "alkynyl" refers to a fully or partially unsaturated chain containing only carbon atoms, which may be linear or branched, containing at least one carbon-carbon triple bond. Alkynyl groups may be further substituted at any atom independently with additional alkyl, alkyloxy, alkylamino, alkylthio, acyl, sulfonyl, cycloalkyl, heterocycloalkyl, phenyl or heteroaryl groups as defined herein. Alkynyl groups may be substituted at any atom independently with heteroatoms chosen from N, O or S, which may be further substituted independently with additional alkyl, alkyloxy, alkylamino, alkylthio, acyl, sulfonyl, cycloalkyl, heterocycloalkyl, phenyl or heteroaryl groups. When the heteroatom is N, it may be substituted twice independently with alkyl, alkyloxy, alkylamino, alkylthio, acyl, sulfonyl, cycloalkyl, heterocycloalkyl, phenyl or heteroaryl groups. When the heteroatom is N, O or S, it may form a double bond to the chain as in a ketone or an oxime. When the heteroatom is S, it may be oxidized at S with one or more O atoms, as a sulfoxide or sulfone. Alkynyl groups may be substituted at any atom independently with halogens chosen from F, Cl, Br or I, and may be disubstituted as in, for example, a —$CF_2$— group in the chain, or trisubstituted as in, for example, a $CF_3$ group at the terminus of the chain. Alkynyl groups may be fused through a single disubstituted atom in the chain to a ring to form a cycloalkyl or heterocycloalkyl structure. Alkynyl group size is defined, for example, as $C_{1-6}$, which refers to the number of atoms in the group. Some non-limitative examples of linear alkynyl groups include ethynyl or propargyl.

In alternative embodiments, the term "alkyloxy" refers to a saturated chain containing carbon and oxygen atoms, which may be linear or branched, where the connection to a compound as provided herein is through a carbon-carbon bond. Alkyloxy groups may be further substituted at any oxygen atom independently with additional hydrogen, alkyl, alkyloxy, alkylamino, alkylthio, cycloalkyl, heterocycloalkyl, phenyl or heteroaryl groups, as defined herein, to form an ether. Alkyloxy groups may be further substituted at any oxygen atom independently with an additional acyl or sulfonyl group to form an ester, carbonate, carbamate, sulfonate or sulfamate. Alkyloxy groups may be substituted at any atom independently with halogens chosen from F, Cl, Br or I, and may be disubstituted as in, for example, a —$CF_2$— group in the chain, or trisubstituted as in, for example, a $CF_3$ group at the terminus of the chain. Alkyloxy groups may be fused through a single disubstituted atom in the chain to a ring to form a cycloalkyl or heterocycloalkyl structure. Alkyloxy group size is defined, for example, as $C_{1-6}$, which refers to the number of atoms in the group, and wherein one or more C is replaced independently by O. Some non-limitative examples of alkyloxy groups include methoxymethyl, methoxyethyl, isopropoxymethyl, or hydroxymethyl.

In alternative embodiments, the term "alkylamino" refers to a saturated chain containing carbon and nitrogen atoms, which may be linear or branched, where the connection to a compound as provided herein is through a carbon-carbon bond. Alkylamino groups may be further substituted at any nitrogen atom independently with one or more additional hydrogen, alkyl, alkyloxy, alkylamino, alkylthio, acyl, sulfonyl, cycloalkyl, heterocycloalkyl, phenyl, or heteroaryl groups. Alkylamino groups may be substituted at any atom independently with halogens chosen from F, Cl, Br or I, and may be disubstituted as in, for example, a —$CF_2$— group in the chain, or trisubstituted as in, for example, a $CF_3$ group at the terminus of the chain. Alkylamino groups may be fused through a single disubstituted atom in the chain to a ring to form a cycloalkyl or heterocycloalkyl structure. Alkylamino groups may contain a nitrogen atom that is part of a ring system, such as a lactam or sultam, as defined herein. Alkylamino group size is defined, for example, as $C_{1-6}$, which refers to the number of atoms in the group, and wherein one or more C is replaced independently by N. Some non-limitative examples of alkylamino groups include methylmethanamino and aminomethyl.

In alternative embodiments, the term "alkylthio" refers to a saturated chain containing carbon and sulfur atoms, which may be linear or branched, where the connection to a compound as provided herein is through a carbon-carbon bond. Alkylthio groups may be further substituted at any sulfur atom independently with additional hydrogen, alkyl, alkyloxy, alkylamino, alkylthio, cycloalkyl, heterocycloalkyl, phenyl or heteroaryl groups, as defined herein, to form a thioether. Alkylthio groups may be further substituted at any sulfur atom independently with an additional acyl group to form a thioester. Alkylthio groups may be oxidized at any sulfur atom independently with one or more O atoms, as a sulfoxide or sulfone. Alkylthio groups may be further substituted at any sulfur atom in the $SO_2$ oxidation state with an additional nitrogen to form a sulfonamide, which may be substituted twice independently at N with hydrogen, alkyl, alkyloxy, alkylamino, alkylthio, acyl, cycloalkyl, heterocycloalkyl, phenyl or heteroaryl groups. Alkylthio groups may be substituted at any atom independently with halogens chosen from F, Cl, Br or I, and may be disubstituted as in, for example, a —$CF_2$— group in the chain, or trisubstituted as in, for example, a $CF_3$ group at the terminus of the chain. Alkylthio groups may be fused through a single disubstituted atom in the chain to a ring to form a cycloalkyl or heterocycloalkyl structure. Alkylthio group size is defined, for example, as $C_{1-6}$, which refers to the number of atoms in the group, and wherein one or more C is replaced independently by S. Some non-limitative examples of alkylthio groups include methylthiomethyl and thiomethyl.

In alternative embodiments, the term "cycloalkyl" refers to a saturated or partially unsaturated ring system containing only carbon atoms in the backbone of the ring. When the cycloalkyl ring is partially unsaturated, it may contain one or more double bonds but is not aromatic. Cycloalkyl rings may be further substituted at any atom independently with additional hydrogen, alkyl, alkyloxy, alkylamino, alkylthio, acyl, sulfonyl, cycloalkyl, heterocycloalkyl, phenyl or heteroaryl groups as defined herein. Cycloalkyl rings may be substituted at any atom independently with exocyclic heteroatoms chosen from N, O or S, which may be further substituted independently with additional hydrogen, alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. When the heteroatom is N, O or S, it may form a double bond to the ring as in a ketone or an oxime. When the heteroatom is S, it may be oxidized at S with one or more O atoms, as a sulfoxide or sulfone. Cycloalkyl rings may be substituted at any atom independently with halogens chosen from F, Cl, Br or I, and may be disubstituted as in, for example, a —$CF_2$— group in the ring backbone. Cycloalkyl rings may be monocyclic, wherein all of the atoms of the cycloalkyl ring are contained in a single ring, or may be part of a polycyclic ring system containing multiple rings. Cycloalkyl rings may be fused through two adjacent atoms to an additional ring, which may be substituted cycloalkyl, heterocycloalkyl, phenyl or heteroaryl as defined herein, to form a bicyclic ring system. Cycloalkyl rings may be fused through a single disubstituted atom to an additional ring to form a spirocyclic cycloalkyl or heterocycloalkyl structure. Cycloalkyl rings may also contain a bridging structure, which may be 1-2 carbon atoms. Cycloalkyl groups may optionally include multiple ring fusions, spirocyclic fusions or bridged structures, or a combination of these, as part of a larger ring system containing multiple rings. In alternative embodiments, a cycloalkyl ring size is a $C_{3-10}$, which refers to the number of atoms in the backbone of the ring. Some non-limitative examples of cycloalkyl rings include cyclopropane, cyclobutane, cyclopentane, cyclopentene, cyclohexane, cyclohexene, cycloheptane, cycloheptene, cycloheptadiene, cyclooctane, cyclooctene, cyclooctadiene, spiro[3.3]heptane, spiro[4.4]nonane, norbornane, bicyclo[2.2.1]heptane, bicyclo[2.2.2]octane, indane, tetralone.

In alternative embodiments, the term "heterocycloalkyl" refers to a saturated or partially unsaturated ring system having one or more heteroatoms chosen from N, O or S in the backbone of the ring, where the connection to a compound as provided herein is through a carbon-carbon bond or a carbon-nitrogen bond. When the heterocycloalkyl ring is partially unsaturated, it may contain one or more double bonds but is not aromatic. Heterocycloalkyl rings may be further substituted at any C or N atom independently with additional hydrogen, alkyl, alkyloxy, alkylamino, alkylthio, acyl, sulfonyl, cycloalkyl, heterocycloalkyl, phenyl or heteroaryl as defined herein. Heterocycloalkyl rings containing one or more S atom in the ring backbone may be oxidized at S with one or more O atoms, as a sulfoxide or sulfone. Heterocycloalkyl rings may be lactams or sultams, as defined herein. Heterocycloalkyl rings may be substituted at any atom independently with exocyclic heteroatoms chosen from N, O or S, which may be further substituted independently with additional alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. When the heteroatom is N, O or S, it may form a double bond to the ring as in a ketone or an oxime. When the heteroatom is S, it may be oxidized at S with one or more O atoms, as a sulfoxide or sulfone. Heterocycloalkyl rings may be substituted at any atom independently with halogens chosen from F, Cl, Br or I, and may be disubstituted as in, for example, a $CF_2$ group in the ring backbone. Heterocycloalkyl rings may be monocyclic, wherein all of the atoms of the heterocycloalkyl ring are contained in a single ring, or may be part of a polycyclic ring system containing multiple rings. Heterocycloalkyl rings may be fused through two adjacent atoms to an additional ring, which may be substituted cycloalkyl, heterocycloalkyl, phenyl or heteroaryl as defined herein, to form a bicyclic ring system. Heterocycloalkyl rings may be fused through a single atom to an additional ring to form a spirocyclic bicyclic structure. Heterocycloalkyl rings may also contain a bridging structure, which may be 1-2 atoms, to form a bicyclic ring system. Heterocycloalkyl groups may optionally include multiple ring fusions, spirocyclic fusions or bridged structures, or a combination of these, as part of a larger ring system containing multiple rings. Heterocycloalkyl ring size is defined, for example, as $C_{4-10}$, which refers to the number of atoms in the ring, and wherein one or more C is replaced independently by a heteroatom. Some non-limitative examples of $C_4$ heterocycloalkyl rings are oxetane, azetidine or β-lactam. Some non-limitative examples of $C_5$ heterocycloalkyl rings are tetrahydrofuran, pyrrolidine, or sulfolane. Some non-limitative examples of $C_6$ heterocycloalkyl rings are tetrahydropyran, piperidine, piperazine, tetrahydrothiopyran or 1,1-dioxo-tetrahydrothiopyran. Some non-limitative examples of $C_7$ heterocycloalkyl rings are hexamethyleneimine, diazepane or oxazepine. Some non-limitative examples of $C_8$ heterocycloalkyl rings are oxocane or heptamethyleneimine.

In alternative embodiments, the term "phenyl" refers to a benzene ring, which may be substituted independently at any position with additional hydrogen, alkyl, alkyloxy, alkylamino, alkylthio, acyl, sulfonyl, cyano, cycloalkyl, heterocycloalkyl, phenyl or heteroaryl groups as defined herein. Phenyl groups may be substituted at any atom independently with heteroatoms chosen from N, O or S, which may be further substituted independently with additional hydrogen, alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. When the heteroatom is S, it may be oxidized at S with one or more O atoms, as a sulfoxide or sulfone. Phenyl groups may be substituted at any atom independently with halogens chosen from F, Cl, Br or I. Phenyl groups may be fused through two adjacent atoms to an additional ring, which may be substituted cycloalkyl, heterocycloalkyl, phenyl or heteroaryl as defined herein. Phenyl groups may optionally include multiple ring fusions, optionally further substituted with spirocyclic fusions or bridged structures, or a combination of these, as part of a larger ring system containing multiple rings. Some non-limitative examples of phenyl groups include benzene, naphthalene, indane or tetrahydronaphthalene.

In alternative embodiments, the term "heteroaryl" refers to an aromatic ring system having one or more heteroatoms chosen from N, O or S in the backbone of the ring, where the connection to a compound as provided herein is through a carbon-carbon or carbon-nitrogen bond. Heteroaryl rings may be further substituted at any C or N atom independently with additional alkyl, alkyloxy, alkylamino, alkylthio, acyl, sulfonyl, cyano, cycloalkyl, heterocycloalkyl, phenyl or heteroaryl groups as defined herein. Heteroaryl groups may be substituted at any carbon atom independently with heteroatoms chosen from N, O or S, which may be further substituted independently with additional hydrogen, alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. When the heteroatom is O, it may form a double bond to the ring as in a ketone, which may be a tautomer of an OH group. When the heteroatom is S, it may be oxidized at S with one or more O atoms, as a sulfoxide or sulfone. Heteroaryl groups may be substituted at any atom independently with halogens chosen from F, Cl, Br or I. Heteroaryl rings may be monocyclic, wherein all of the atoms of the heteroaryl ring are contained in a single ring, or may be part of a bicyclic ring system containing two rings. Heteroaryl groups may be fused through two adjacent atoms to an additional ring, which may be substituted cycloalkyl, heterocycloalkyl, phenyl or heteroaryl as defined herein. Heteroaryl groups may optionally include multiple ring fusions, optionally further substituted with spirocyclic fusions or bridged structures, or a combination of these, as part of a larger ring system containing multiple rings. Some non-limitative examples of heteroaryl groups include pyrrole, imidazole, pyrazole, furan, thiophene, oxazole, isoxazole, thiazole, isothiazole, 1,2,4-oxadiazole, 1,2,5-oxadiazole, 1,3,4-oxadiazole, 1,2,4-thiadiazole, 1,2,5-thiadiazole, 1,3,4-thiadiazole, 1,2,3-triazole, 1,2,4-triazole, tetrazole, pyridine, pyrimidine, pyrazine, pyridazine, quinoline, isoquinoline, quinazoline, indole, indazole, benzimidazole, benzofuran, benzothiophene, benzoxazole, benzisoxazole or benzisothiazole.

In alternative embodiments, the term "acyl" refers to a carbon-oxygen double bond as in a carbonyl. Acyl groups may be further substituted at the carbon atom with alkyl, alkyloxy, alkylamino, alkylthio, acyl, sulfonyl, cycloalkyl, heterocycloalkyl, phenyl or heteroaryl groups as defined herein. Acyl groups may be substituted at the carbon atom with heteroatoms chosen from N, O or S, as in, for example, an amide, carbamate, urea, ester, carbonate, thioester, or thiocarbamate, where the heteroatom may be further substituted independently with additional hydrogen, alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. Some non-limitative examples of acyl groups include acetyl, benzoyl, or acetamido.

In alternative embodiments, the term "sulfonyl" refers to a sulfur atom substituted with two sulfur-oxygen double bonds, as in $SO_2$. Sulfonyl groups may be further substituted at the sulfur atom with alkyl, alkyloxy, alkylamino, alkylthio, acyl, sulfonyl, cycloalkyl, heterocycloalkyl, phenyl or heteroaryl groups as defined herein. Sulfonyl groups may be substituted at the sulfur atom with heteroatoms chosen from N or O, as in, for example, a sulfonamide or sulfonate, where the heteroatom may be further substituted independently with additional hydrogen, alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. Some non-limitative examples of sulfonyl groups include methanesulfonyl, p-toluenesulfonyl, or sulfonamido.

In alternative embodiments, the term "lactam" refers to a saturated or partially unsaturated ring having at least one N atom in the backbone of the ring, and where at least one carbon in the backbone of the ring is substituted with a double bond to an exocyclic O atom, as in a carbonyl, and where an N atom of the ring is bonded to a carbonyl carbon in the ring as in an amide. Lactam rings may contain one or more additional heteroatoms chosen from N, O or S in the backbone of the ring. When the lactam ring is partially unsaturated, it may contain one or more double bonds but is not aromatic. Lactam rings may be further substituted at any C or N atom independently with additional alkyl, alkyloxy, alkylamino, alkylthio, acyl, sulfonyl, cycloalkyl, heterocycloalkyl, phenyl or heteroaryl groups as defined herein. Lactam rings containing one or more S atom in the ring backbone may be oxidized at S with one or more O atoms, as a sulfoxide or sulfone. Lactam rings may be substituted at any atom independently with heteroatoms chosen from N, O or S, which may be further substituted independently with additional hydrogen, alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. When the heteroatom is O, it may form a double bond to the ring as in a ketone. When the heteroatom is S, it may be oxidized at S with one or more O atoms, as a sulfoxide or sulfone. Lactam rings may be substituted at any atom independently with halogens chosen from F, Cl, Br or I, and may be disubstituted as in, for example, a $CF_2$ group in the ring backbone. Lactam rings may be fused through two adjacent atoms to an additional ring, which may be substituted cycloalkyl, heterocycloalkyl, phenyl or heteroaryl as defined herein. Lactam rings may be monocyclic, wherein all of the atoms of the cycloalkyl ring are contained in a single ring, or may be part of a bicyclic ring system containing two rings. Lactam rings may be fused through two adjacent atoms to an additional ring, which may be substituted cycloalkyl, heterocycloalkyl, phenyl or heteroaryl as defined herein. Lactam rings may be fused through a single atom to an additional ring to form a spirocyclic structure. Lactam rings may also contain a bridging structure, which may be 1-2 atoms. Lactam ring size is defined, for example, as $C_{4-10}$, which refers to the number of atoms in the ring, and wherein one or more C is replaced independently by a heteroatom. Some non-limitative examples of lactams include 2-azetidinone, 2-pyrrolidinone and 3-morpholinone.

In alternative embodiments, the term "sultam" refers to a saturated or partially unsaturated ring having at least one N atom and at least one S atom in the backbone of the ring, and where at least one S atom in the backbone of the ring is substituted with double bonds to two exocyclic O atom, as in a sulfonyl group, and where an N atom of the ring is bonded to a sulfonyl sulfur in the ring as in a sulfonamide. Sultam rings may contain one or more additional heteroatoms chosen from N, O or S in the backbone of the ring. When the sultam ring is partially unsaturated, it may contain one or more double bonds but is not aromatic. Sultam rings may be further substituted at any C or N atom independently with additional alkyl, alkyloxy, alkylamino, alkylthio, acyl, sulfonyl, cycloalkyl, heterocycloalkyl, phenyl or heteroaryl groups as defined herein. Sultam rings containing one or more additional S atoms in the ring backbone may be oxidized at S with one or more O atoms, as a sulfoxide or sulfone. Sultam rings may be substituted at any atom independently with heteroatoms chosen from N, O or S, which may be further substituted independently with additional hydrogen, alkyl, alkyloxy, alkylamino, alkylthio, acyl, sulfonyl, cycloalkyl, heterocycloalkyl, phenyl or heteroaryl groups. When the heteroatom is N, it may be substituted twice independently with hydrogen, alkyl, alkyloxy, alkylamino, alkylthio, acyl, sulfonyl, cycloalkyl, heterocycloalkyl, phenyl or heteroaryl groups. When the heteroatom is N or O, it may form a double bond to the ring as in a ketone or an oxime. When the heteroatom is S, it may be oxidized at S with one or more O atoms, as a sulfoxide or sulfone. Sultam rings may be substituted at any atom independently with halogens chosen from F, Cl, Br or I, and may be disubstituted as in, for example, a $CF_2$ group in the ring backbone. Sultam rings may be monocyclic, wherein all of the atoms of the cycloalkyl ring are contained in a single ring, or may be part of a bicyclic ring system containing two rings. Sultam rings may be fused through two adjacent atoms to an additional ring, which may be substituted cycloalkyl, heterocycloalkyl, phenyl or heteroaryl as defined herein. Sultam rings may be fused through a single atom to an additional ring to form a spirocyclic structure. Sultam rings may also contain a bridging structure, which may be 1-2 atoms. Sultam ring size is defined, for example, as $C_{4-10}$, which refers to the number of atoms in the ring, and wherein two or more C are replaced independently by a heteroatom. Some non-limitative examples of sultams include 1,3-propanesultam or 1,2-thiazinane 1,1-dioxide.

In alternative embodiments, the term "cyano" refers to a carbon-nitrogen triple bond, where the connection to a compound as provided herein is through a carbon-carbon bond.

In alternative embodiments, the term "halogen" refers to the atoms fluorine, chlorine, bromine or iodine. In alternative embodiments, the term "hydroxy" refers to an oxygen atom substituted with a hydrogen atom, as in an alcohol or a phenol. A hydroxy group attached to an atom adjacent to another heteroatom may exist as the keto tautomer.

Bioisosteres of Compounds

In alternative embodiments, provided are bioisosteres of compounds as provided herein. In alternative embodiments, bioisosteres as provided herein are compounds as provided herein comprising one or more substituent and/or group replacements with a substituent and/or group having substantially similar physical or chemical properties which produce substantially similar biological properties to a compound as provided herein, or stereoisomer, racemate or isomer thereof. In one embodiment, the purpose of exchanging one bioisostere for another is to enhance the desired biological or physical properties of a compound without making significant changes in chemical structures.

For example, in one embodiment, bioisosteres as provided herein are made by replacing one or more hydrogen atom(s) with one or more fluorine atom(s), e.g., at a site of metabolic oxidation; this may prevent metabolism (catabolism) from taking place. Because the fluorine atom is only slightly larger than the hydrogen atom the overall topology of the molecule is not significantly affected, leaving the desired biological activity unaffected. However, with a blocked pathway for metabolism, the molecule may have a longer half-life or be less toxic, and the like.

Products of Manufacture, Kits

Also provided are products of manufacture and kits for practicing the methods as provided herein. In alternative embodiments, provided are products of manufacture and kits comprising all the components needed to practice a method as provided herein.

Provided are kits comprising compositions and/or instructions for practicing methods as provided herein. In alternative embodiments, provided are kits comprising: a composition used to practice a method as provided herein, optionally comprising instructions for use thereof.

In alternative embodiments, provided are pumps, devices, subcutaneous infusion devices, continuous subcutaneous infusion device, infusion pens, needles, reservoirs, ampoules, vials, syringes, cartridges, disposable pen or jet injectors, prefilled pens or syringes or cartridges, cartridge or disposable pen or jet injectors, two chambered or multi-chambered pumps, syringes, cartridges or pens or jet injectors comprising a composition or a formulation as provided herein. In alternative embodiments, the injector is an auto-injector, e.g., a SMARTJECT® autoinjector (Janssen Research and Development LLC); or a MOLLY®, or DAI®, or DAI-RNS® autoinjector (SHL Group, Deerfield Beach, Fla.). In alternative embodiments, the injector is a hypodermic or a piston syringe.

Hand-Held or Portable Devices

In alternative embodiments, provided are products of manufacture fabricated or manufactured as a portable, e.g., hand-held (or worn around the neck), medical device, e.g., an inhaler, a nebulizer (e.g., an asthma-type nebulizer), comprising, or for administering, a composition or a formulation as provided herein, where in alternative embodiments the product of manufacture administers an inhalation product (e.g., powder, mist, any liquid spray) comprising a composition or a formulation as provided herein.

As discussed above, in alternative embodiments, the portable or hand-held medical device comprises a cassette, packette, interchangeable disk (e.g., for holding a powder) or reservoir (optionally a refillable reservoir) in or on the product of manufacture, or a removable cassette or packette, interchangeable disk (e.g., for holding a powder) that can be inserted into a slot or port on the product of manufacture, or a separate reservoir or container operatively linked or joined to the product of manufacture, that comprises a composition or a formulation as provided herein for inhalation delivery to a user.

In alternative embodiments, a product of manufacture, e.g., a medical device, as provided herein for inhalation delivery of a composition or a formulation as provided herein to a user is fabricated as a meter-dose inhaler (MDI) (either open or closed mouth MDI), which can comprise a pressurized canister of the drug or medication in a plastic case with a mouthpiece, and a holding chamber having a plastic tube with a mouthpiece, a valve to control mist delivery and a soft sealed end to hold the MDI; the holding chamber can assist delivery of the drug or medication to the nose and/or lungs, e.g., as an AEROCHAMBER™ device. In alternative embodiments, the inhaler or nebulizer is breath activated, e.g., as an REDIHALER™ device.

In alternative embodiments, a product of manufacture, e.g., a medical device, as provided herein for inhalation delivery of a composition or a formulation as provided herein to a user is fabricated a dry powder inhaler (such as a dry powder disk inhaler, e.g., as a DISKUS™ device), optionally having a dose counter window so user can see how many doses are left), e.g., where the powder is dose dispensed by (using) a disposable, refillable or replaceable cassette, packette or disk; and the dry powder dispensing can be breath activated, e.g., as an AEROLIZER™ FLEXHALER™, PRESSAIR™, DISKUS™, HANDIHALER™, TWISTHALER™, ELLIPTA™, NEOHALER™, RESPICLICK™, ROTAHALER™ or TUBUHALER™ device.

In alternative embodiments, provided is a product of manufacture, e.g., a medical device, for inhalation delivery of a composition or a formulation as provided herein to a user is fabricated a nebulizer or soft mist inhaler, which can comprise a nebulizer delivery system comprising a nebulizer (e.g., a small plastic bowl with a screw-top lid) and a source for compressed air to generate a mist comprising the drug or medication, which also can be dose dispensed using a disposable, refillable or replaceable cassette, packette or disk.

Formulations and Pharmaceutical Compositions

In alternative embodiments, provided are compounds and compositions, including formulations and pharmaceutical compositions, for use in in vivo, in vitro or ex vivo methods for catalyzing the hydrolysis of organophosphate (OP)-inhibited human acetylcholinesterase (hAChE) in the central nerve system (CNS); or, for treating, ameliorating or protecting (preventing) an organophosphate toxicity or poisoning or toxic exposure, or for treating, ameliorating or protecting (preventing) organophosphate inhibition of an acetylcholinesterase (AChE); or, for treating, preventing or ameliorating excessive acetylcholine stimulation in the CNS, or the brain.

In alternative embodiments, the pharmaceutical compositions as provided herein can be administered parenterally, topically, orally or by local administration, such as by aerosol, mist or transdermally. In alternative embodiments, pharmaceutical compositions can be prepared in various forms, such as granules, tablets, pills, capsules, suspensions, taken orally, suppositories and salves, lotions and the like. Pharmaceutical formulations as provided herein may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, geltabs, on patches, in implants, etc. The pharmaceutical compounds can be delivered by transdermally, by a topical route, formulated as applicator sticks, solutions, suspensions, emulsions, gels, creams, ointments, pastes, jellies, paints, powders, mists and aerosols. Oral carriers can be elixirs, syrups, capsules, tablets, pills, geltabs and the like.

In alternative embodiment, compositions as provided herein are delivered orally, e.g., as pharmaceutical formulations for oral administration, and can be formulated using pharmaceutically acceptable carriers well known in the art in appropriate and suitable dosages. Such carriers enable the pharmaceuticals to be formulated in unit dosage forms as tablets, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

In alternative embodiments, liquid carriers are used to manufacture or formulate compounds as provided herein, or a composition used to practice the methods as provided herein, including carriers for preparing solutions, suspensions, emulsions, syrups, elixirs and pressurized compounds. The active ingredient (e.g., a composition as provided herein) can be dissolved or suspended in a pharmaceutically acceptable liquid carrier such as water, an organic solvent, a mixture of both or pharmaceutically acceptable oils or fats. The liquid carrier can comprise other suitable pharmaceutical additives such as solubilizers, emulsifiers, buffers, preservatives, sweeteners, flavoring agents, suspending agents, thickening agents, colors, viscosity regulators, stabilizers or osmo-regulators.

In alternative embodiments, solid carriers are used to manufacture or formulate compounds as provided herein, or a composition used to practice the methods as provided herein, including solid carriers comprising substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. Suitable solid carriers include, for example, calcium phosphate, magnesium stearate, talc, sugars, lactose, dextrin, starch, gelatin, cellulose, polyvinylpyrrolidine, low melting waxes and ion exchange resins. A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

In alternative embodiments, concentrations of therapeutically active compound in a formulation can be from between about 0.1% to about 100% by weight.

In alternative embodiments, therapeutic formulations are prepared by any method well known in the art, e.g., as described by Brunton et al., eds., Goodman and Gilman's: The Pharmacological Bases of Therapeutics, 12th ed., *McGraw-Hill*, 2011; *Remington: The Science and Practice of Pharmacy*, Mack Publishing Co., 20th ed., 2000; Avis et al., eds., Pharmaceutical Dosage Forms: Parenteral Medications, published by Marcel Dekker, Inc., N.Y., 1993; Lieberman et al., eds., Pharmaceutical Dosage Forms: Tablets, published by Marcel Dekker, Inc., N.Y., 1990; and Lieberman et al., eds., Pharmaceutical Dosage Forms: Disperse Systems, published by Marcel Dekker, Inc., N.Y., 1990.

In alternative embodiments, therapeutic formulations are delivered by any effective means appropriated for a particular treatment. For example, depending on the specific anti-tumor agent to be administered, the suitable means include oral, rectal, vaginal, nasal, pulmonary administration, or parenteral (including subcutaneous, intramuscular, intravenous and intradermal) infusion into the bloodstream. For parenteral administration, compounds as provided herein may be formulated in a variety of ways. Aqueous solutions of the modulators can be encapsulated in polymeric beads, liposomes, nanoparticles or other injectable depot formulations known to those of skill in the art. In alternative embodiments, compounds as provided herein are administered encapsulated in liposomes (see below). In alternative embodiments, depending upon solubility, compositions are present both in an aqueous layer and in a lipidic layer, e.g., a liposomic suspension. In alternative embodiments, a hydrophobic layer comprises phospholipids such as lecithin and sphingomyelin, steroids such as cholesterol, more or less ionic surfactants such a diacetylphosphate, stearylamine, or phosphatidic acid, and/or other materials of a hydrophobic nature.

The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of *Remington's Pharmaceutical Sciences*, Maack Publishing Co., Easton Pa. ("*Remington's*"). For example, in alternative embodiments, these compositions as provided herein are formulated in a buffer, in a saline solution, in a powder, an emulsion, in a vesicle, in a liposome, in a nanoparticle, in a nanolipoparticle and the like. In alternative embodiments, the compositions can be formulated in any way and can be applied in a variety of concentrations and forms depending on the desired in vivo, in vitro or ex vivo conditions, a desired in vivo, in vitro or ex vivo method of administration and the like. Details on techniques for in vivo, in vitro or ex vivo formulations and administrations are well described in the scientific and patent literature. Formulations and/or carriers can be in forms such as tablets, pills, powders, capsules, liquids, gels, syrups, slurries, suspensions, etc., suitable for in vivo, in vitro or ex vivo applications.

Compounds (e.g., formulations) as provided herein can comprise a solution of compositions (e.g., apratoxin F and apratoxin G compounds, and/or apratoxin F and apratoxin G stereoisomers, derivatives and analogs) disposed in or dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations are sterile and can be manufactured to be generally free of undesirable matter. In one embodiment, these solutions and formulations are sterilized by conventional, well known sterilization techniques.

The solutions and formulations can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and can be selected primarily based on fluid volumes, viscosities and the like, in accordance with the particular mode of in vivo, in vitro or ex vivo administration selected and the desired results.

The compositions and formulations as provided herein can be delivered by the use of liposomes. In alternative embodiments, by using liposomes, particularly where the liposome surface carries ligands specific for target cells or organs, or are otherwise preferentially directed to a specific tissue or organ type, one can focus the delivery of the active agent into a target cells in an in vivo, in vitro or ex vivo application.

The compositions and formulations as provided herein can be directly administered, e.g., under sterile conditions, to an individual (e.g., a patient) to be treated. The modulators can be administered alone or as the active ingredient of a pharmaceutical composition. Compositions and formulations as provided herein can be combined with or used in association with other therapeutic agents. For example, an individual may be treated concurrently with conventional therapeutic agents.

Nanoparticles, Nanolipoparticles and Liposomes

Also provided are nanoparticles, nanolipoparticles, vesicles and liposomal membranes comprising compounds and compositions used to practice the methods as provided herein, e.g., methods for catalyzing the hydrolysis of organophosphate (OP)-inhibited human acetylcholinesterase (hAChE) in the central nerve system (CNS); or, for treating, ameliorating or protecting (preventing) an organophosphate toxicity or poisoning or toxic exposure, or for treating, ameliorating or protecting (preventing) organophosphate inhibition of an acetylcholinesterase (AChE); or, for treating, preventing or ameliorating excessive acetylcholine stimulation in the CNS, or the brain.

Also provided are multilayered liposomes comprising compounds, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition as provided herein.

Liposomes can be made using any method, e.g., as described in Park, et al., U.S. Pat. Pub. No. 20070042031, including method of producing a liposome by encapsulating an active agent as provided herein, the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions comprise a substituted ammonium and/or polyanions, e.g., for targeting delivery of a compound as provided herein to a desired cell type or organ, e.g., brain, as described e.g., in U.S. Pat. Pub. No. 20070110798.

Also provided are nanoparticles comprising compounds as provided herein in the form of active agent-containing nanoparticles (e.g., a secondary nanoparticle), as described, e.g., in U.S. Pat. Pub. No. 20070077286. In one embodiment, provided are nanoparticles comprising a fat-soluble active agent as provided herein or a fat-solubilized water-soluble active agent to act with a bivalent or trivalent metal salt.

In one embodiment, solid lipid suspensions can be used to formulate and to deliver compositions as provided herein to mammalian cells in vivo, in vitro or ex vivo, as described, e.g., in U.S. Pat. Pub. No. 20050136121.

Delivery Vehicles

In alternative embodiments, any delivery vehicle can be used to practice the methods or used, e.g., to deliver compositions as provided herein to mammalian cells in vivo, in vitro or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition as provided herein, e.g. as described, e.g., in U.S. Pat. Pub. No. 20040151766.

In one embodiment, a composition can be applied to cells using vehicles with cell membrane-permeant peptide conjugates, e.g., as described in U.S. Pat. Nos. 7,306,783; 6,589,503. In one aspect, the composition to be delivered is conjugated to a cell membrane-permeant peptide. In one embodiment, the composition to be delivered and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver the composition to a cell, e.g., using any electroporation system as described e.g. in U.S. Pat. Nos. 7,109,034; 6,261,815; 5,874,268.

Dosaging

The pharmaceutical compositions and formulations as provided herein can be administered for prophylactic and/or therapeutic treatments. In therapeutic applications, compositions are administered to a subject already exposed to a toxin, or exposed to any agent or chemical causing or resulting in excessive acetylcholine stimulation in the brain, e.g., exposure to a drug, a drug overdose, or a poisoning or a toxic exposure to a drug, and optionally the drug overdose causing the excessive acetylcholine stimulation is caused at least in part by: physostigmine, neostigmine, pyridostigmine, diisopropylfluorophosphate, or echothiophate an amount sufficient to cure, alleviate or partially arrest the clinical manifestations of the agent and/or its complications (a "therapeutically effective amount").

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest *Remington's*, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods as provided herein are correct and appropriate.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Example 1: Uncharged Bis-Oximes for Accelerated Reactivation Of OP-Conjugated Human Acetylcholinesterase This example demonstrates that methods and compositions as provided herein using the exemplary embodiment are effective and can be used as antidotes against OP intoxication in nerve agent or OP pesticide exposure. Seven bis-oximes antidotes were identified, including—in order of their in vivo potency: LG-829 greater than LG-823 greater than LG-804 greater than LG-703 greater than RS194B greater than LG-750 greater than LG-747 greater than LG-700.

We have analyzed molecular interactions of oxime RS194B (see, e.g., US/2019/0119237 A1) with native and VX-inhibited hAChE by resolving respective human AChE (hAChE) X-ray structures in a way similar to previously used for *Torpedo californica* AChE [1-4]. Surprisingly, in both complexes orientation of the nucleophilically reactive oximate of RS194B was found pointing away from the conjugated phosphorus, its intended reactivation target. We have used those two structures as molecular templates to design and test, first in silico, a small library of bis-oximes intended to remedy an oxime orientation problem. Computational docking and analysis was used to select best bis-oximes for synthesis and subsequent functional in vitro testing.

We synthesized in 20 to 150 mg quantities seven bis-oxime derivatives of piperidines, piperazines and homopiperazines and discovered that their efficacies for in vitro reactivation of sarin-, cyclosarin-, VX- and paraoxon-inhibited human AChE exceed the one found for RS194B. By structural analysis, using X-ray diffraction we determined improved, productive orientation of the enhanced bis-oxime reactivator, consistent with its enhanced efficacy. The novel bis-oxime library of uncharged heterocyclic antidotes was used to create novel accelerated centrally active antidote against OP intoxication.

Materials and Methods

*Protein expression and purification.* Monomeric form of human AChE truncated at C-terminal amino acid position 547 was expressed and purified as described before, i.e., in monomeric form truncated at 547 and with FLAG tag placed at the N terminal end [5].

Crystallization. In preparation for crystallization samples of hAChE were dialyzed in 10 mM NaCl, 10 mM HEPES, pH 7, and concentrated to 6-10 mg/mL. About 1 hour prior to crystallization, the solution of hAChE was combined with stock solutions of ligands in a molar ratio of 1:5 or 1:10 to obtain binary complexes. Crystals were grown by vapor diffusion at 10° C. in sitting drop microbridges or 9-well glass plates (Hampton Research, Aliso Viejo, Calif.). Well solutions containing 10 mM sodium citrate, 100 mM HEPES, pH 7.5, 7-12% PEG6000 were used in crystallization experiments with RS194B and LG-703 and 200 mM potassium nitrate, 100 mM HEPES pH 7.5, 9% PEG 3350 were used to produce crystals with x. Non-hazardous analogue of VX (Amitai et al., Gerlits et al.) was soaked into crystals of the binary complex of RS194B with hAChE.

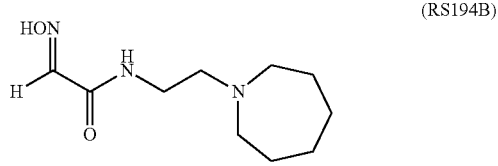
(RS194B)

X-Ray Data Collection

X-ray crystallographic data were collected at room temperature (approximately 20° C.) and from frozen crystals at 100 K. Prior to data collection at 100 K crystals were subjected to two very brief consecutive soaks in the cryoprotectant solutions, first in 12% glycerol followed by 25% glycerol, and then flash cooled by plunging into liquid nitrogen. For the RT data collection, crystals were mounted on the Litholoops (Molecular Dimensions, Maumee, Ohio) directly from the crystallization or soaking drops and kept hydrated using the MiTeGen (Ithaca, N.Y.) room temperature setup. Diffraction data were collected on the ID19 (100 K) and BM19 (293K) beamlines at SBC-CAT using a Pilatus3 X 6M (ID19) and MAR CCD 165 mm (BM19) detectors at the Advanced Photon Source (APS). X-ray diffraction data were integrated and scaled using the HKL3000 software suite [6].

The structures were solved by molecular replacement using the CCP4 suite [7]. The structure of the apo-hAChE (PDB ID 4EY4) [8] was used as a starting model with all waters and the N-linked glycosylated saccharides removed. Refinement was performed using the phenix.refine program in the PHENIX [9] suite and the resulting structure analyzed with molprobity [10]. The structures were built and manipulated with program Coot [11]. Figures were generated using Coot, Biovia Discovery Visualizer (Dassault Systems) and PyMol molecular graphics software (Schrödinger LLC). A summary of the crystallographic data and refinement is given in Table 1.

TABLE 1

X-ray crystallographic data collection and refinement statistics.

| | LT | | |
|---|---|---|---|
| | hAChE:RS194B | VX-hAChE:RS194B | hAChE:LG-703 |
| Data collection | | | |
| Space group | | $P3_1$ | |
| Cell dimensions: | | | |
| a, b, c (Å) | 125.0, 125.0, 129.8 | 124.4, 124.4, 129.1 | 125.4, 125.4, 129.8 |
| α, β, γ (°) | | 90, 90, 120 | |
| Resolution (Å) | 40.00-2.40 (2.49-2.40)* | 40.00-2.25 (2.33-2.25) | 40.00-3.00 (3.11-3.00) |
| $R_{merge}$ | 0.034 (0.522) | 0.063 (0.594) | 0.160 (0.561) |
| I/σI | 11.3 (1.5) | 9.6 (1.2) | 4.3 (1.3) |
| Completeness (%) | 94.1 (94.1) | 92.2 (91.4) | 96.7 (94.4) |
| Redundancy | 1.8 (1.7) | 1.9 (1.8) | 2.6 (2.4) |
| Refinement | | | |
| No. reflections | 76164 | 88333 | 38127 |
| Resolution (Å) | 39.02-2.41 | 38.82-2.26 | 39.14-3.00 |
| Rwork/Rfree | 0.206/0.229 | 0.207/0.229 | 0.205/0.253 |
| No. atoms (non-H) | 8686 | 8830 | 8473 |
| Water | 242 | 366 | 70 |
| R.m.s.d. | | | |
| Bonds (Å) | 0.002 | 0.002 | 0.002 |
| Bond angles (°) | 0.521 | 0.475 | 0.484 |
| PDB ID | | | |

Computational molecular modelling. Seventeen hypothetical uncharged bis-oxime compounds were generated in silico and evaluated computationally as potential reactivators of VX-hAChE conjugate. As a starting point x-ray structure of RS194B*VX-hAChE ternary complex was used where molecule of RS194B was replaced by candidate bis-oxime.

Synthetic procedures. RS194B was prepared as described before [12]. Seven novel bis-oxime acetamides were prepared and characterized:

1. General Synthetic Methods

The column chromatography was performed using silica gel 60 at increased pressure. The analytical thin-layer chromatography was carried out using plates coated with silica gel 60 with a fluorescent indicator F254. Thin-layer chromatography plates were visualized by exposure to ultraviolet light (254 nm) or by detection reagents potassium permanganate. NMR spectra were all recorded on a Bruker NMR (600 megaHz). Chemical shifts are reported in δ ppm referenced to an internal $SiMe_4$ standard for $^1H$ NMR and chloroform-d($CHCl_3$-$d_1$; 7.26 (D); 77.16 (C) ppm), or hexadeuteriodimethylsulfoxide (DMSO-$d_6$; 2.50 (D), 39.7 (C) ppm). Chemicals were purchased from Sigma-Aldrich Co and were used without additional purification. Electric microwave was used for microwave irradiation. The final compounds were analyzed by LC-MS consisting of UHLPC to obtain high resolution mass spectra. Gradient LC analysis confirmed greater than 95% purity.

2. Synthesis of Novel Compounds

2.1 Preparation of Oxime Fragment

Ethyl (2E)-2-(hydroxyimino)acetate (x): Hydroxylamine hydrochloride ($NH_2OH·HCl$) (1.0 eq; 50.44 mmol) was dissolved in acetonitrile/water (9:1 ratio=36:4 mL) and ethyl glyoxalate (50% solution in toluene) (1.0 eq; 50.44 mmol) was slowly added. After 10 min of stirring triethylamine (TEA) (1.0 eq; 50.44 mmol) was drop wise introduced over 30 min. The reaction mixture was stirred at room temperature (RT) for 24 hours. Then it was concentrated and diluted with $H_2O$. The aqueous solution was three times washed with dichloromethane (DCM) 3×100 mL and the organic phases were collected, dried over anhydrous sodium sulfate ($Na_2SO_4$), filtrated and concentrated to give crude product as colorless oil. Yield 61%.

$^1H$ NMR (600 MHz, DMSO-$d_6$) δ12.56 (s, 1H), 7.54 (s, 1H), 4.19 (q, J=7.1 Hz, 2H), 1.23 (t, J=7.1 Hz, 3H).

2.2 General Procedure a for N-Alkylation with 2-Chloroacetonitrile

-continued x n = 1; 59%
y n = 2; 81%

Piperazine or homopiperazine (1.0 eq); 2-chloroacetonitrile (2.4 eq) and $Na_2CO_3$ (4.0 eq) were dissolved in absolute EtOH. The reaction mixture was challenged by microwave (MW) irradiation for 5 hours at 100° C. The solid was filtered and the filtrate was purified by column chromatography using mobile phase DCM and methanol (MeOH).

2-[4-(cyanomethyl)piperazin-1-yl]acetonitrile: Prepared according to the general method A. Piperazine (538 mg; 6.246 mmol); 2-chloroacetonitrile (950 μL; 14.99 mmol); $Na_2CO_3$ (2.648 g; 24.98 mmol) and EtOH (4 mL). Purification was performed using mobile phase DCM:MeOH (98:2) to give crude product x as yellow oil. Yield 59%.

$^1H$ NMR (600 MHz, Chloroform-d) δ3.55 (s, 4H), 2.67 (s, 8H). $^{13}C$ NMR (151 MHz, $CDCl_3$) δ114.62, 51.36, 46.03.

2-[4-(cyanomethyl)-1,4-diazepan-1-yl]acetonitrile: Prepared according to the general method A. Homopiperazine (638 mg; 6.37 mmol); 2-chloroacetonitrile (970 μL; 15.29 mmol); $Na_2CO_3$ (2.701 g; 25.48 mmol) and EtOH (4 mL). Purification was performed using mobile phase DCM: MeOH (98:2) to give crude product y as yellow oil. Yield 81%.

$^1H$ NMR (600 MHz, Chloroform-d) δ3.58 (s, 4H), 2.88-2.74 (m, 8H), 1.96-1.86 (m, 2H). $^{13}C$ NMR (151 MHz, $CDCl_3$) δ115.78, 54.39, 53.47, 47.34, 27.86.

2.3 the N-Alkylation with 3-Bromopropionitrile Using TEA in DCM

3-[4-(cyanomethyl)piperazin-1-yl]propanenitrile: The compound xy (974 mg; 7.78 mmol) was dissolved in anhydrous DCM (15 mL) and 3-bromopropionitrile (645 μL; 7.78 mmol) was added. After 10 min of stirring, TEA (2.17 mL; 15.56 mmol) was drop wise introduced. The reaction mixture was stirred at RT for 24 hours. The solution was diluted with $H_2O$, the organic phase was removed and water phase was washed three times with additional DCM (3×50 mL). The organic phases were collected, dried over $Na_2SO_4$, filtered, concentrated and purified by column chromatography using mobile phase DCM/MeOH (14:1) to give crude product yz as dark yellow oil. Yield 66%.

$^1H$ NMR (600 MHz, Chloroform-d) δ3.52 (s, 2H), 2.72 (t, J=7.0 Hz, 2H), 2.69-2.55 (m, 8H), 2.52 (t, J=7.0 Hz, 2H). $^{13}C$ NMR (151 MHz, $CDCl_3$) δ118.62, 114.62, 53.08, 52.12, 51.56, 45.82, 15.99.

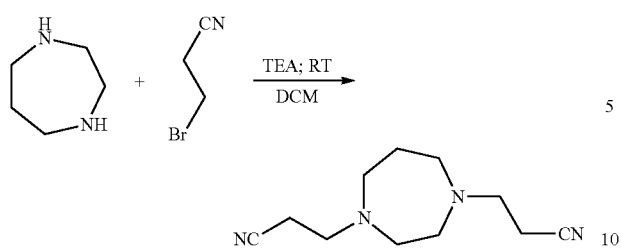

3-[4-(2-cyanoethyl)-1,4-diazepan-1-yl]propanenitrile:
Homopiperazine (1.803 mg; 18.0 mmol) was dissolved in anhydrous DCM (20 mL) and 3-bromopropionitrile (2.986 mL; 36.0 mmol) was added. After 10 min of stirring, TEA (10.0 mL; 72.0 mmol) was drop wise introduced. The reaction mixture was stirred at RT for 24 hours. The solution was diluted with H$_2$O, the organic phase was removed and water phase was washed three times with additional DCM (3×50 mL). The organic phases were collected, dried over Na$_2$SO$_4$, filtered, concentrated and purified by column chromatography using mobile phase DCM/MeOH (9:1) to give crude product yz as dark yellow oil. Yield 84%.

$^1$H NMR (600 MHz, Chloroform-d) δ2.87 (t, J=6.9 Hz, 4H), 2.80-2.71 (m, 8H), 2.47 (t, J=6.9 Hz, 4H), 1.80 (p, J=6.9, 5.3 Hz, 2H). $^{13}$C NMR (151 MHz, CDCl$_3$) δ119.01, 54.74, 53.38, 53.31, 27.98, 16.47.

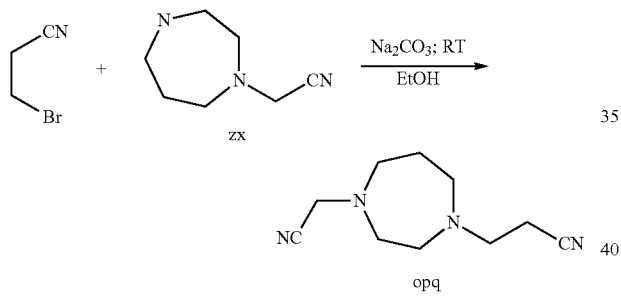

3-[4-(cyanomethyl)-1,4-diazepan-1-yl]propanenitrile:
The compound zx (1.229 g; 8.83 mmol) was dissolved in absolute EtOH (20 mL) and subsequently 3-bromopropionitrile (1.5 mL; 17.66 mmol) and Na$_2$CO$_3$ (2.808 g; 26.5 mmol) were added. The reaction mixture was stirred at RT for 24 hours, concentrated and directly purified using DCM alone as mobile phase to give crude product opq as yellow oil. Yield 53%.

$^1$H NMR (600 MHz, Chloroform-d) δ3.55 (s, 2H), 2.87 (t, J=7.0 Hz, 2H), 2.81-2.73 (m, 8H), 2.46 (t, J=7.0 Hz, 2H), 1.83 (p, J=7.0, 5.9 Hz, 2H). $^{13}$C NMR (151 MHz, CDCl$_3$) δ118.91, 115.69, 54.75, 54.06, 53.56, 53.32, 47.09, 27.77, 16.42.

2.4 Multistep Reactions

2.4.1 General Procedure B

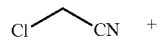

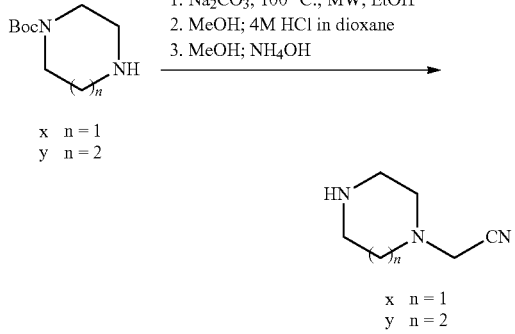

N-Boc-piperazine or N-Boc-homopiperazine (1.0 eq) was dissolved in absolute EtOH and subsequently 2-chloroacetonitrile (1.2 eq) and Na$_2$CO$_3$ (2.0 eq) were added. The reaction mixture was challenged by MW irradiation for 5 hours at 100° C. The solution was concentrated, diluted with H$_2$O and three times washed with DCM (3×50 mL). The organic phases were collected, dried over Na$_2$SO$_4$, filtered, concentrated and used into next step without any further purification.

The residue was dissolved in MeOH (30 mL) and 1 M solution of HCl in dioxane (15 mL) was added. The mixture was stirred at RT for 20 hours. The result was concentrated and dried under reduced pressure. The residue was again dissolved in MeOH (30 mL) and 25% solution of ammonium hydroxide (NH$_4$OH) in water (15 mL) was added. After another 1 hour of stirring the reaction mixture was concentrated and directly purified by column chromatography using mobile phase DCM/MeOH/NH$_4$OH (6:1:0.1) to give crude products.

2-(piperazin-1-yl)acetonitrile: Prepared according to the general method B. N-Boc-piperazine (2.012 g; 10.8 mmol); 2-chloroacetonitrile (820 μL; 13.0 mmol); Na$_2$CO$_3$ (2.289 g; 21.6 mmol) and EtOH (10 mL). Yield 72%.

$^1$H NMR (600 MHz, Chloroform-d) δ3.50 (s, 2H), 2.93 (t, J=4.9 Hz, 4H), 2.55 (t, J=4.9 Hz, 4H), 1.74 (bs, 1H). $^{13}$C NMR (151 MHz, CDCl$_3$) δ114.66, 52.93, 46.56, 45.54.

2-(1,4-diazepan-1-yl)acetonitrile: Prepared according to the general method B. N-Boc-homopiperazine (2.354 g; 11.75 mmol); 2-chloroacetonitrile (1.8 mL; 14.1 mmol); Na$_2$CO$_3$ (2.475 g; 23.5 mmol) and EtOH (10 mL). Yield 86%.

$^1$H NMR (600 MHz, Chloroform-d) δ3.60 (s, 2H), 3.19 (bs, 1H), 3.07-2.97 (m, 4H), 2.84-2.76 (m, 4H), 1.88 (p, J=5.9 Hz, 2H). $^{13}$C NMR (151 MHz, CDCl$_3$) δ115.59, 56.26, 53.89, 47.88, 47.45, 46.86, 29.20.

2.4.2 General Procedure C

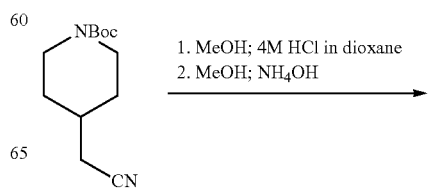

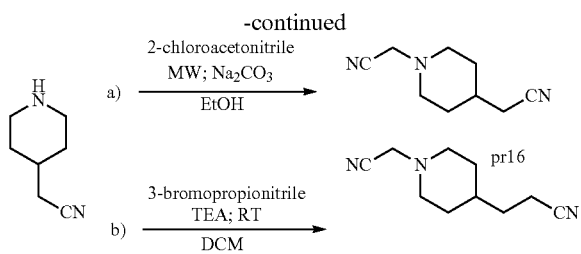

2.5 General Procedure D for Reduction of Carbonitrile Groups Using LiAlH₄

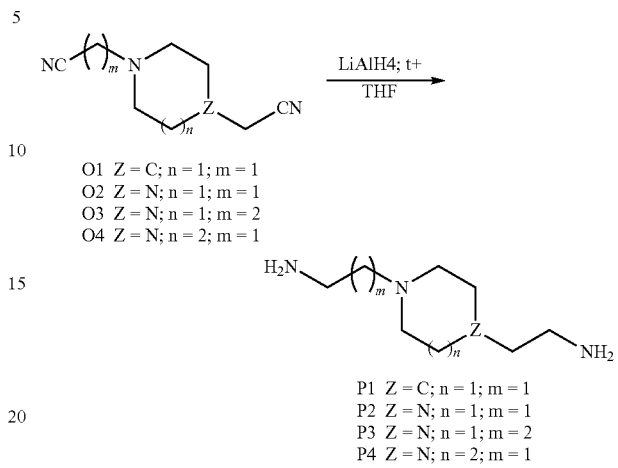

The N-Boc-4-cyanomethylpiperidine (4.118 g; 18.36 mmol) was dissolved in MeOH (20 mL) and 1 M solution of HCl in dioxane (10 mL) was added. The mixture was stirred at RT for 20 hours. The result was concentrated and dried under reduced pressure. The residue was again dissolved in MeOH (20 mL) and 25% solution of ammonium hydroxide (NH₄OH) in water (10 mL) was added. After another 1 hour of stirring the reaction mixture was concentrated and directly purified using very fast column chromatography with mobile phase DCM/MeOH/NH₄OH (6:1:0.1) to give crude product 4-cyanomethylpiperidine as white solid. Yield greater than 99%. The amount of 4-cyanomethylpiperidine was halved and used in the next step without characterization.

a) 2-[1-(cyanomethyl)piperidin-4-yl]acetonitrile: 4-cyanomethylpiperidine (1.14 g; 9.18 mmol) was dissolved in absolute EtOH (10 mL) and subsequently 2-chloroacetonitrile (700 μL; 11.0 mmol) and Na₂CO₃ (1.946 g; 18.36 mmol) were added. The reaction mixture was challenged by MW irradiation for 10 hours at 100° C. The result was concentrated and directly purified using column chromatography with mobile phase DCM/MeOH (95:5) to give crude product as yellowish solid. Yield 62% after 2 steps.

$^1$H NMR (599 MHz, Chloroform-d) δ3.68 (s, 2H), 3.03-2.94 (m, 2H), 2.54-2.49 (m, 2H), 2.47 (d, J=6.8 Hz, 2H), 2.06-1.97 (m, 2H), 1.91-1.81 (m, 1H), 1.65-1.54 (m, 2H). $^{13}$C NMR (151 MHz, CDCl₃) δ118.16, 114.60, 51.64, 46.22, 32.04, 31.09, 23.83.

b) 3-[4-(cyanomethyl)piperidin-1-yl]propanenitrile: 4-cyanomethylpiperidine (1.14 g; 9.18 mmol) was dissolved in anhydrous DCM (25 mL) and 3-bromopropionitrile (913 μL; 11.0 mmol) was added. After 10 min of stirring, TEA (2.6 mL; 18.36 mmol) was drop wise introduced. The reaction mixture was stirred at RT for 24 hours. The solution was diluted with H₂O, the organic phase was removed and water phase was washed three times with additional DCM (3×30 mL). The organic phases were collected, dried over Na₂SO₄, filtered, concentrated and purified by column chromatography using mobile phase DCM/MeOH (95:5) to give the title compound as yellow oil. Yield 79% after two steps.

$^1$H NMR (599 MHz, Chloroform-d) δ3.08-2.99 (m, 2H), 2.80 (t, J=7.1 Hz, 2H), 2.62 (t, J=7.0 Hz, 2H), 2.42 (d, J=7.0 Hz, 2H), 2.27-2.16 (m, 2H), 1.99-1.89 (m, 2H), 1.86-1.73 (m, 1H), 1.61-1.45 (m, 2H). $^{13}$C NMR (151 MHz, CDCl₃) δ118.89, 118.44, 53.34, 52.59, 32.87, 31.37, 23.88, 15.96.

The 4 M solution of LiAlH₄ in Et₂O (4.6 eq) was added into anhydrous THF under N₂ atmosphere. The compound O1-O4 (1.0 eq) was dissolved in anhydrous THF (20 mL) and the solution was drop wise introduced in the solution of LiAlH₄. The reaction mixture was heated to 90° C. for 4 hours. The result was cooled to 0° C. and slowly neutralized by H₂O and then by 10% solution of NaOH. The solid was filtered and the filtrate was directly purified by column chromatography using mobile phase DCM/MeOH/NH₄OH (6:3:1) to give crude product P1-P4.

2-[4-(2-aminoethyl)piperazin-1-yl]ethan-1-amine: Prepared according to the general method D. The compound O1 (585 mg; 3.56 mmol); LiAlH₄ (4 M in Et₂O) (4.1 mL; 16.4 mmol). Neutralization 1 mL H₂O and 3 mL of 10% NaOH. Yield greater than 99% as dark yellow oil.

$^1$H NMR (600 MHz, Chloroform-d) δ2.78 (t, J=6.2 Hz, 8H), 2.48 (bs, 4H), 2.41 (t, J=6.2 Hz, 8H). $^{13}$C NMR (151 MHz, CDCl₃) δ61.34, 53.49, 38.97. 3-[4-(2-aminoethyl)piperazin-1-yl]propan-1-amine: Prepared according to the general method D. The compound O3 (921 mg; 5.17 mmol); LiAlH₄ (4 M in Et₂O) (6.5 mL; 25.85 mmol). Neutralization 2 mL H₂O and 4.5 mL of 10% NaOH. Yield 61% as dark yellow oil.

$^1$H NMR (600 MHz, Chloroform-d) δ2.88 (t, J=4.9 Hz, 2H), 2.81-2.71 (m, 4H), 2.52-2.34 (m, 10H), 1.66-1.61 (m, 2H). $^{13}$C NMR (151 MHz, CDCl₃) δ61.77, 61.15, 56.52, 46.10, 40.84, 38.79, 30.43.

2-[4-(2-aminoethyl)-1,4-diazepan-1-yl]ethan-1-amine: Prepared according to the general method D. The compound O2 (785 mg; 4.4 mmol); LiAlH₄ (4 M in Et₂O) (5.0 mL; 20.26 mmol). Neutralization 1 mL H₂O and 4 mL of 10% NaOH. Yield 84% as dark yellow oil.

$^1$H NMR (600 MHz, Chloroform-d) δ2.75-2.71 (m, 4H), 2.70-2.64 (m, 8H), 2.55-2.51 (m, 4H), 1.80-1.74 (m, 2H). $^{13}$C NMR (151 MHz, CDCl₃) δ60.83, 55.42, 54.38, 39.58, 27.81.

2-[1-(2-aminoethyl)piperidin-4-yl]ethan-1-amine: Prepared according to the general method D. The compound O4 (684 mg; 4.19 mmol); LiAlH₄ (4 M in Et₂O) (4.8 mL; 19.3 mmol). Neutralization 1 mL H₂O and 4 mL of 10% NaOH. Yield greater than 99% as dark yellow oil. $^1$H NMR (599 MHz, DMSO-d₆) δ2.91 (dt, J=11.7, 3.4 Hz, 2H), 2.71 (t, J=6.6 Hz, 2H), 2.69-2.63 (m, 2H), 2.38 (t, J=6.6 Hz, 2H), 1.97 (td, J=11.7, 2.5 Hz, 2H), 1.75-1.67 (m, 2H), 1.45-1.35 (m, 3H), 1.28-1.17 (m, 2H).

2.6 General Procedure E for Reduction of Carbonitrile Groups Using Raney-Nickel

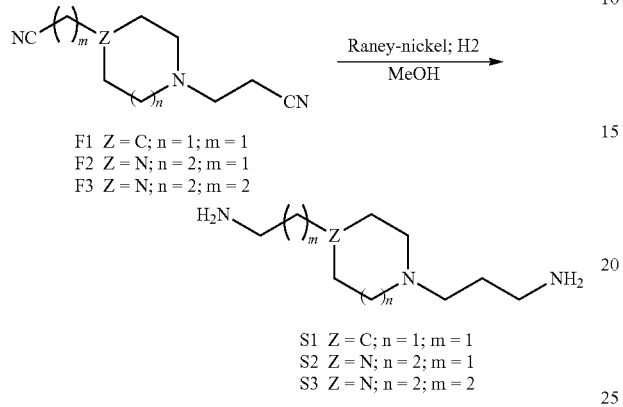

F1 Z = C; n = 1; m = 1
F2 Z = N; n = 2; m = 1
F3 Z = N; n = 2; m = 2

S1 Z = C; n = 1; m = 1
S2 Z = N; n = 2; m = 1
S3 Z = N; n = 2; m = 2

The compound F1-F3 (1.0 eq) was dissolved in anhydrous MeOH under $N_2$ atmosphere and Raney-nickel (10.0 eq) was added. The $N_2$ atmosphere was 5 times evacuated and replaced then $N_2$ was switched to $H_2$ again 5 times was evacuated and replaced. The reaction mixture was stirred under $H_2$ atmosphere and controlled by TLC. After finishing the solid was carefully filtered and the filtrate was directly purified by column chromatography using mobile phase DCM/MeOH/NH$_4$OH (6:3:1) to give crude product S1-S3.

3-[4-(2-aminoethyl)-1,4-diazepan-1-yl]propan-1-amine: Prepared according to the general method E. The compound F2 (831 mg; 4.32 mmol); Raney-nickel (2800, slurry, in H$_2$O) (2.536 g; 43.2 mmol); MeOH 25 mL. Yield 44% of impure product as dark yellow oil.

3-[4-(3-aminopropyl)-1,4-diazepan-1-yl]propan-1-amine: Prepared according to the general method E. The compound F3 (1.417 g; 6.87 mmol); Raney-nickel (2800, slurry, in H$_2$O) (4.03 g; 68.7 mmol); MeOH 50 mL. Yield 92% as dark yellow oil.

$^1$H NMR (599 MHz, Chloroform-d) δ2.85 (t, J=6.8 Hz, 4H), 2.82-2.77 (m, 8H), 2.67-2.59 (m, 4H), 1.95-1.86 (m, 2H), 1.74 (p, J=7.0 Hz, 4H) $^{13}$C NMR (151 MHz, CDCl$_3$) δ56.19, 54.97, 54.35, 40.62, 30.98, 27.19.

3-[4-(2-aminoethyl)piperidin-1-yl]propan-1-amine: Prepared according to the general method E. The compound F1 (1.094 g; 6.17 mmol); Raney-nickel (2800, slurry, in H$_2$O) (3.621 g; 61.7 mmol); MeOH 30 mL. Yield 73% as dark yellow oil.

$^1$H NMR (599 MHz, Chloroform-d) δ3.10-2.97 (m, 2H), 2.90-2.68 (m, 4H), 2.53-2.42 (m, 2H), 2.04-1.95 (m, 2H), 1.84-1.58 (m, 8H), 1.57-1.48 (m, 2H), 1.48-1.42 (m, 1H), 1.42-1.32 (m, 2H). $^{13}$C NMR (151 MHz, CDCl$_3$) δ56.83, 54.04, 40.88, 39.56, 32.36, 30.79, 26.53.

2.7 General Procedure F for the Final Step: Bis-Amide Formation

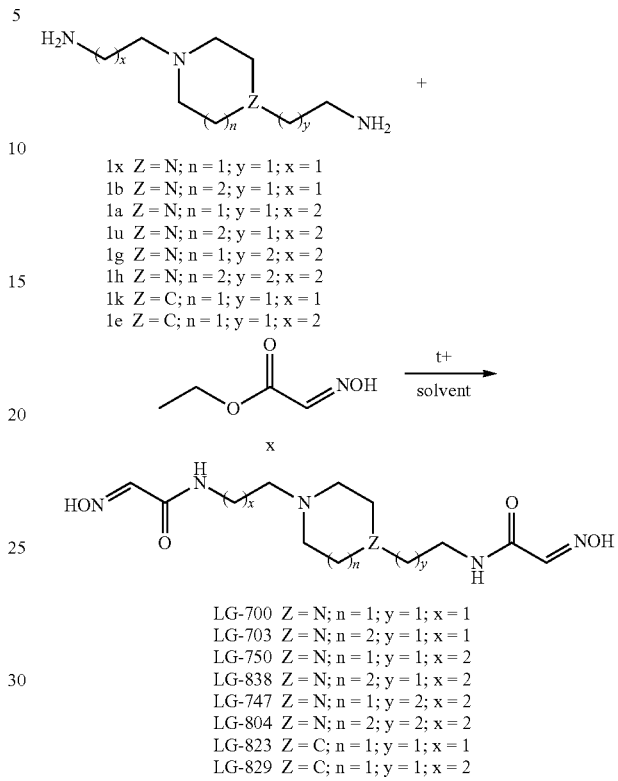

1x Z = N; n = 1; y = 1; x = 1
1b Z = N; n = 2; y = 1; x = 1
1a Z = N; n = 1; y = 1; x = 2
1u Z = N; n = 2; y = 1; x = 2
1g Z = N; n = 1; y = 2; x = 2
1h Z = N; n = 2; y = 2; x = 2
1k Z = C; n = 1; y = 1; x = 1
1e Z = C; n = 1; y = 1; x = 2

LG-700 Z = N; n = 1; y = 1; x = 1
LG-703 Z = N; n = 2; y = 1; x = 1
LG-750 Z = N; n = 1; y = 1; x = 2
LG-838 Z = N; n = 2; y = 1; x = 2
LG-747 Z = N; n = 1; y = 2; x = 2
LG-804 Z = N; n = 2; y = 2; x = 2
LG-823 Z = C; n = 1; y = 1; x = 1
LG-829 Z = C; n = 1; y = 1; x = 2

The compound 1x-1e (1.0 eq) and oxime-fragment x (2.5 eq) was dissolved in solvent (3 mL) and heated for up to several days.

(2E)-2-(N-hydroxyimino)-N-[2-(4-{2-[(2E)-2-(N-hydroxyimino)acetamido]ethyl}piperazin-1-yl)ethyl]acetamide (LG-700): Prepared according general procedure E. Opq (590 mg; 3.425 mmol); oxime fragment x (1.003 g; 8.56 mmol); EtOH (3 mL) heated to 90° C. for 2 days. The solution was concentrated and directly purified by column chromatography using mobile phase DCM/MeOH (4:1). The result was precipitated in cold MeOH and filtered to give crude product LG-700 as white solid. Yield 10%.

$^1$H NMR (600 MHz, DMSO-d$_6$) δ11.94 (s, 2H), 7.95 (t, J=5.8 Hz, 2H), 7.42 (s, 2H), 3.23 (q, J=6.5 Hz, 4H), 2.36 (t, J=6.8 Hz, 12H). $^{13}$C NMR (151 MHz, DMSO) δ162.08, 144.10, 57.09, 53.11, 36.29. HRMS (ESI$^+$): [M]$^+$: calculated for $C_{12}H_{23}N_6O_4^+$ (m/z): 315.1775; detected: 315.1772. LC-MS purity greater than 95%.

(2E)-2-(N-hydroxyimino)-N-[2-(4-{2-[(2E)-2-(N-hydroxyimino)acetamido]ethyl}-1,4-diazepan-1-yl)ethyl]acetamide (LG-703): Prepared according general procedure E. Opq (305 mg; 1.64 mmol); oxime fragment x (480 mg; 4.1 mmol); EtOH (3 mL) heated to 90° C. for 3 days. The solution was concentrated and directly purified by column chromatography using mobile phase DCM/MeOH (2:1). The result was precipitated in cold MeOH and filtered to give crude product LG-703 as white solid. Yield 19%.

$^1$H NMR (600 MHz, DMSO-d$_6$) δ11.95 (s, 2H), 7.93 (t, J=5.7 Hz, 2H), 7.41 (s, 2H), 3.20 (q, J=6.5 Hz, 4H), 2.67-2.56 (m, 8H), 2.52 (t, J=6.8 Hz, 4H), 1.65 (p, J=5.8 Hz, 2H). $^{13}$C NMR (151 MHz, DMSO) δ162.09, 144.12, 56.50, 55.04, 54.01, 37.01, 27.69. HRMS (ESI$^+$): [M]$^+$: calculated for $C_{13}H_{25}N_6O_4^+$ (m/z): 329.1932; detected: 329.1931. LC-MS purity greater than 98%.

(2E)-2-(N-hydroxyimino)-N-[3-(4-{2-[(2E)-2-(N-hydroxyimino)acetamido]ethyl}piperazin-1-yl)propyl]acetamide (LG-750): Prepared according general procedure E. Opq (570 mg; 3.06 mmol); oxime fragment x (896 mg; 7.65 mmol); EtOH (3 mL) heated to 90° C. for 2 days. The solution was concentrated and directly purified by column chromatography using mobile phase DCM/MeOH (2:1). The result was precipitated in cold MeOH and filtered to give crude product LG-750 as white solid. Yield 14%.

$^1$H NMR (600 MHz, DMSO-d$_6$) δ11.96 (s, 1H), 11.91 (s, 1H), 8.22 (t, J=5.8 Hz, 1H), 7.98 (t, J=5.8 Hz, 1H), 7.42 (s, 1H), 7.41 (s, 1H), 3.24 (q, J=6.5 Hz, 2H), 3.14 (q, J=6.5 Hz, 2H), 2.46-2.25 (m, 12H), 1.58 (p, J=7.0 Hz, 2H) $^{13}$C NMR (151 MHz, DMSO) δ162.13, 144.20, 144.08, 56.98, 55.97, 37.53, 36.26, 26.34. HRMS (ESI$^+$): [M]$^+$: calculated for $C_{13}H_{25}N_6O_4^+$ (m/z): 329.1932; detected: 329.1933. LC-MS purity greater than 98%.

(2E)-2-(N-hydroxyimino)-N-[3-(4-{2-[(2E)-2-(N-hydroxyimino)acetamido]ethyl}-1,4-diazepan-1-yl)propyl]acetamide (LG-838): Prepared according general procedure E. Opq (369 mg; 1.84 mmol); oxime fragment x (539 mg; 4.6 mmol); EtOH (3 mL) heated to 90° C. for 5 days. The solution was concentrated and directly purified by column chromatography using mobile phase DCM/MeOH (2:1) to MeOH alone to give impure product LG-838 as orange oil. Yield 5%.

$^1$H NMR (599 MHz, DMSO-d$_6$) δ8.12-7.95 (m, 2H), 7.58-7.38 (m, 2H), 3.34-3.17 (m, 4H), 2.69-2.59 (m, 6H), 2.50 (t, J=7.1 Hz, 2H), 1.75 (p, J=5.7 Hz, 2H), 1.64 (p, J=7.2 Hz, 2H), 1.26-1.15 (m, 2H), 1.13 (t, J=7.1 Hz, 2H) $^{13}$C NMR (151 MHz, DMSO) δ162.16, 162.13, 144.17, 144.06, 56.51, 55.74, 55.13, 54.68, 54.16, 53.96, 37.57, 36.98, 27.39, 27.18. HRMS (ESI$^+$): [M]$^+$: calculated for $C_{14}H_{27}N_6O_4^+$ (m/z): 343.2088; detected: 343.2084. LC-MS purity greater than 87%.

(2E)-2-(N-hydroxyimino)-N-[3-(4-{3-[(2E)-2-(N-hydroxyimino)acetamido]propyl}piperazin-1-yl)propyl]acetamide (LG-747): Prepared according general procedure E. Opq (504 mg; 2.516 mmol); oxime fragment x (737 mg; 6.29 mmol); EtOH (3 mL) heated to 90° C. for 3 days. The solution was concentrated and directly purified by column chromatography using mobile phase DCM/MeOH (2:1). The result was precipitated in cold MeOH and filtered to give crude product LG-747 as white solid. Yield 13%.

$^1$H NMR (600 MHz, DMSO-d$_6$) δ11.89 (s, 2H), 8.19 (s, 2H), 7.40 (s, 2H), 3.14 (q, J=7.0 Hz, 4H), 2.50-2.49 (m, 4H), 2.25 (t, J=7.0 Hz, 8H), 1.57 (p, J=7.0 Hz, 4H). $^{13}$C NMR (151 MHz, DMSO) δ162.10, 144.22, 56.07, 37.61, 26.52. HRMS (ESI$^+$): [M]$^+$: calculated for $C_{14}H_{27}N_6O_4^+$ (m/z): 343.2088; detected: 343.2086. LC-MS purity greater than 97%.

(2E)-2-(N-hydroxyimino)-N-[3-(4-{3-[(2E)-2-(N-hydroxyimino)acetamido]propyl}-1,4-diazepan-1-yl)propyl]acetamide (LG-804): Prepared according general procedure E. Opq (445 mg; 2.076 mmol); oxime fragment x (608 mg; 5.19 mmol); MeCN (3 mL) heated to 50° C. for 2 days. The solution filtered and carefully washed with cold EtOH to give crude product LG-804 as white solid. Yield 9%.

$^1$H NMR (599 MHz, DMSO-d$_6$) δ8.21 (t, J=6.0 Hz, 2H), 7.41 (s, 2H), 3.15 (q, J=6.7 Hz, 4H), 2.60-2.53 (m, 8H), 2.41 (t, J=7.2 Hz, 4H), 1.72-1.62 (m, 2H), 1.60-1.49 (m, 4H). $^{13}$C NMR (151 MHz, DMSO) δ162.10, 144.19, 144.18, 55.80, 55.02, 54.17, 37.60, 27.38, 27.26. HRMS (ESI$^+$): [M]$^+$: calculated for $C_{15}H_{29}N_6O_4^+$ (m/z): 357.2245; detected: 357.2242. LC-MS purity greater than 98%.

(2E)-2-(N-hydroxyimino)-N-[2-(1-{2-[(2E)-2-(N-hydroxyimino)acetamido]ethyl}piperidin-4-yl)ethyl]acetamide (LG-823): Prepared according general procedure E. Opq (694 mg; 4.05 mmol); oxime fragment x (1.186 g; 10.125 mmol); EtOH (3 mL) heated to 90° C. for 1 day. The solution was concentrated and directly purified by column chromatography using mobile phase DCM/MeOH (5:1) to give crude product LG-823 as yellowish solid. Yield 13%.

$^1$H NMR (599 MHz, DMSO-d$_6$) δ12.26 (s, 1H), 12.13 (s, 1H), 8.62 (t, J=5.9 Hz, 1H), 8.43 (t, J=6.0 Hz, 1H), 7.65-7.54 (m, 2H), 3.63 (q, J=6.3 Hz, 2H), 3.51-3.40 (m, 2H), 3.35-3.25 (m, 2H), 3.16-3.06 (m, 2H), 2.91-2.76 (m, 2H), 1.99-1.87 (m, 2H), 1.62-1.48 (m, 5H). $^{13}$C NMR (151 MHz, DMSO) δ162.66, 162.19, 144.14, 143.83, 68.99, 56.20, 52.42, 45.74, 36.21, 34.38, 30.00. HRMS (ESI$^+$): [M]$^+$: calculated for $C_3H_{24}N_5O_4^+$ (m/z): 314.1823; detected: 314.1823. LC-MS purity greater than 95%.

(2E)-2-(N-hydroxyimino)-N-[3-(4-{2-[(2E)-2-(N-hydroxyimino)acetamido]ethyl}piperidin-1-yl)propyl]acetamide (LG-829): Prepared according general procedure E. Opq (406 mg; 2.19 mmol); oxime fragment x (513 mg; 5.475 mmol); EtOH (3 mL) heated to 90° C. for 3 days. The solution was concentrated and directly purified by column chromatography using mobile phase DCM/MeOH (4:1) to give crude product LG-829 as yellowish solid. Yield 17%.

$^1$H NMR (599 MHz, DMSO-d$_6$) δ12.13-11.81 (m, 2H), 8.23 (t, J=5.8 Hz, 1H), 8.13 (t, J=5.9 Hz, 1H), 7.42 (s, 1H), 7.41 (s, 1H), 3.16-3.12 (m, 4H), 2.89-2.75 (m, 2H), 2.27 (t, J=7.1 Hz, 2H), 1.82 (t, J=11.4 Hz, 2H), 1.67-1.51 (m, 4H), 1.36 (q, J=7.1 Hz, 2H), 1.27-1.17 (m, 1H), 1.14-1.10 (m, 2H). $^{13}$C NMR (151 MHz, DMSO) δ162.13, 162.07, 144.19, 144.18, 68.97, 56.40, 56.22, 53.75, 37.68, 36.49, 36.08, 32.01, 30.01, 26.46. HRMS (ESI$^+$): [M]$^+$: calculated for $C_{14}H_{26}N_5O_4^+$ (m/z): 328.1979; detected: 328.1975. LC-MS purity greater than 95%.

Figure 2:
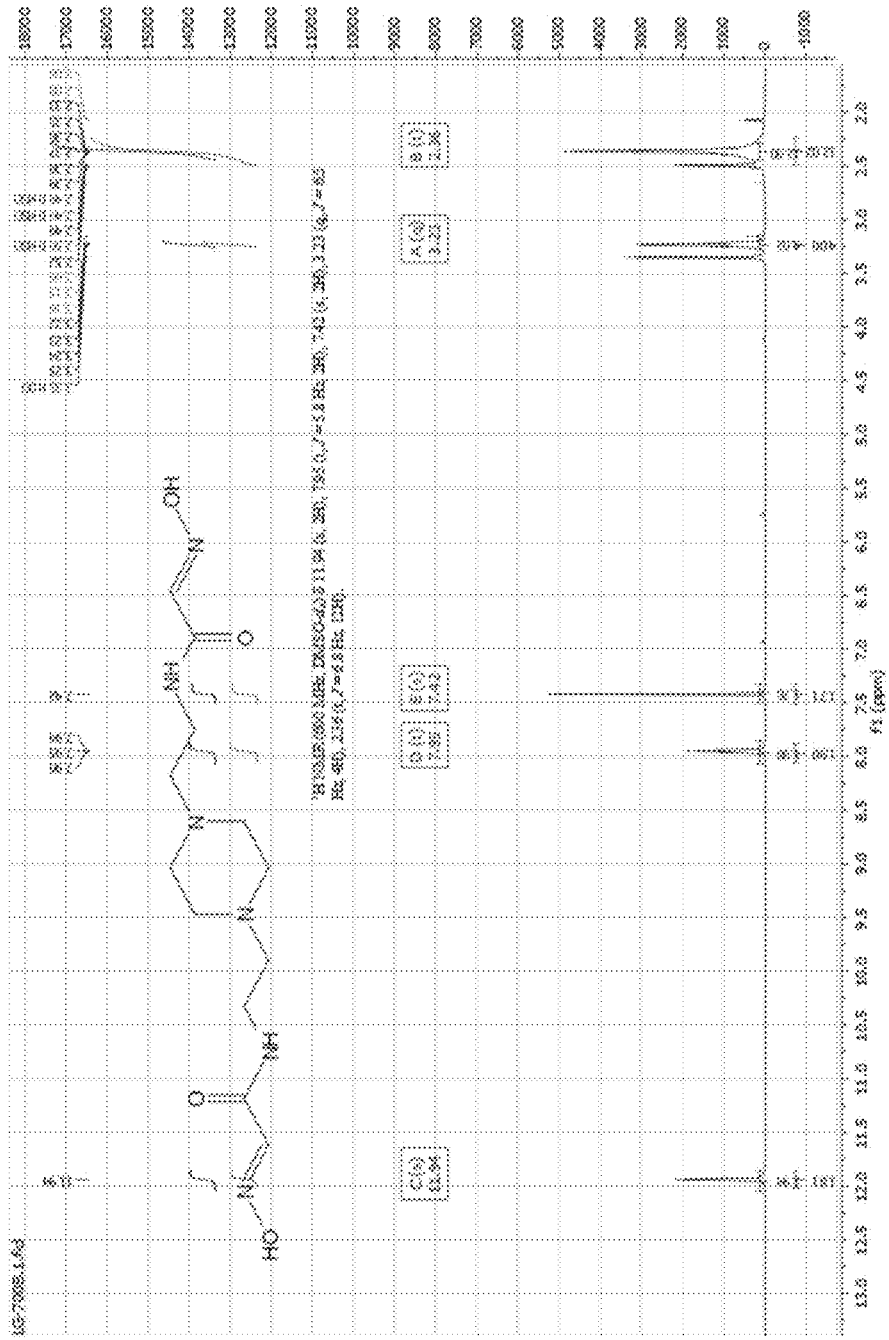
FIG. 2 illustrates a nuclear magnetic resonance (NMR) analysis of (2E)-2-(N-hydroxyimino)-N-[2-(4-{2-[(2E)-2-(N-hydroxyimino)acetamido]ethyl}piperazin-1-yl)ethyl]acetamide (LG-700) $^1$H NMR as described in detail in Example 1, below.

1. NMR; HRMS and HPLC spectrums:

(2E)-2-(N-hydroxyimino)-N-[2-(4-{2-[(2E)-2-(N-hydroxyimino)acetamido]ethyl}piperazin-1-yl)ethyl]acetamide (LG-700) $^1$H NMR: See FIG. 2.

Figure 3:
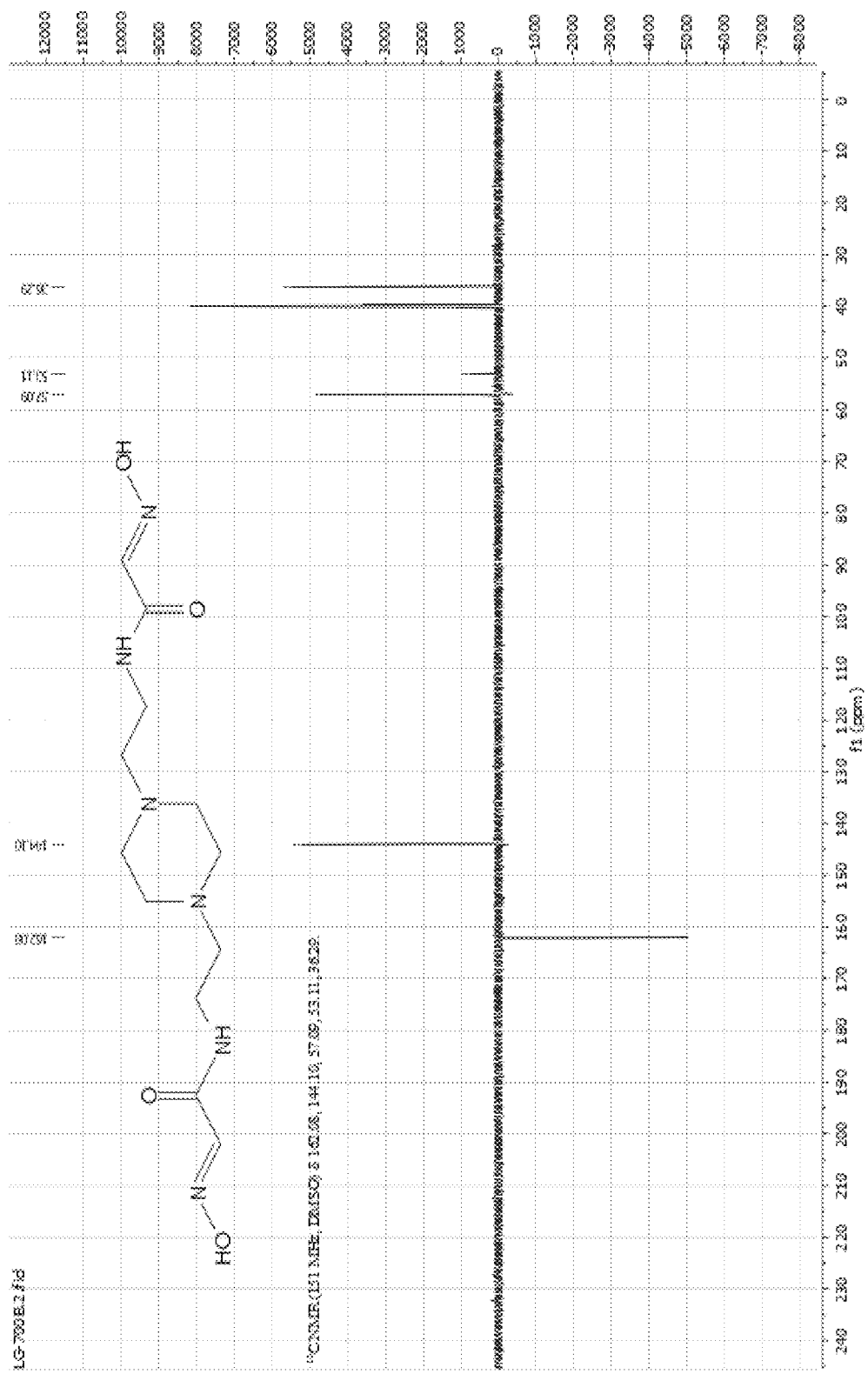
FIG. 3 illustrates an NMR analysis of (2E)-2-(N-hydroxyimino)-N-[2-(4-{2-[(2E)-2-(N-hydroxyimino)acetamido]ethyl}piperazin-1-yl)ethyl]acetamide (LG-700) $^{13}$C NMR as described in detail in Example 1, below.

(2E)-2-(N-hydroxyimino)-N-[2-(4-{2-[(2E)-2-(N-hydroxyimino)acetamido]ethyl}piperazin-1-yl)ethyl]acetamide (LG-700) $^{13}$C NMR: See FIG. 3.

Figure 4:
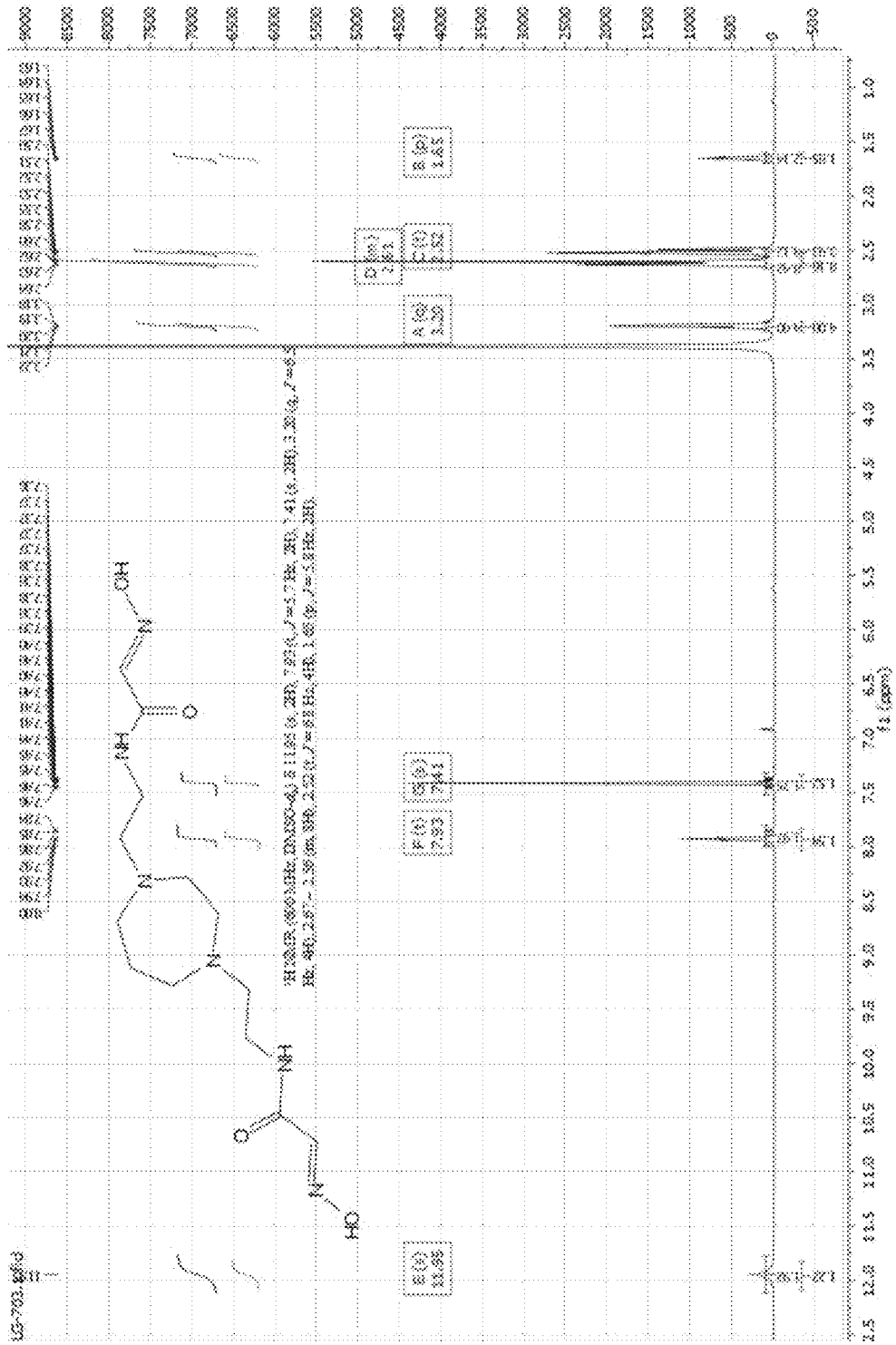
FIG. 4 illustrates an NMR analysis of (2E)-2-(N-hydroxyimino)-N-[2-(4-{2-[(2E)-2-(N-hydroxyimino)acetamido]ethyl}-1,4-diazepan-1-yl)ethyl]acetamide (LG-703) $^1$H NMR as described in detail in Example 1, below.

(2E)-2-(N-hydroxyimino)-N-[2-(4-{2-[(2E)-2-(N-hydroxyimino)acetamido]ethyl}-1,4-diazepan-1-yl)ethyl]acetamide (LG-703) $^1$H NMR: See FIG. 4.

Figure 5:
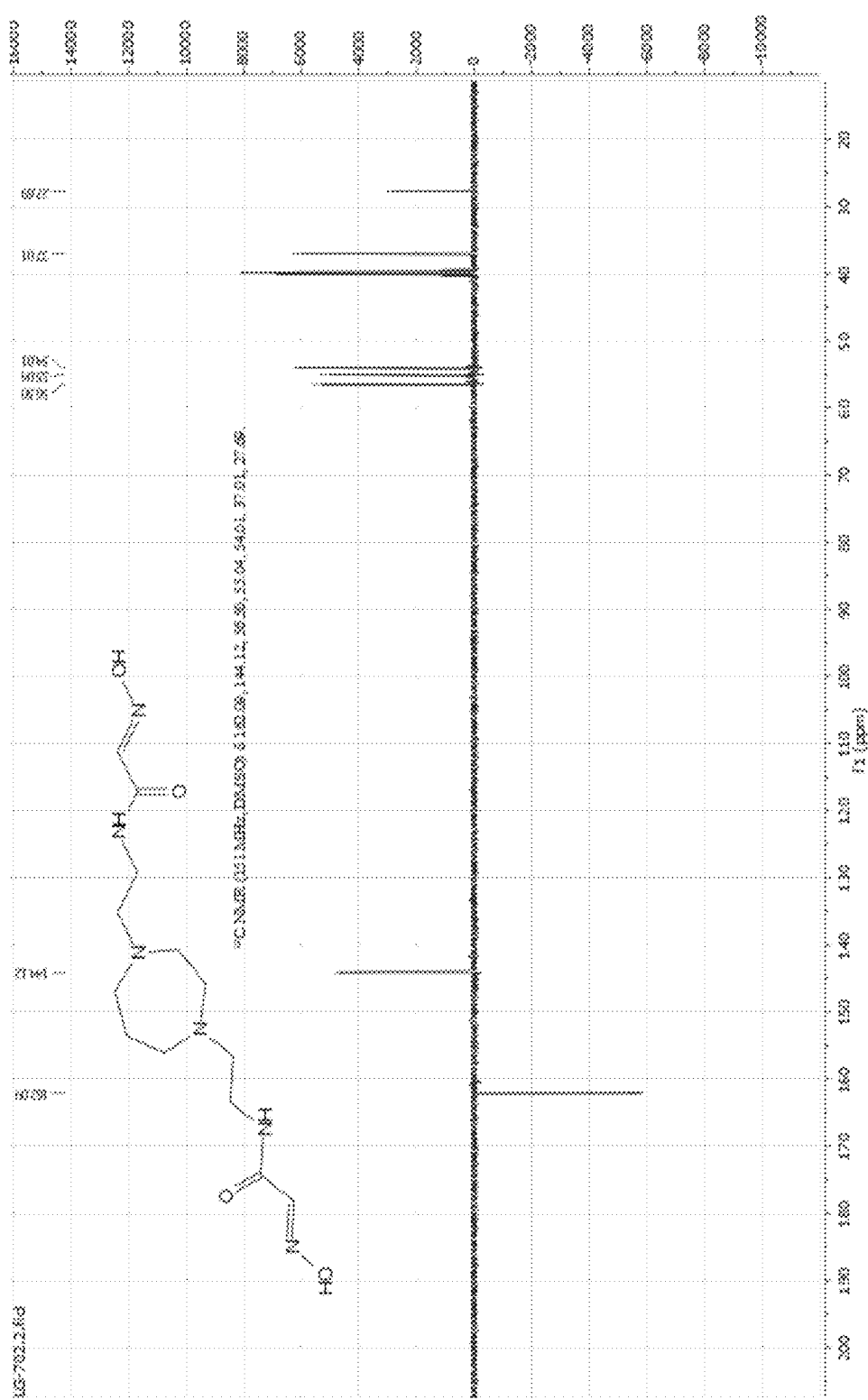
FIG. 5 illustrates an NMR analysis of (2E)-2-(N-hydroxyimino)-N-[2-(4-{2-[(2E)-2-(N-hydroxyimino)acetamido]ethyl}-1,4-diazepan-1-yl)ethyl]acetamide (LG-703) $^{13}$C NMR as described in detail in Example 1, below.

(2E)-2-(N-hydroxyimino)-N-[2-(4-{2-[(2E)-2-(N-hydroxyimino)acetamido]ethyl}-1,4-diazepan-1-yl)ethyl]acetamide (LG-703) $^{13}$C NMR: See FIG. 5.

Figure 6:
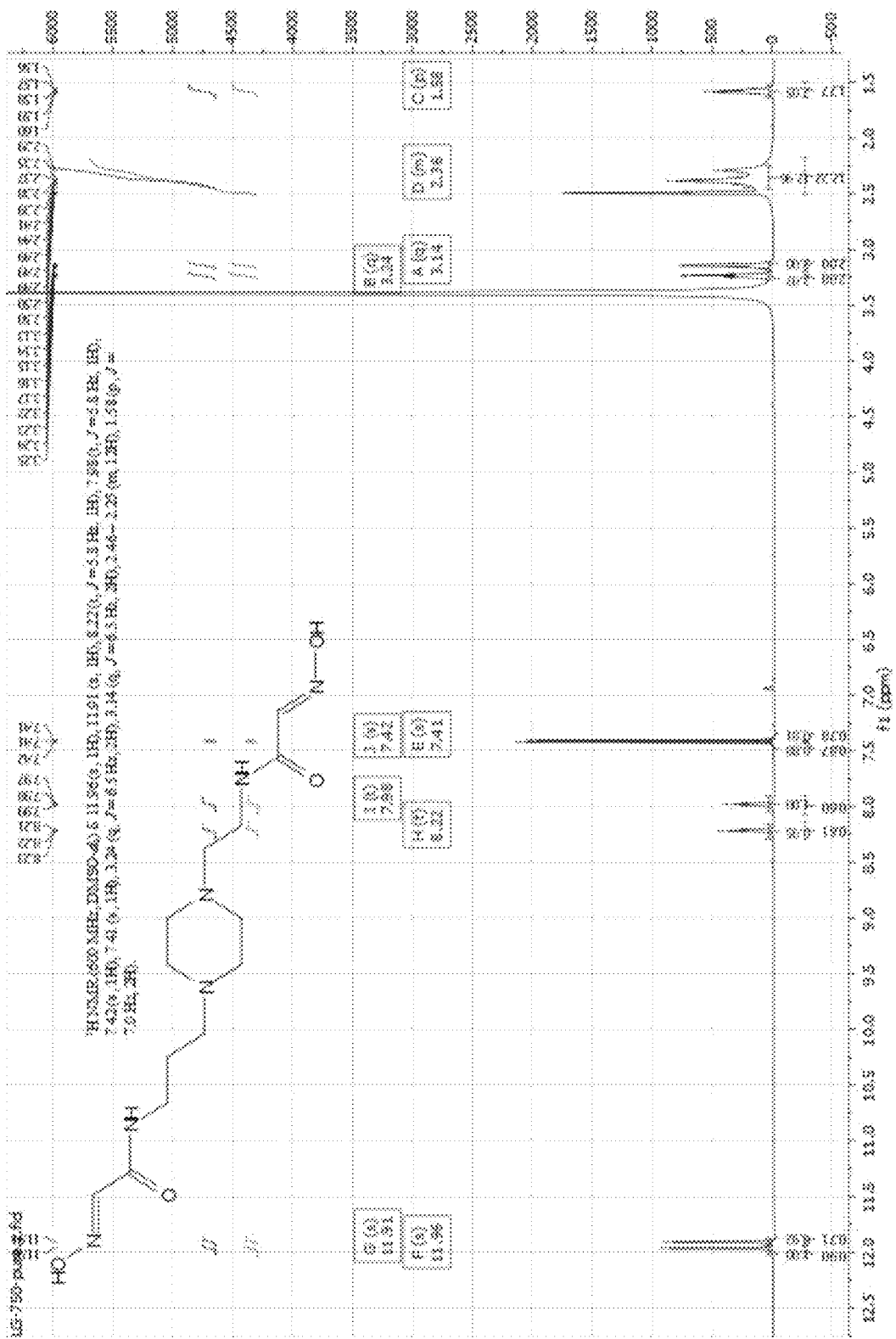
FIG. 6 illustrates an NMR analysis of (2E)-2-(N-hydroxyimino)-N-[3-(4-{2-[(2E)-2-(N-hydroxyimino) acetamido]ethyl}piperazin-1-yl)propyl]acetamide (LG-750) $^1$H NMR as described in detail in Example 1, below.

(2E)-2-(N-hydroxyimino)-N-[3-(4-{2-[(2E)-2-(N-hydroxyimino) acetamido]ethyl}piperazin-1-yl)propyl]acetamide (LG-750) $^1$H NMR: See FIG. 6.

Figure 7:
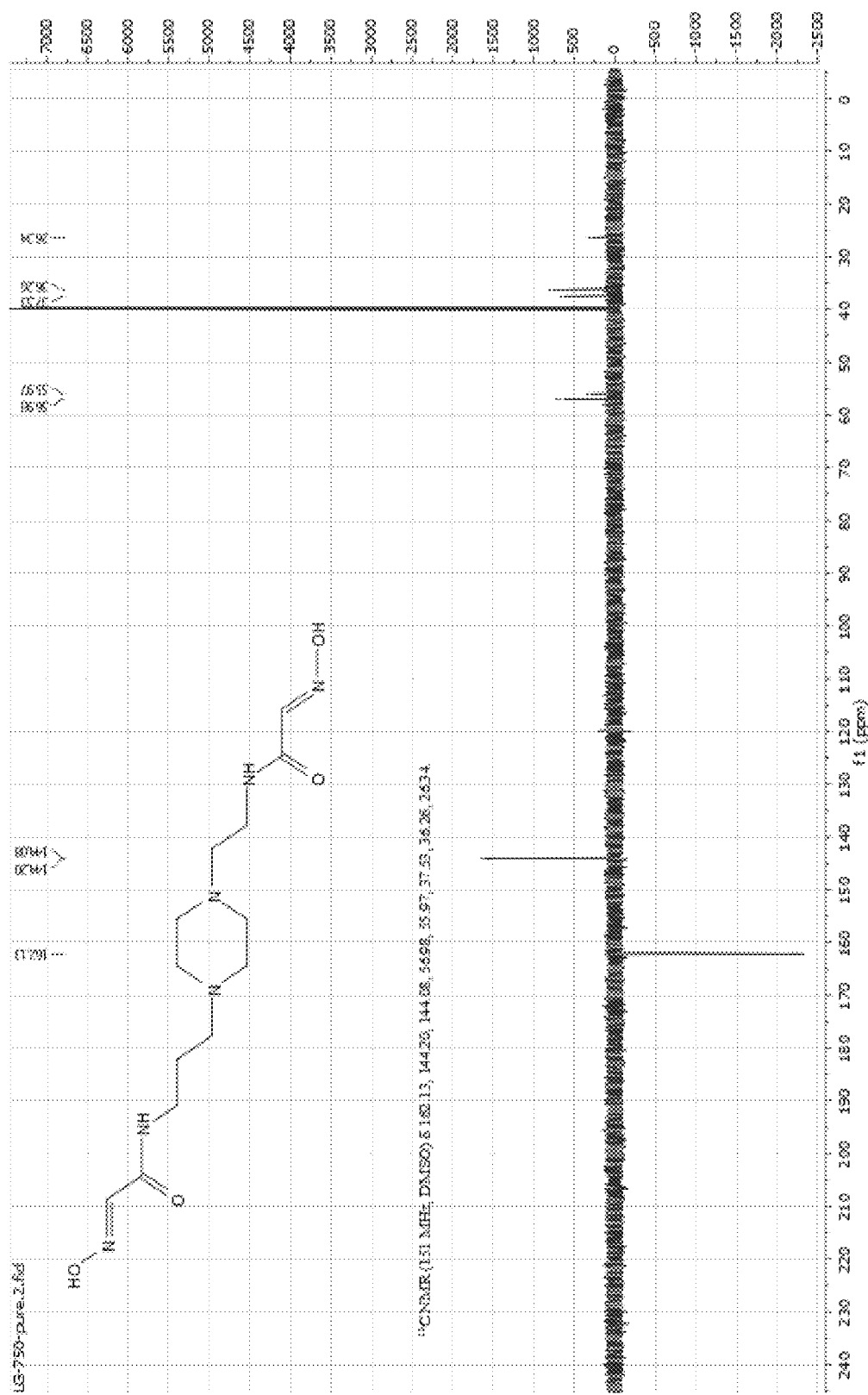
FIG. 7 illustrates an NMR analysis of (2E)-2-(N-hydroxyimino)-N-[3-(4-{2-[(2E)-2-(N-hydroxyimino) acetamido]ethyl}piperazin-1-yl)propyl]acetamide (LG-750) $^{13}$C NMR as described in detail in Example 1, below.

(2E)-2-(N-hydroxyimino)-N-[3-(4-{2-[(2E)-2-(N-hydroxyimino) acetamido]ethyl}piperazin-1-yl)propyl]acetamide (LG-750) $^{13}$C NMR: See FIG. 7.

Figure 8:
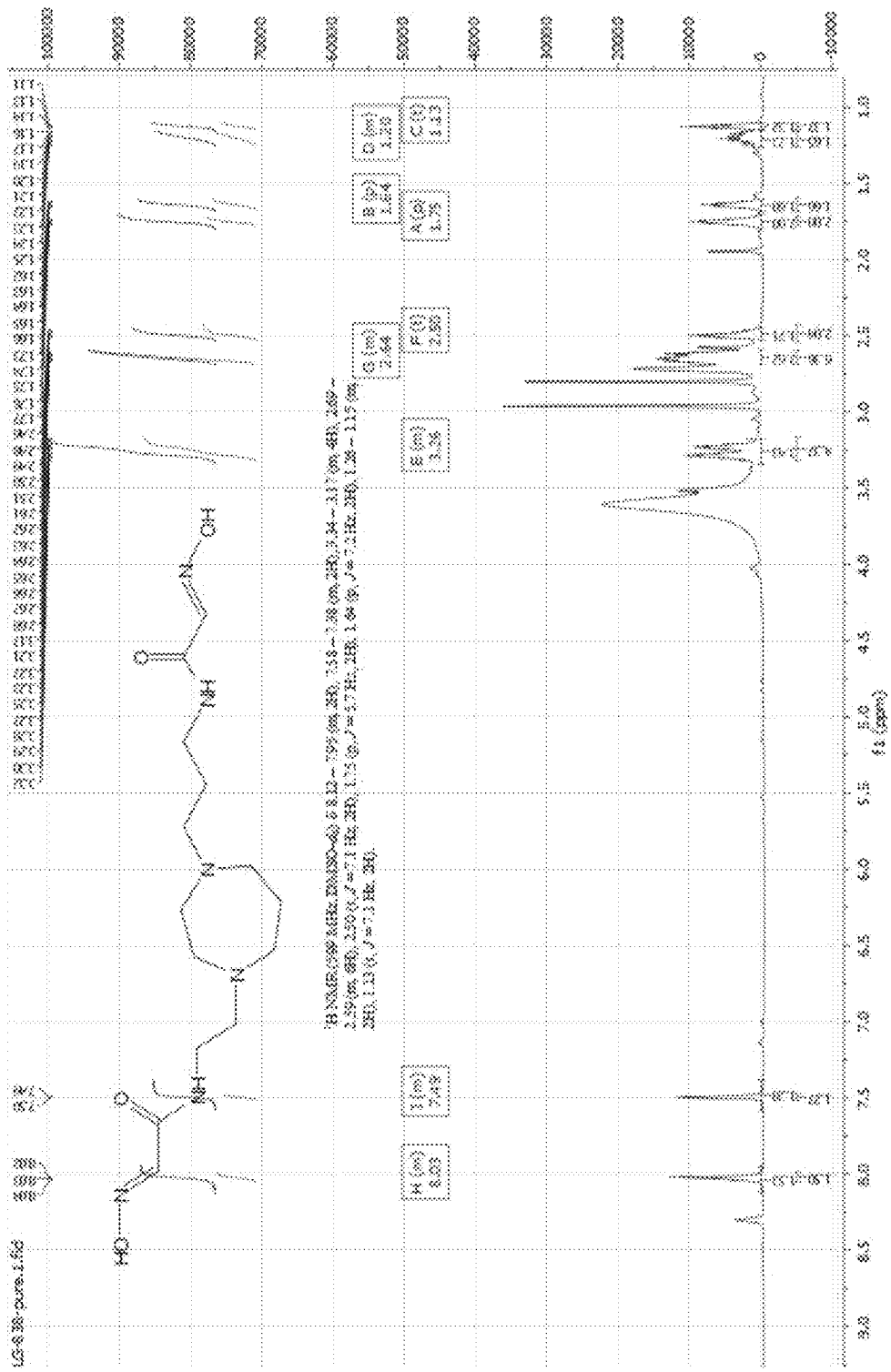
FIG. 8 illustrates an NMR analysis of (2E)-2-(N-hydroxyimino)-N-[3-(4-{2-[(2E)-2-(N-hydroxyimino)acetamido]ethyl}-1,4-diazepan-1-yl)propyl]acetamide (LG-838) $^1$H NMR as described in detail in Example 1, below.

(2E)-2-(N-hydroxyimino)-N-[3-(4-{2-[(2E)-2-(N-hydroxyimino)acetamido]ethyl}-1,4-diazepan-1-yl)propyl]acetamide (LG-838) $^1$H NMR: See FIG. 8.

Figure 9:
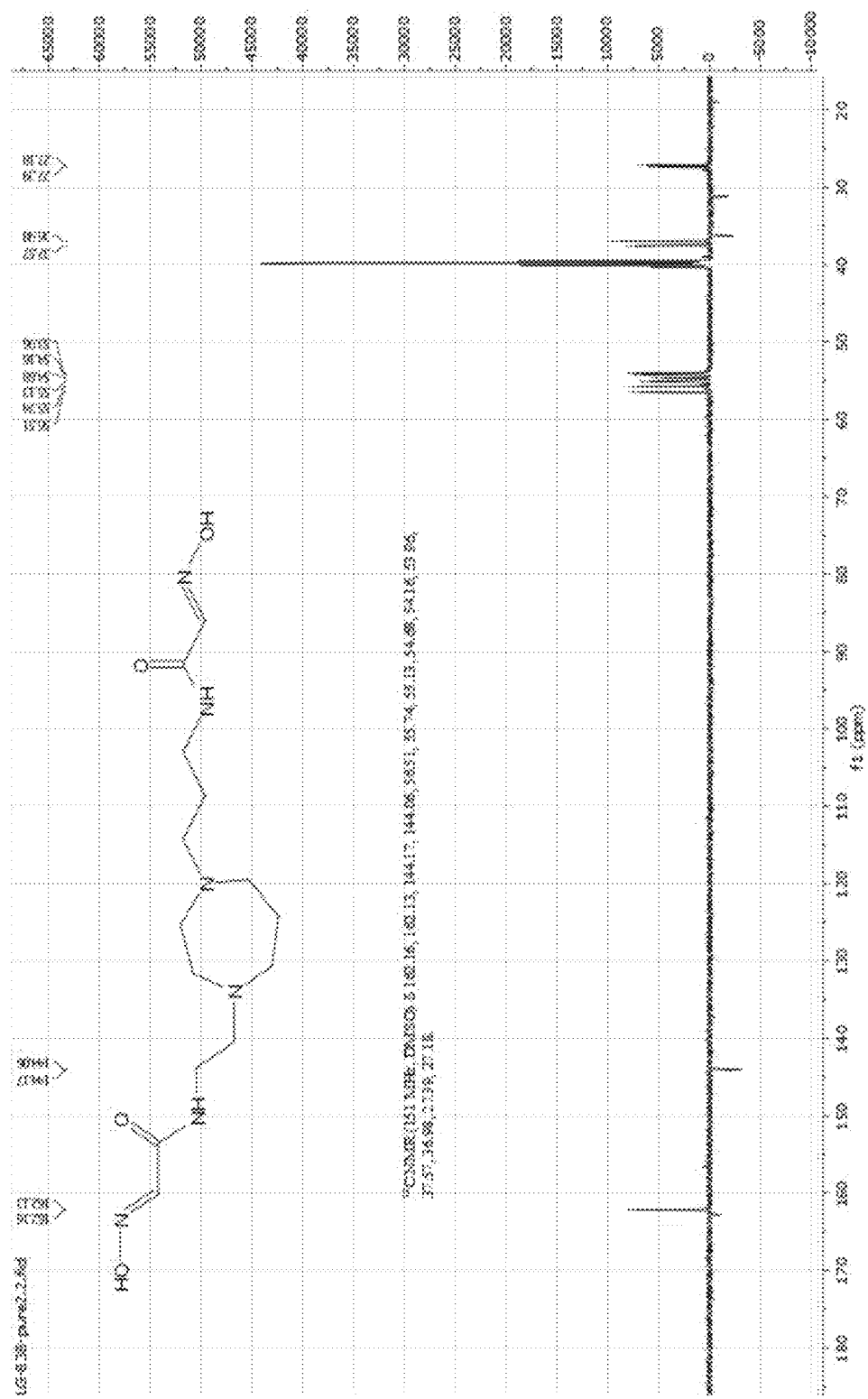
FIG. 9 illustrates an NMR analysis of (2E)-2-(N-hydroxyimino)-N-[3-(4-{2-[(2E)-2-(N-hydroxyimino)acetamido]ethyl}-1,4-diazepan-1-yl)propyl]acetamide (LG-838) $^{13}$C NMR as described in detail in Example 1, below.

(2E)-2-(N-hydroxyimino)-N-[3-(4-{2-[(2E)-2-(N-hydroxyimino)acetamido]ethyl}-1,4-diazepan-1-yl)propyl]acetamide (LG-838) $^{13}$C NMR: See FIG. 9.

Figure 10:
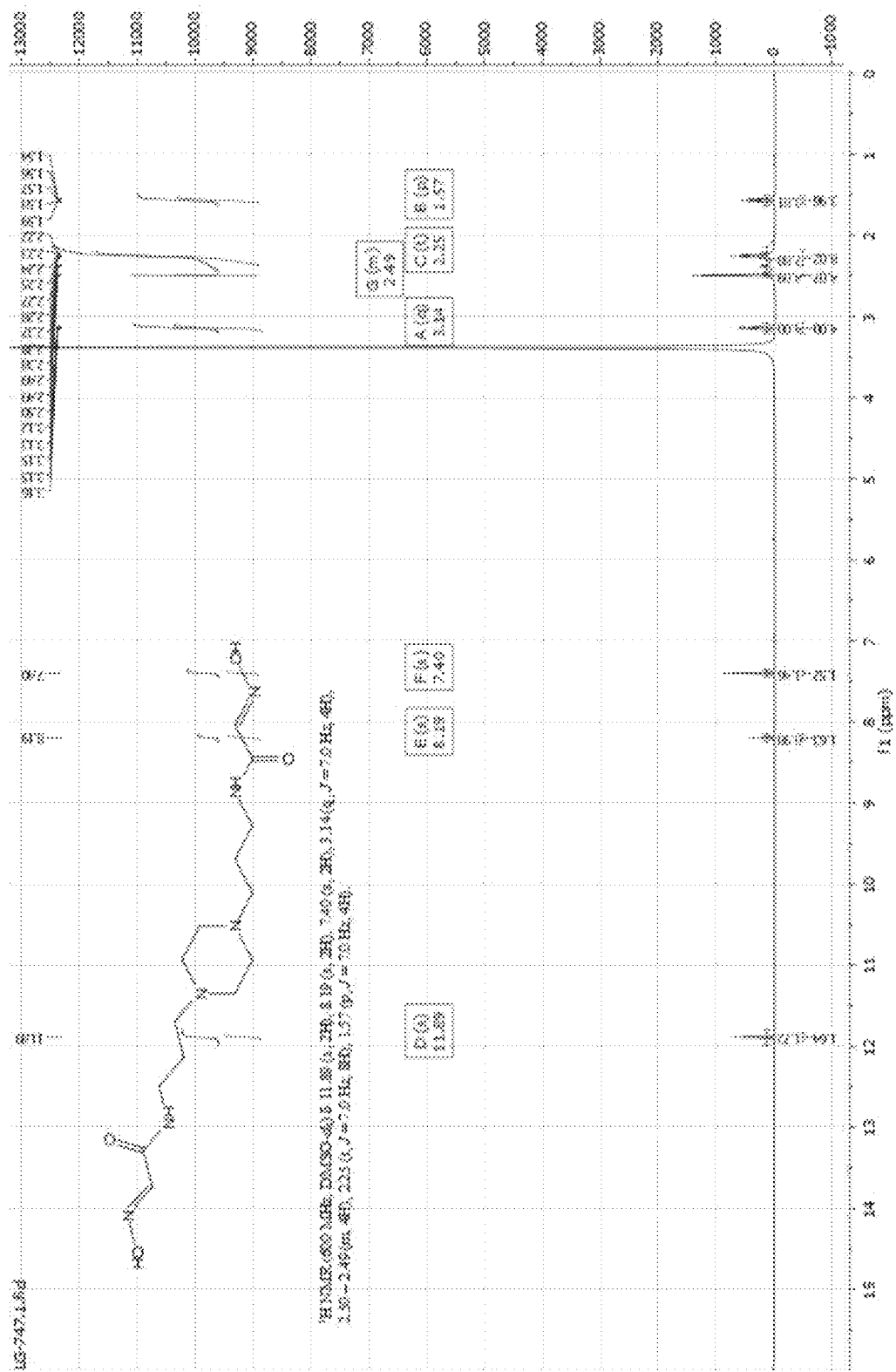
FIG. 10 illustrates an NMR analysis of (2E)-2-(N-hydroxyimino)-N-[3-(4-{3-[(2E)-2-(N-hydroxyimino) acetamido]propyl}piperazin-1-yl)propyl]acetamide (LG-747) $^1$H NMR as described in detail in Example 1, below.

(2E)-2-(N-hydroxyimino)-N-[3-(4-{3-[(2E)-2-(N-hydroxyimino) acetamido]propyl}piperazin-1-yl)propyl]acetamide (LG-747) $^1$H NMR: See FIG. 10.

Figure 11:
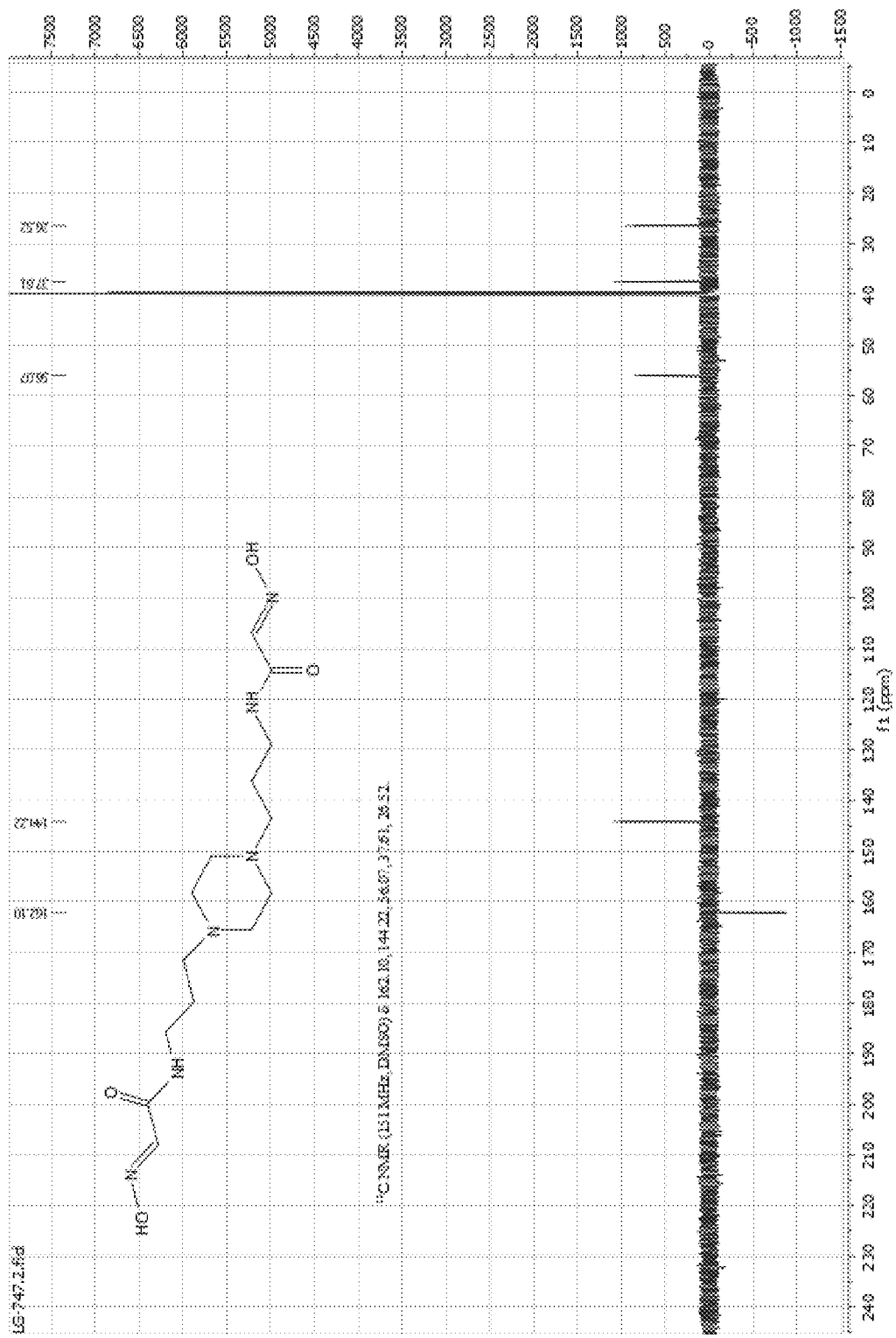
FIG. 11 illustrates an NMR analysis of (2E)-2-(N-hydroxyimino)-N-[3-(4-{3-[(2E)-2-(N-hydroxyimino) acetamido]propyl}piperazin-1-yl)propyl]acetamide (LG-747) $^{13}$C NMR as described in detail in Example 1, below.

(2E)-2-(N-hydroxyimino)-N-[3-(4-{3-[(2E)-2-(N-hydroxyimino) acetamido]propyl}piperazin-1-yl)propyl]acetamide (LG-747) $^{13}$C NMR: See FIG. 11.

Figure 12:
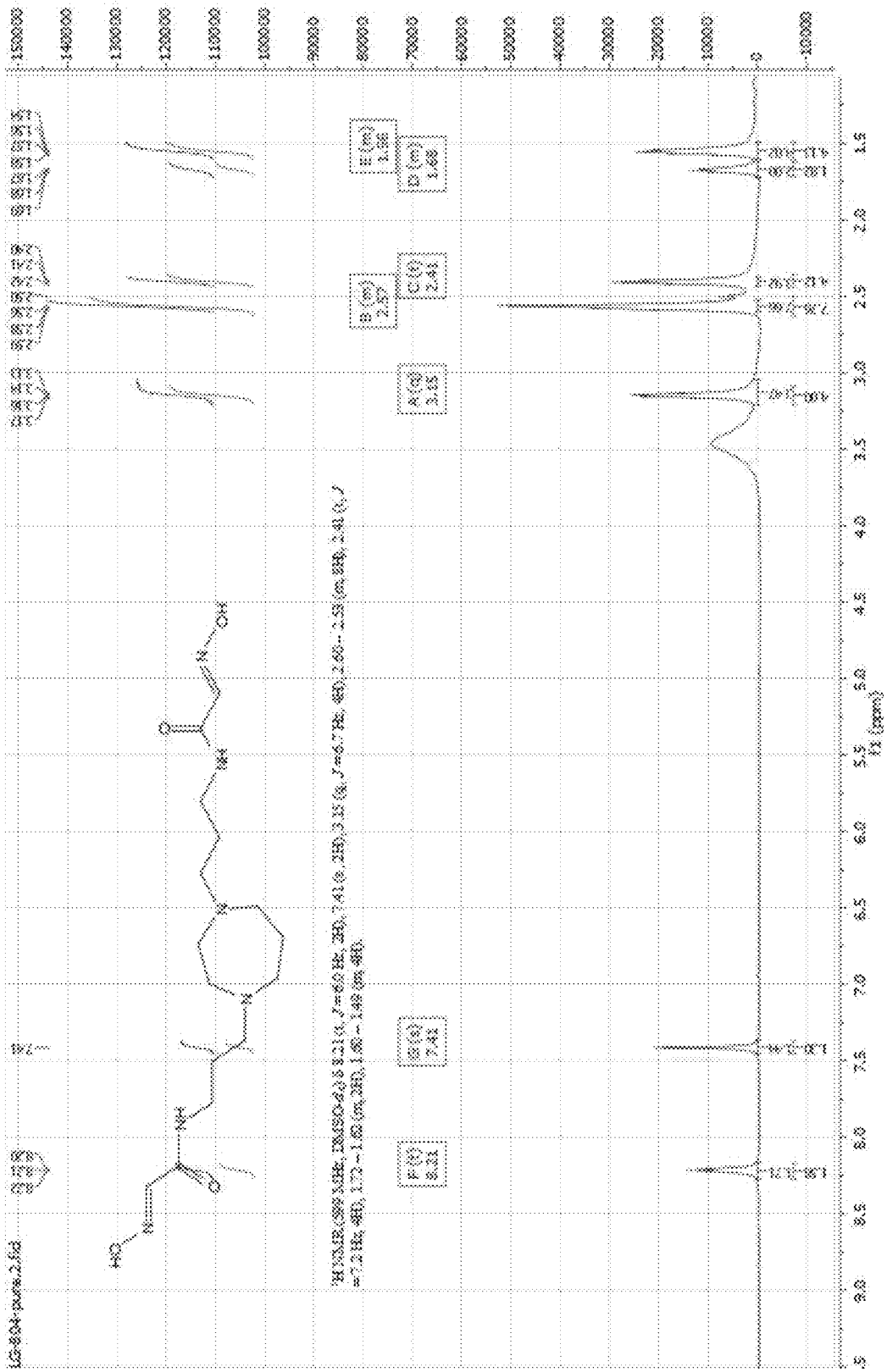
FIG. 12 illustrates an NMR analysis of (2E)-2-(N-hydroxyimino)-N-[3-(4-{3-[(2E)-2-(N-hydroxyimino)acetamido]propyl}-1,4-diazepan-1-yl)propyl]acetamide (LG-804) $^1$H NMR as described in detail in Example 1, below.

(2E)-2-(N-hydroxyimino)-N-[3-(4-{3-[(2E)-2-(N-hydroxyimino)acetamido]propyl}-1,4-diazepan-1-yl)propyl]acetamide (LG-804) $^{1}$H NMR: See FIG. 12.

Figure 13:
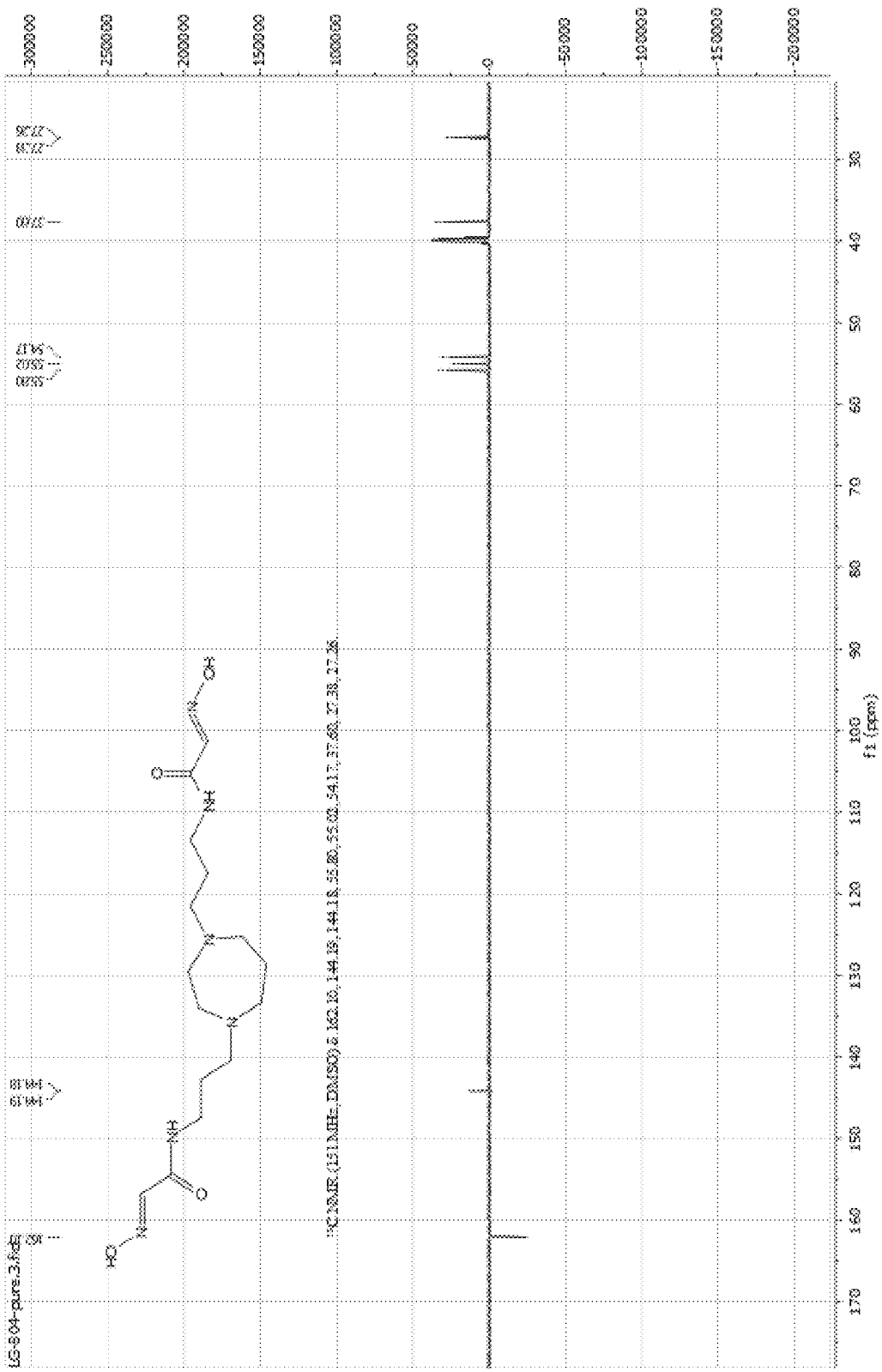
FIG. 13 illustrates an NMR analysis of (2E)-2-(N-hydroxyimino)-N-[3-(4-{3-[(2E)-2-(N-hydroxyimino)acetamido]propyl}-1,4-diazepan-1-yl)propyl]acetamide (LG-804) $^{13}$C NMR as described in detail in Example 1, below.

(2E)-2-(N-hydroxyimino)-N-[3-(4-{3-[(2E)-2-(N-hydroxyimino)acetamido]propyl}-1,4-diazepan-1-yl)propyl]acetamide (LG-804) $^{13}$C NMR: See FIG. 13.

Figure 14:
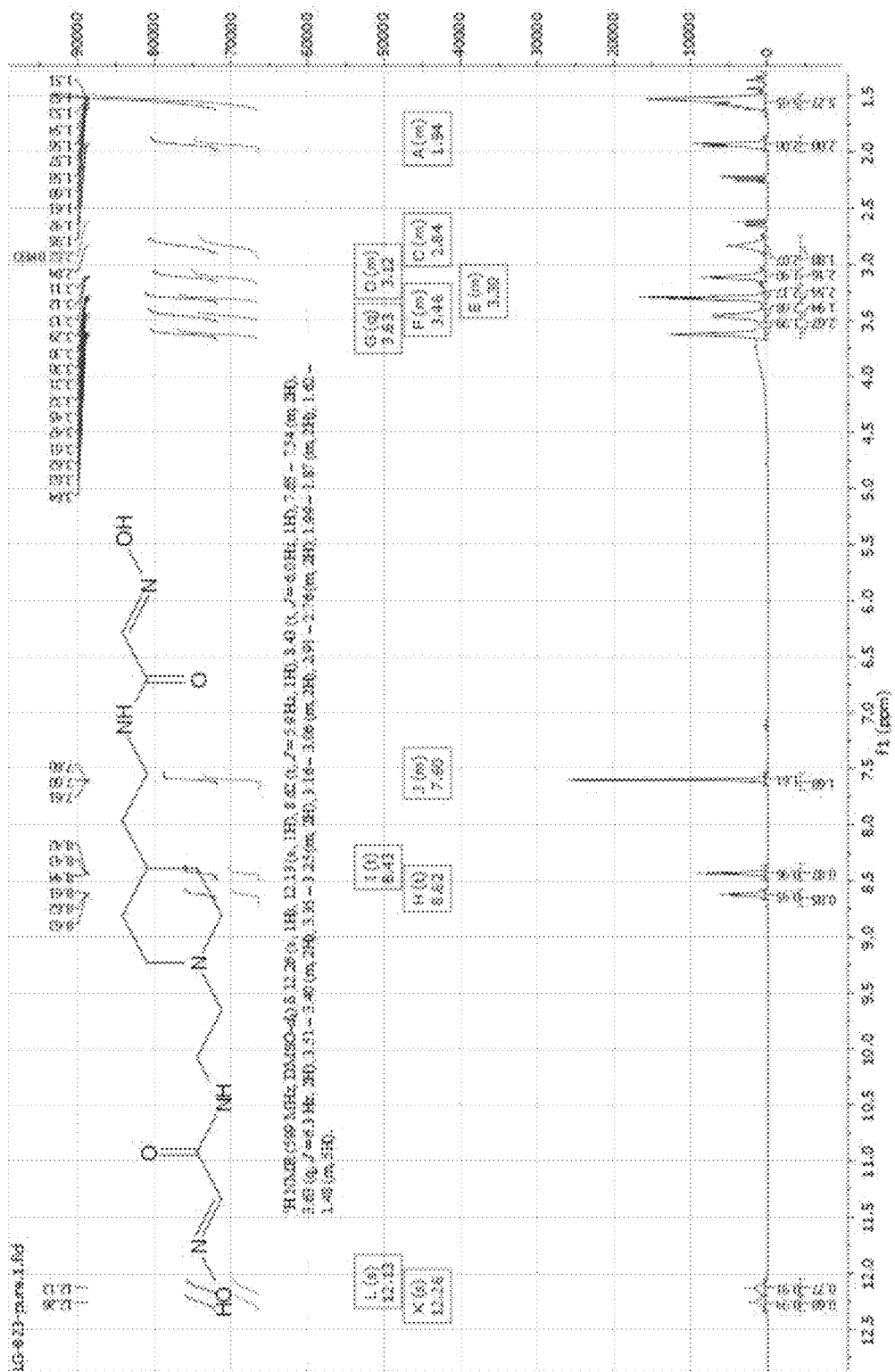
FIG. 14 illustrates an NMR analysis of (2E)-2-(N-hydroxyimino)-N-[2-(1-{2-[(2E)-2-(N-hydroxyimino) acetamido]ethyl}piperidin-4-yl)ethyl]acetamide (LG-823) $^1$H NMR as described in detail in Example 1, below.

(2E)-2-(N-hydroxyimino)-N-[2-(1-{2-[(2E)-2-(N-hydroxyimino) acetamido]ethyl}piperidin-4-yl)ethyl]acetamide (LG-823) $^{1}$H NMR: See FIG. 14.

Figure 15:
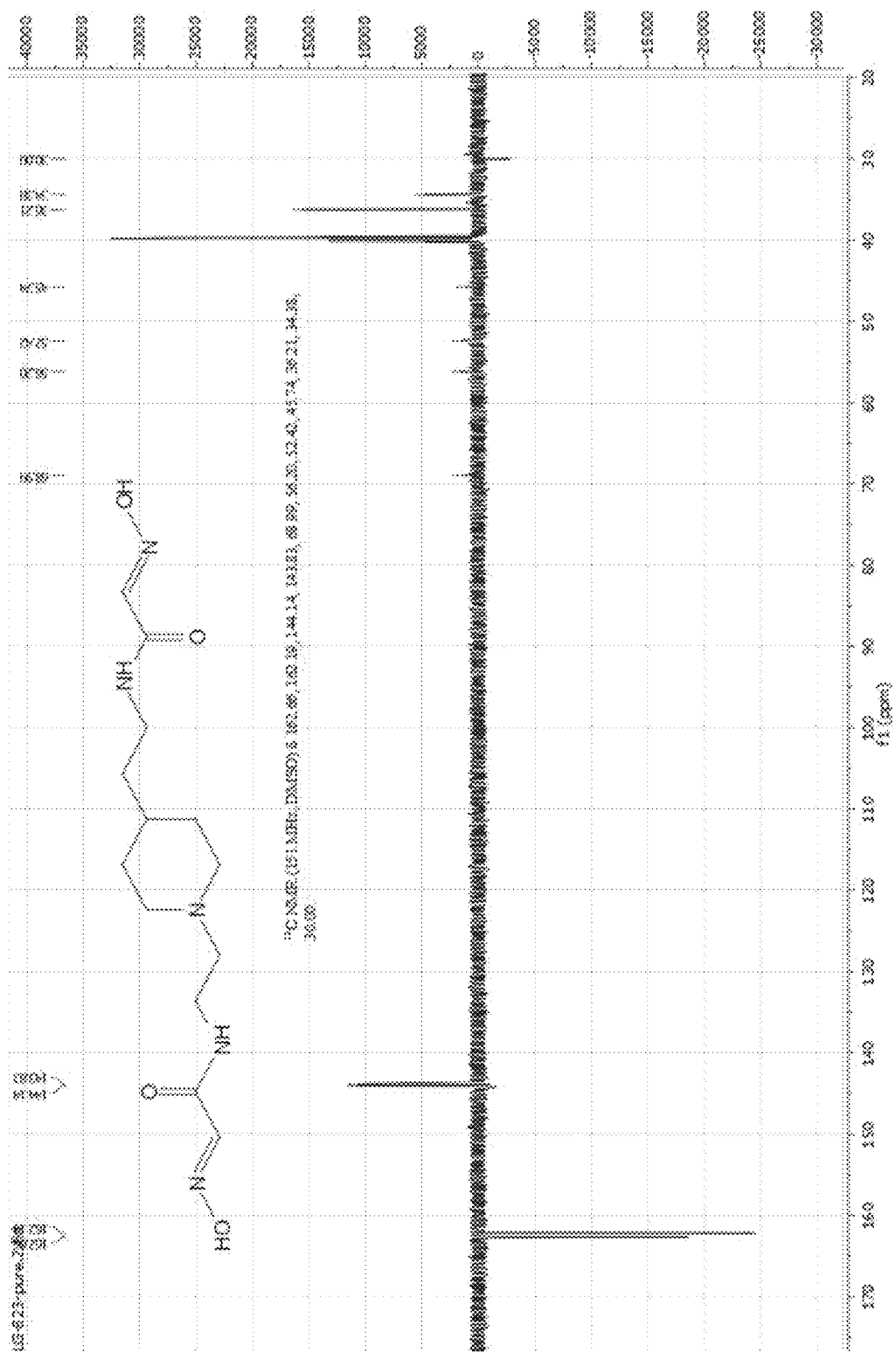
FIG. 15 illustrates an NMR analysis of (2E)-2-(N-hydroxyimino)-N-[2-(1-{2-[(2E)-2-(N-hydroxyimino) acetamido]ethyl}piperidin-4-yl)ethyl]acetamide (LG-823) $^{13}$C NMR as described in detail in Example 1, below.

(2E)-2-(N-hydroxyimino)-N-[2-(1-{2-[(2E)-2-(N-hydroxyimino) acetamido]ethyl}piperidin-4-yl)ethyl]acetamide (LG-823) $^{13}$C NMR: See FIG. 15.

Figure 16:
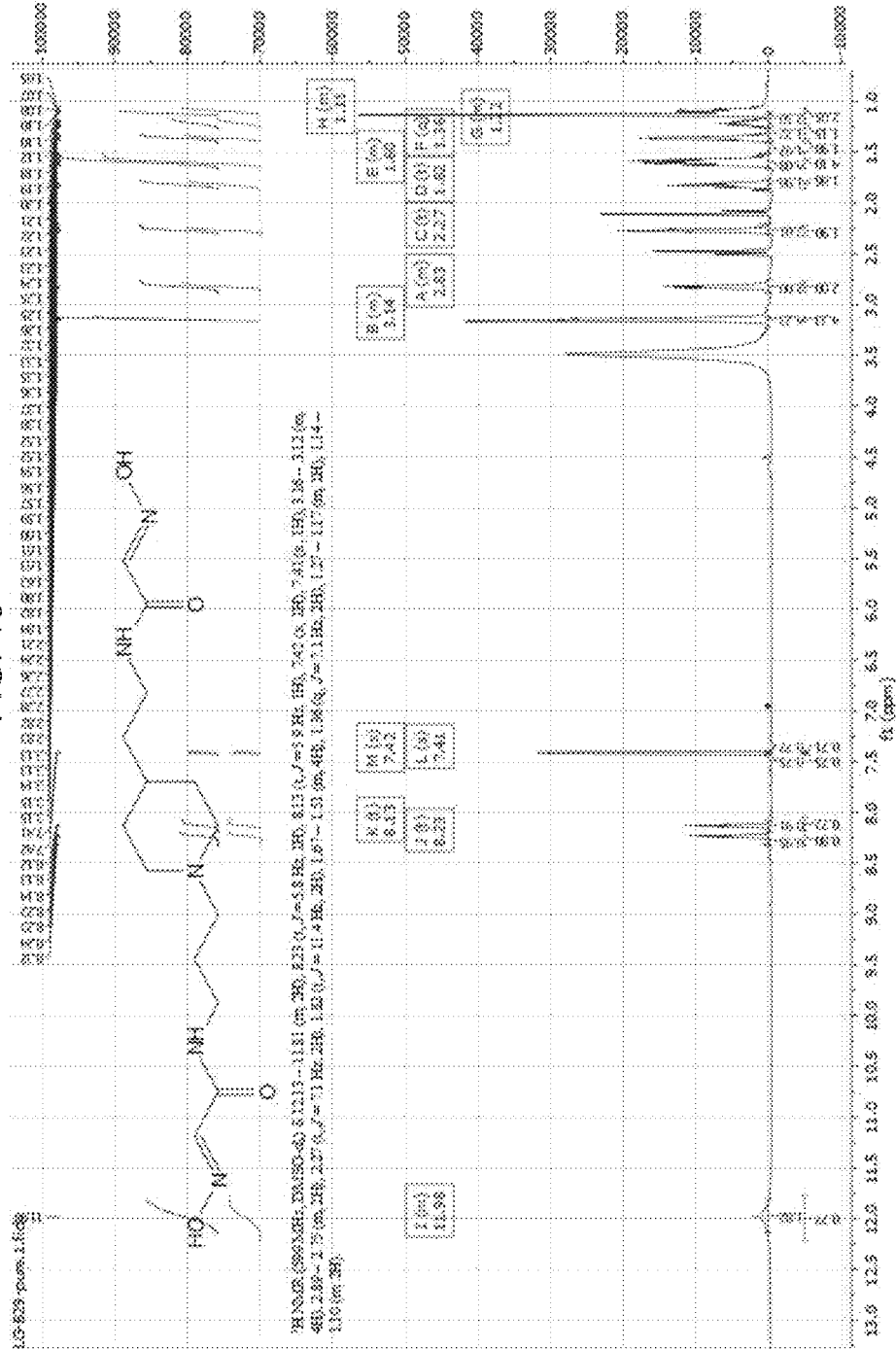
FIG. 16 illustrates an NMR analysis of (2E)-2-(N-hydroxyimino)-N-[3-(4-{2-[(2E)-2-(N-hydroxyimino) acetamido]ethyl}piperidin-1-yl)propyl]acetamide (LG-829) $^1$H NMR as described in detail in Example 1, below.

(2E)-2-(N-hydroxyimino)-N-[3-(4-{2-[(2E)-2-(N-hydroxyimino) acetamido]ethyl}piperidin-1-yl)propyl]acetamide (LG-829) $^{1}$H NMR: See FIG. 16.

Figure 17:
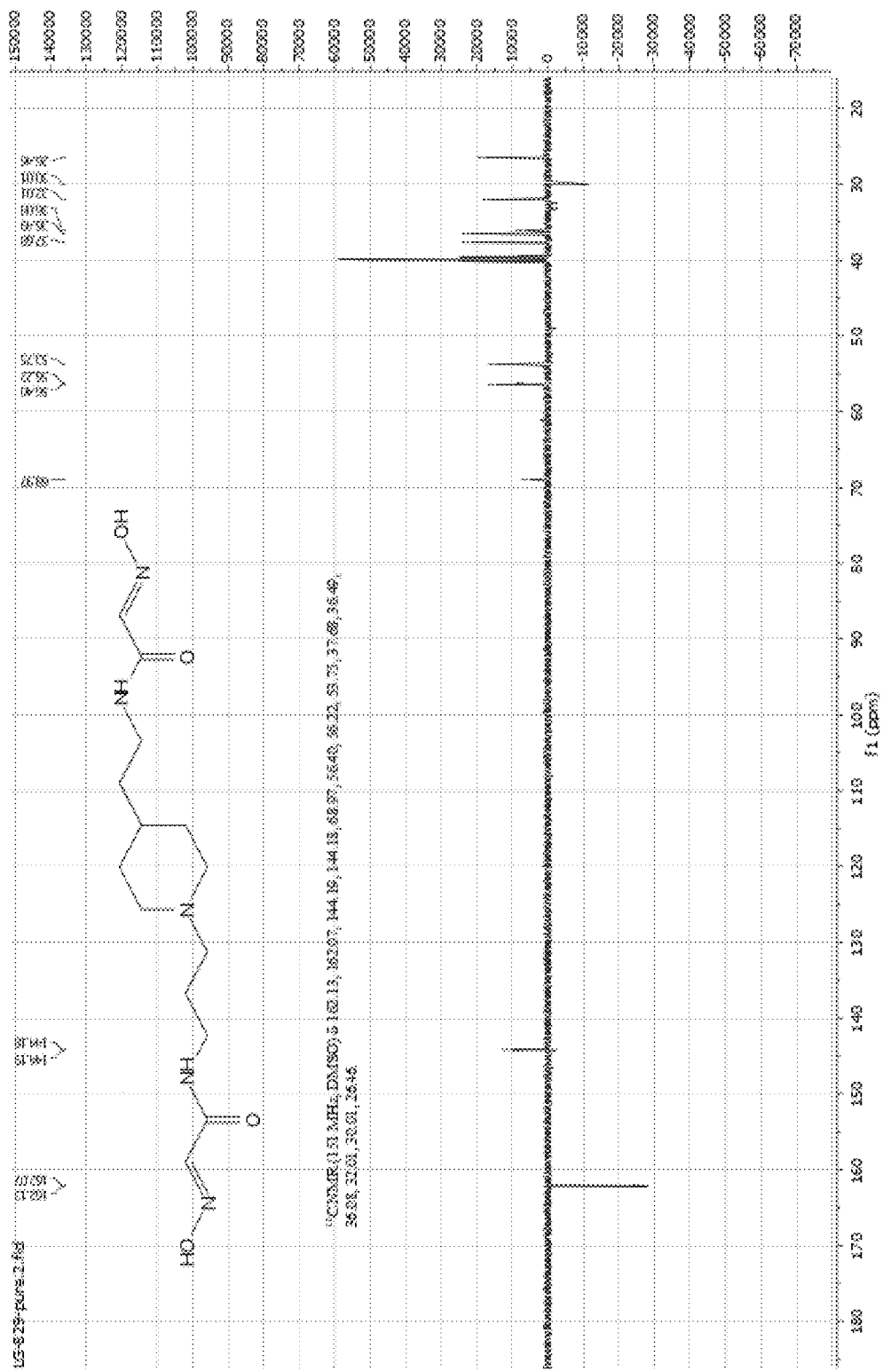
FIG. 17 illustrates an NMR analysis of (2E)-2-(N-hydroxyimino)-N-[3-(4-{2-[(2E)-2-(N-hydroxyimino) acetamido]ethyl}piperidin-1-yl)propyl]acetamide (LG-829) $^{13}$C NMR as described in detail in Example 1, below.

(2E)-2-(N-hydroxyimino)-N-[3-(4-{2-[(2E)-2-(N-hydroxyimino) acetamido]ethyl}piperidin-1-yl)propyl]acetamide (LG-829) $^{13}$C NMR: See FIG. 17.

Figure 18:
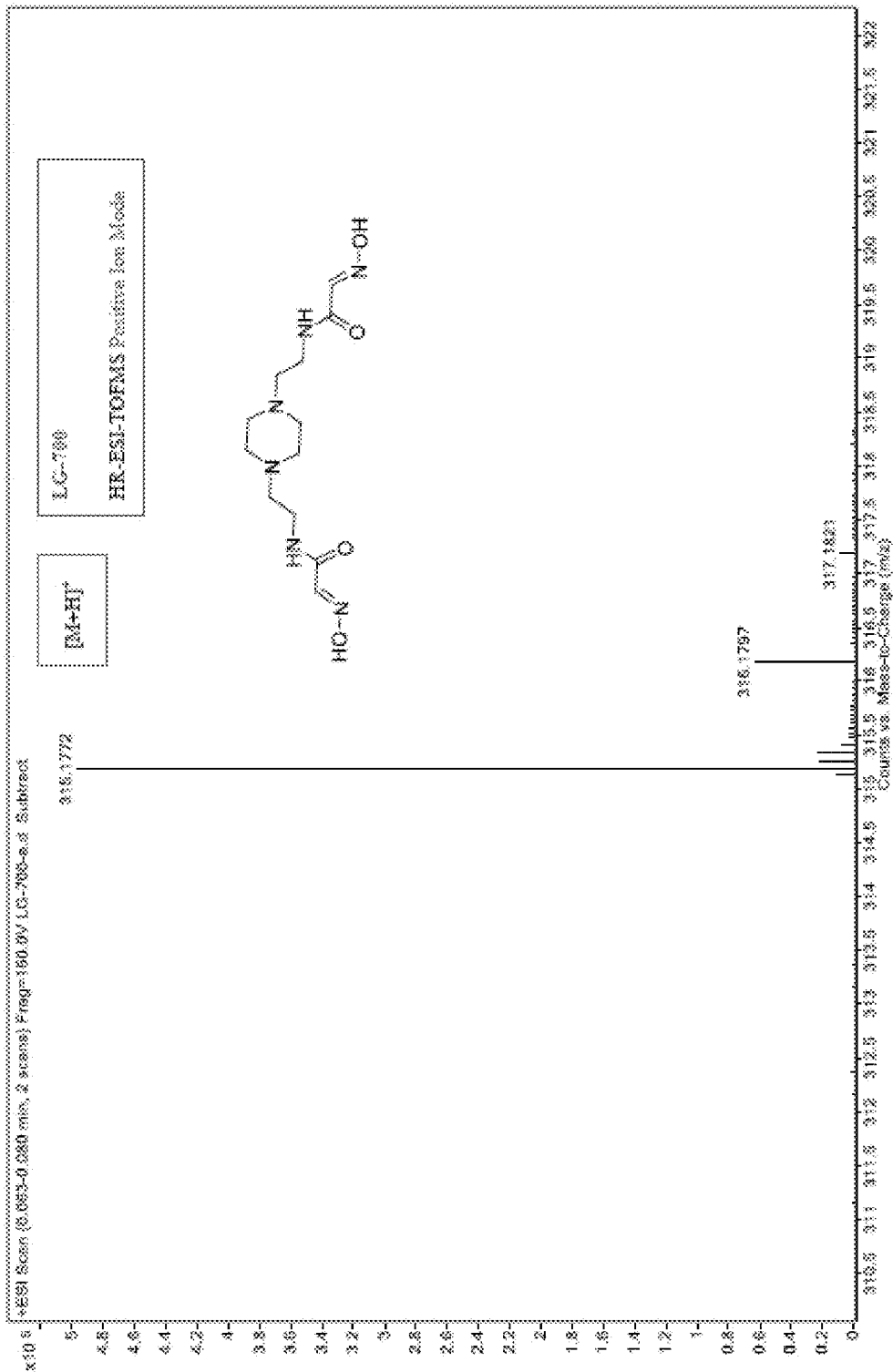
FIG. 18 illustrates a high-resolution mass spectrometry (HRMS) analysis of (2E)-2-(N-hydroxyimino)-N-[2-(4-{2-[(2E)-2-(N-hydroxyimino) acetamido]ethyl}piperazin-1-yl) ethyl]acetamide (LG-700) HRMS: See FIG. 18.

(2E)-2-(N-hydroxyimino)-N-[2-(4-{2-[(2E)-2-(N-hydroxyimino) acetamido]ethyl}piperazin-1-yl)ethyl]acetamide (LG-700) HRMS: See FIG. 18.

Figure 19:
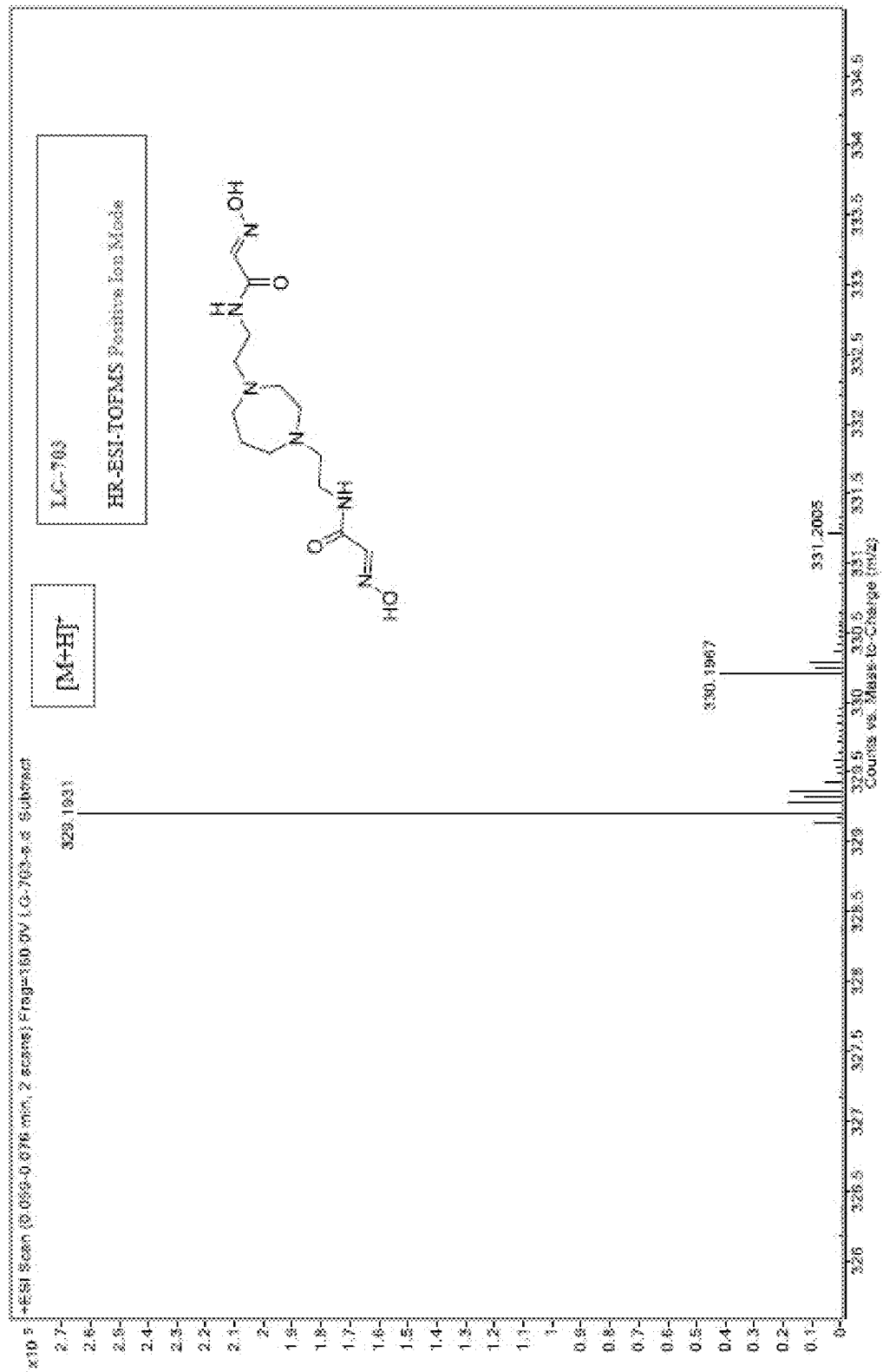
FIG. 19 illustrates an HRMS analysis of (2E)-2-(N-hydroxyimino)-N-[2-(4-{2-[(2E)-2-(N-hydroxyimino)acetamido]ethyl}-1,4-diazepan-1-yl)ethyl]acetamide (LG-703) HRMS as described in detail in Example 1, below.

(2E)-2-(N-hydroxyimino)-N-[2-(4-{2-[(2E)-2-(N-hydroxyimino)acetamido]ethyl}-1,4-diazepan-1-yl)ethyl]acetamide (LG-703) HRMS: See FIG. 19.

Figure 20:
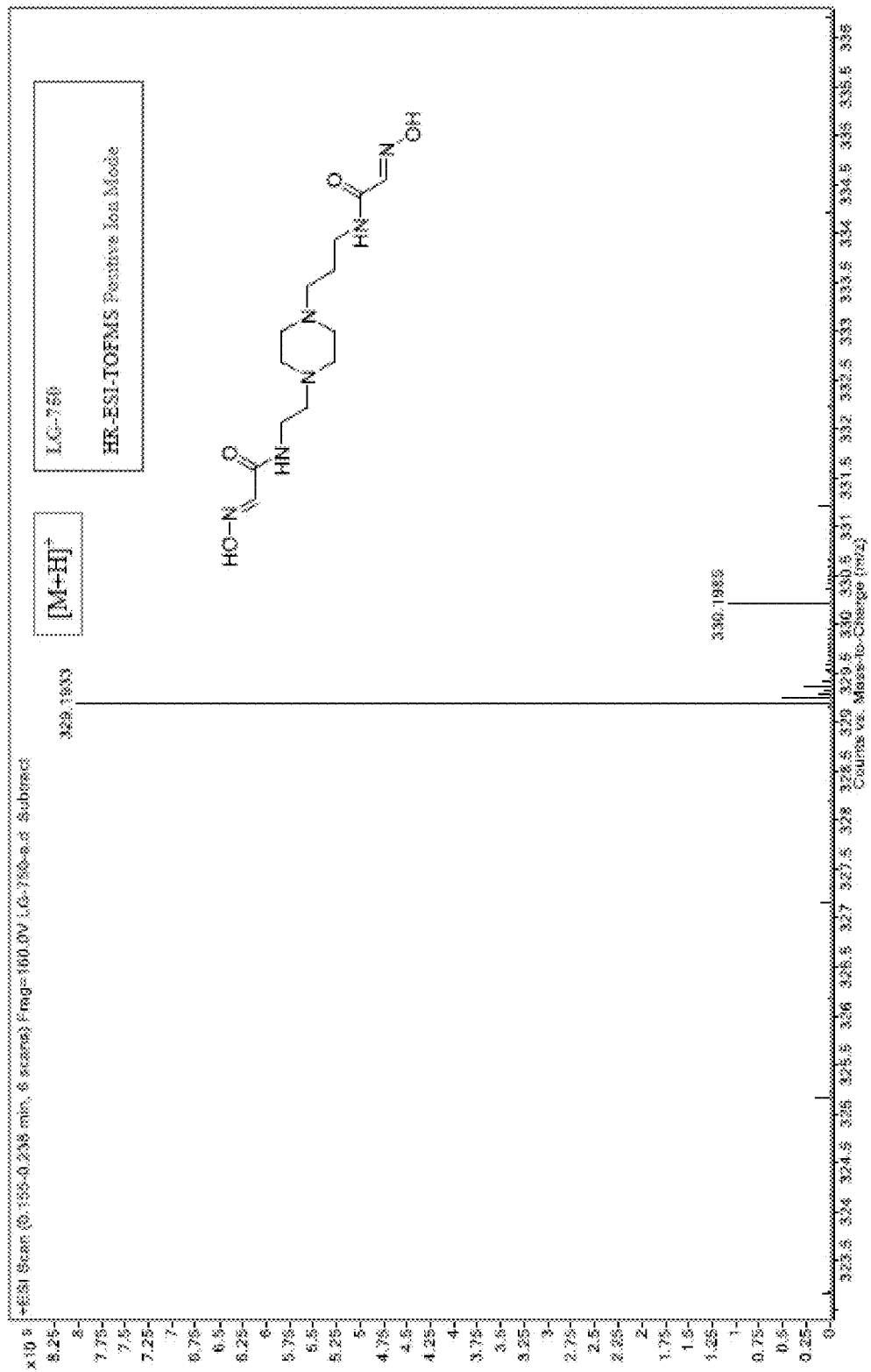
FIG. 20 illustrates an HRMS analysis of (2E)-2-(N-hydroxyimino)-N-[3-(4-{2-[(2E)-2-(N-hydroxyimino)acetamido]ethyl}piperazin-1-yl)propyl]acetamide (LG-750) HRMS as described in detail in Example 1, below.

(2E)-2-(N-hydroxyimino)-N-[3-(4-{2-[(2E)-2-(N-hydroxyimino)acetamido]ethyl}piperazin-1-yl)propyl]acetamide (LG-750) HRMS: See FIG. 20.

Figure 21:
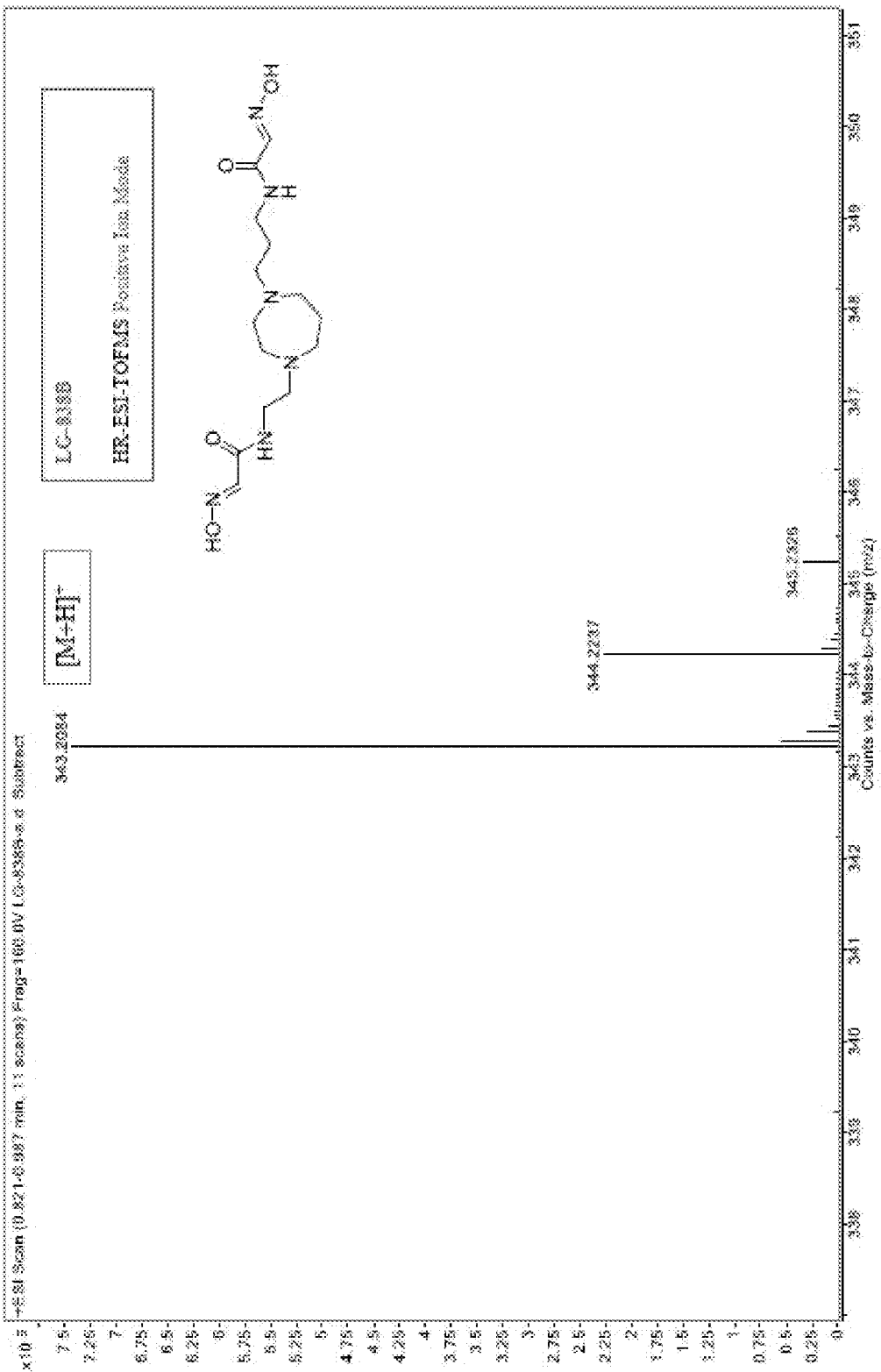
FIG. 21 illustrates an HRMS analysis of (2E)-2-(N-hydroxyimino)-N-[3-(4-{2-[(2E)-2-(N-hydroxyimino)acetamido]ethyl}-1,4-diazepan-1-yl)propyl]acetamide (LG-838) HRMS as described in detail in Example 1, below.

(2E)-2-(N-hydroxyimino)-N-[3-(4-{2-[(2E)-2-(N-hydroxyimino)acetamido]ethyl}-1,4-diazepan-1-yl)propyl]acetamide (LG-838) HRMS: See FIG. 21.

Figure 22:
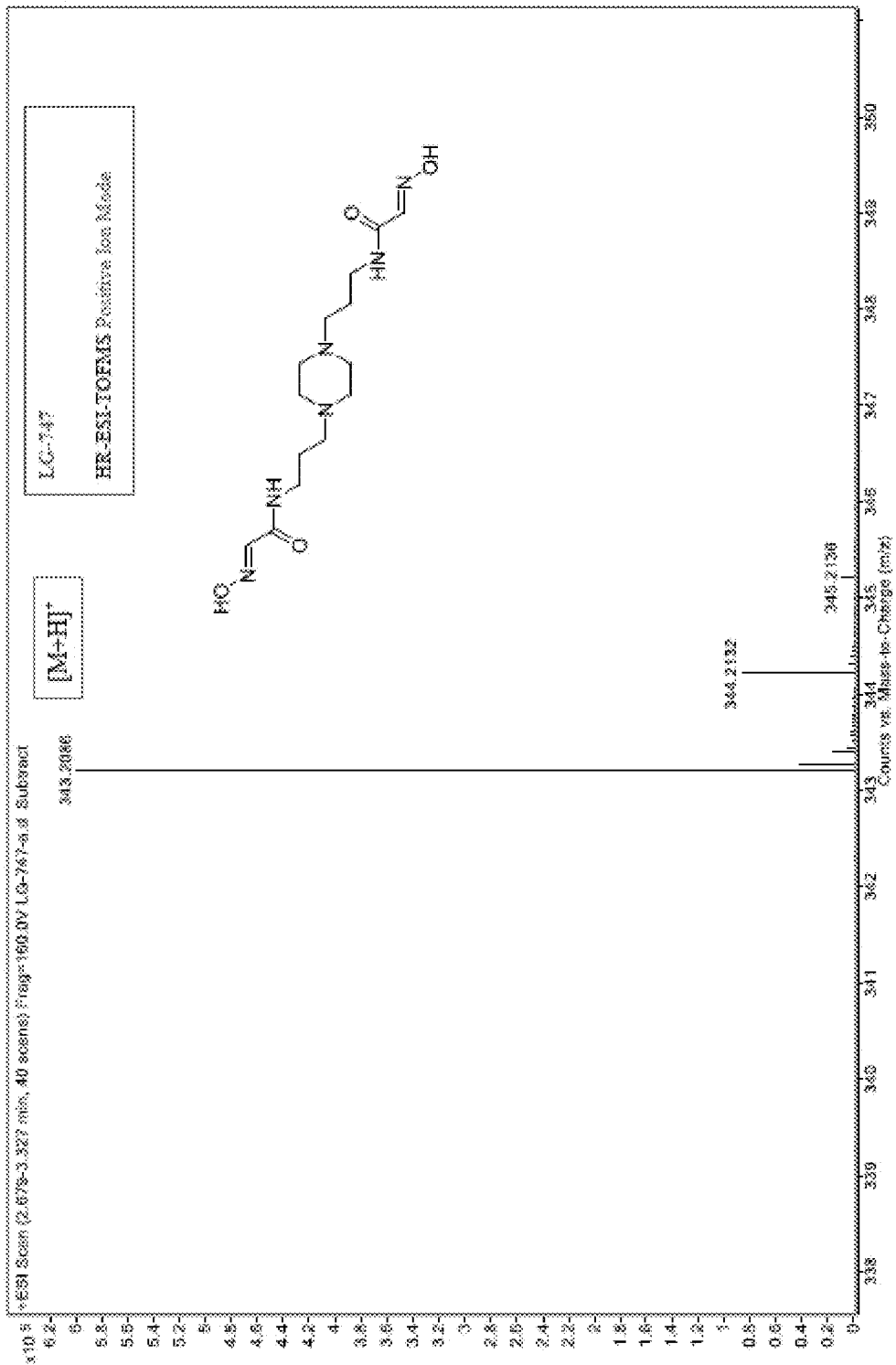
FIG. 22 illustrates an HRMS analysis of (2E)-2-(N-hydroxyimino)-N-[3-(4-{3-[(2E)-2-(N-hydroxyimino)acetamido]propyl}piperazin-1-yl)propyl]acetamide (LG-747) HRMS as described in detail in Example 1, below.

(2E)-2-(N-hydroxyimino)-N-[3-(4-{3-[(2E)-2-(N-hydroxyimino)acetamido]propyl}piperazin-1-yl)propyl]acetamide (LG-747) HRMS: See FIG. 22.

Figure 23:
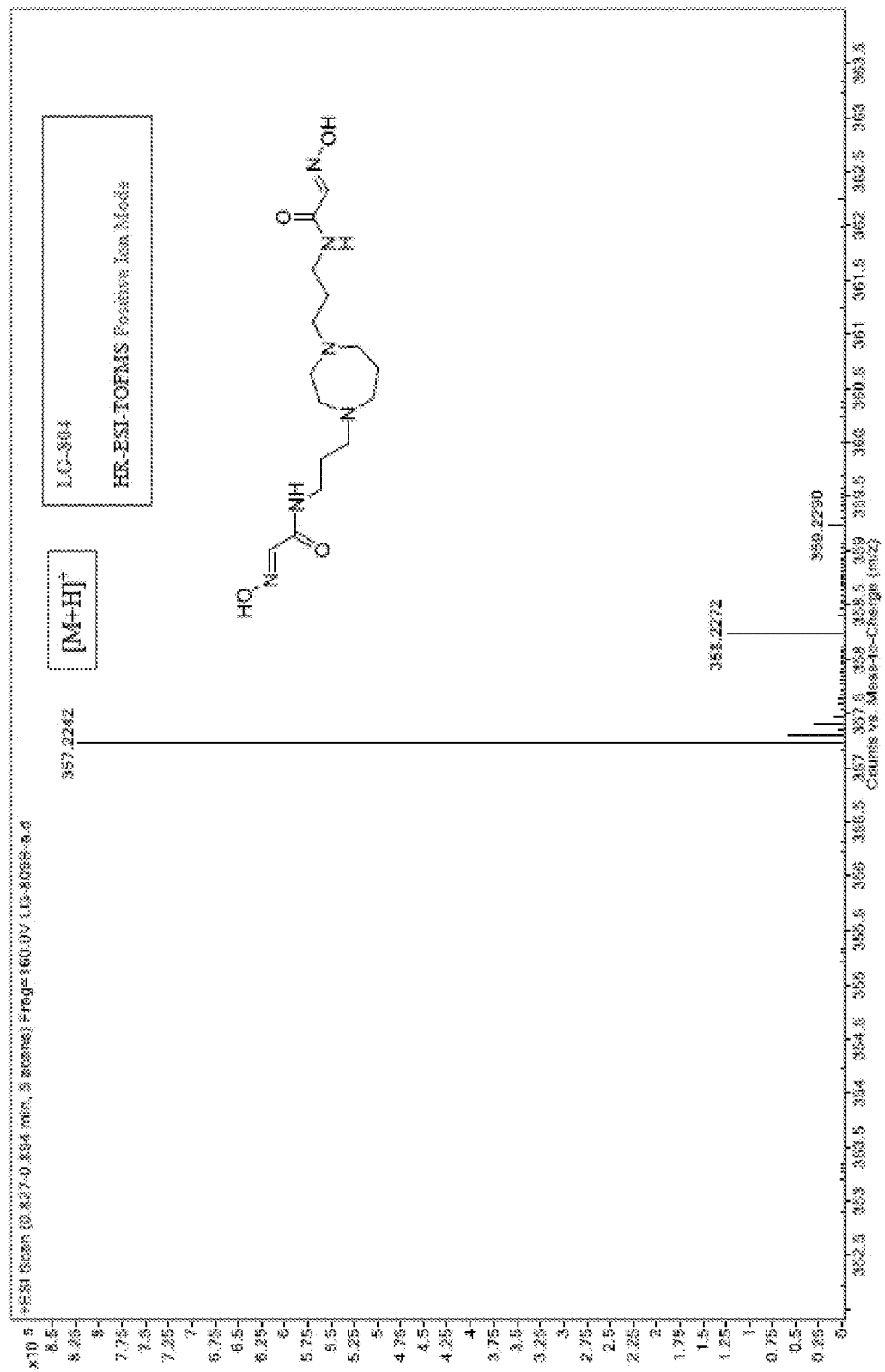
FIG. 23 illustrates an HRMS analysis of (2E)-2-(N-hydroxyimino)-N-[3-(4-{3-[(2E)-2-(N-hydroxyimino)acetamido]propyl}-1,4-diazepan-1-yl)propyl]acetamide (LG-804) HRMS as described in detail in Example 1, below.

(2E)-2-(N-hydroxyimino)-N-[3-(4-{3-[(2E)-2-(N-hydroxyimino)acetamido]propyl}-1,4-diazepan-1-yl)propyl]acetamide (LG-804) HRMS: See FIG. 23.

Figure 24:
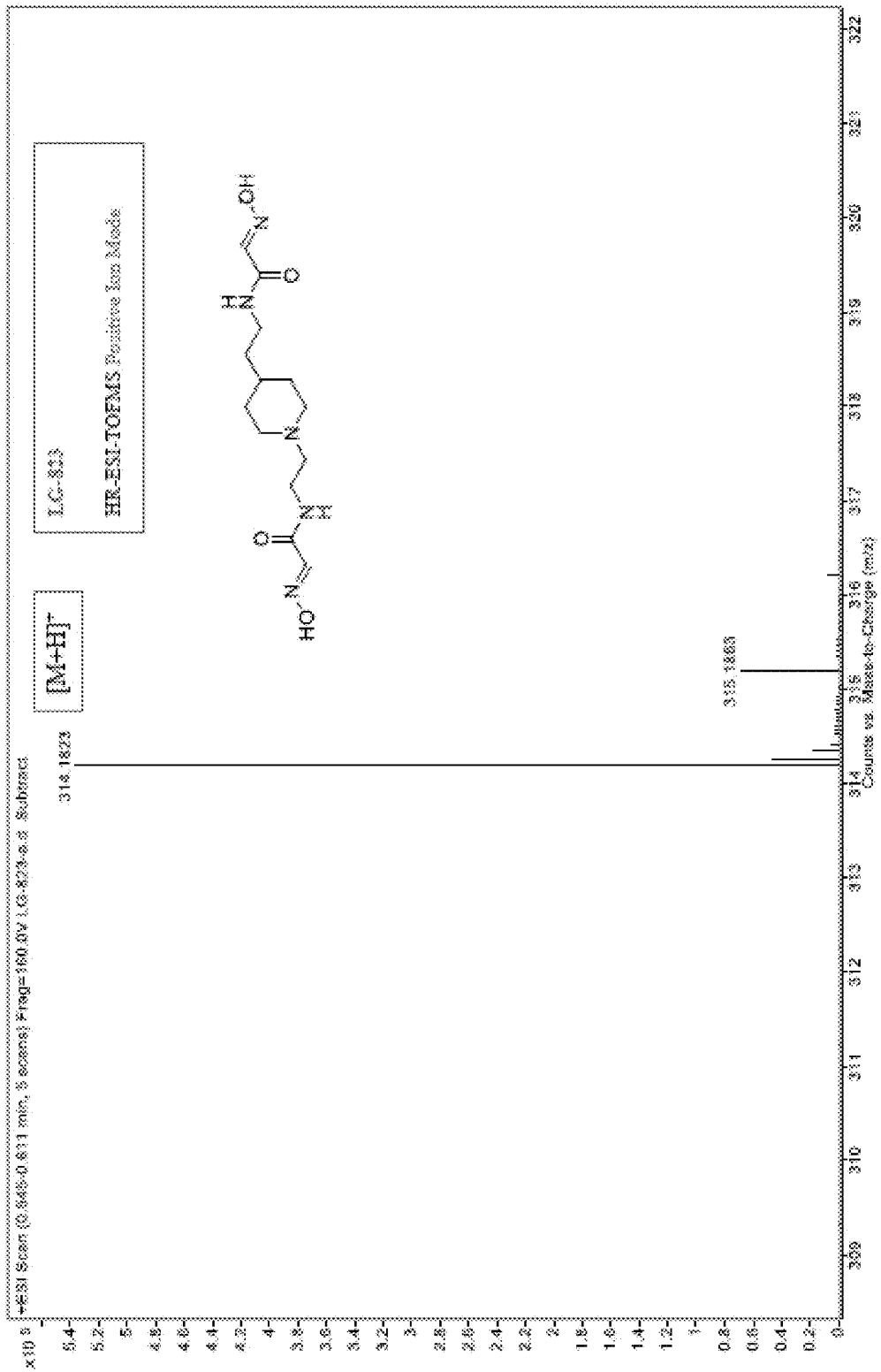
FIG. 24 illustrates an HRMS analysis of (2E)-2-(N-hydroxyimino)-N-[2-(1-{2-[(2E)-2-(N-hydroxyimino)acetamido]ethyl}piperidin-4-yl)ethyl]acetamide (LG-823) HRMS as described in detail in Example 1, below.

(2E)-2-(N-hydroxyimino)-N-[2-(1-{2-[(2E)-2-(N-hydroxyimino)acetamido]ethyl}piperidin-4-yl)ethyl]acetamide (LG-823) HRMS: See FIG. 24.

Figure 25:
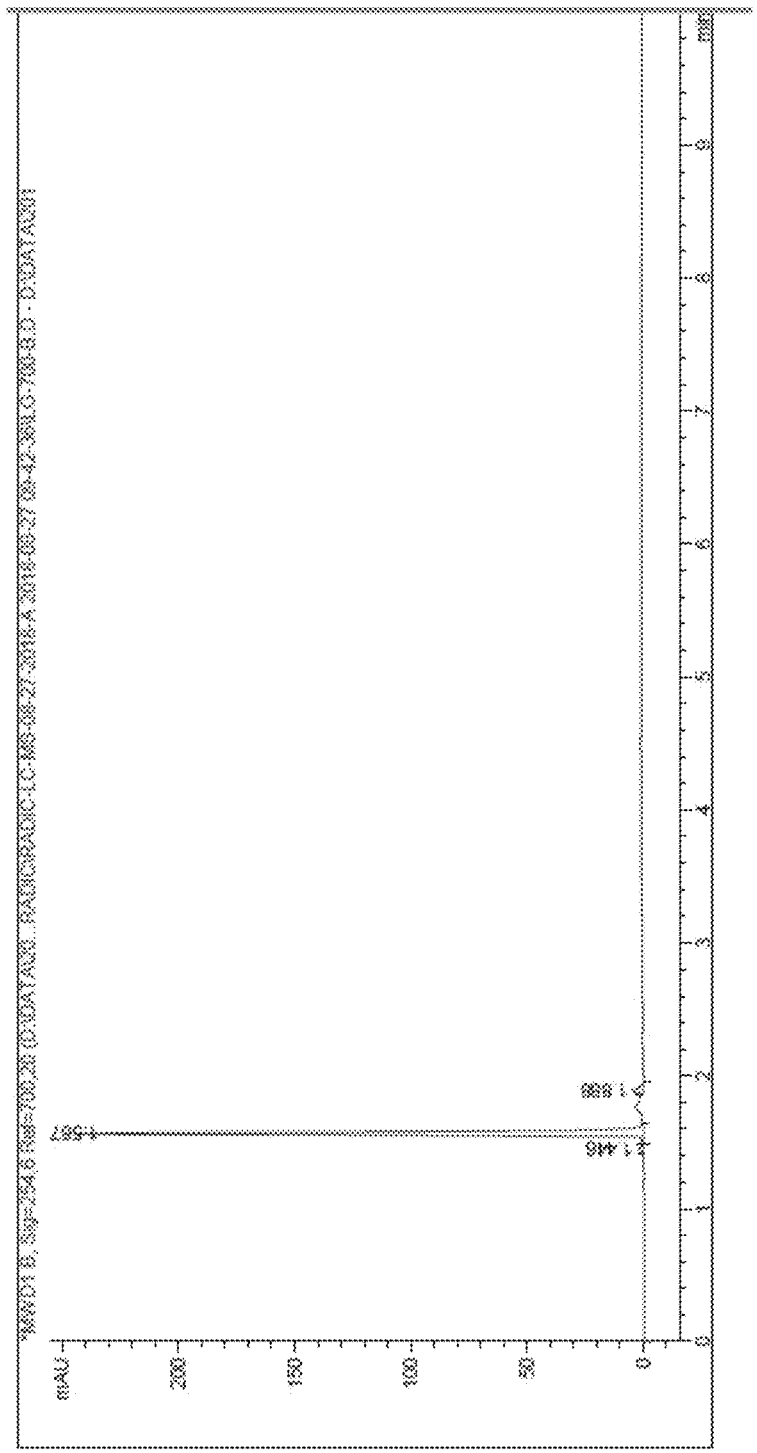
FIG. 25 illustrates a liquid chromatography-mass spectrometry (LC-MS) analysis of (2E)-2-(N-hydroxyimino)-N-[2-(4-{2-[(2E)-2-(N-hydroxyimino) acetamido]ethyl}piperazin-1-yl)ethyl]acetamide (LG-700) LC-MS purity as described in detail in Example 1, below.

(2E)-2-(N-hydroxyimino)-N-[2-(4-{2-[(2E)-2-(N-hydroxyimino)acetamido]ethyl}piperazin-1-yl)ethyl]acetamide (LG-700) LC-MS purity: See FIG. 25.

Figure 26:
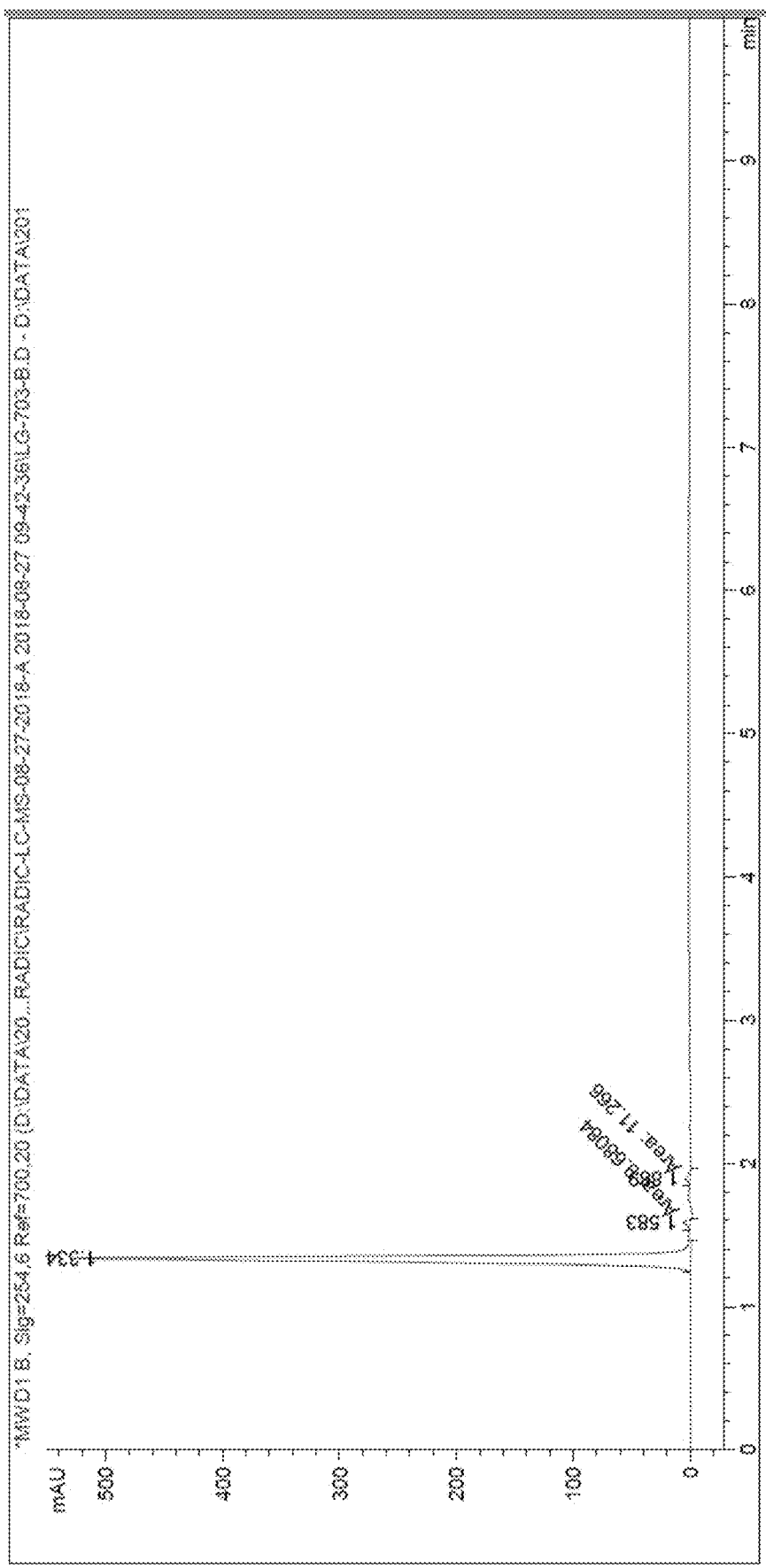
FIG. 26 illustrates an LC-MS analysis of (2E)-2-(N-hydroxyimino)-N-[2-(4-{2-[(2E)-2-(N-hydroxyimino)acetamido]ethyl}-1,4-diazepan-1-yl)ethyl]acetamide (LG-703) LC-MS purity: See FIG. 26.

(2E)-2-(N-hydroxyimino)-N-[2-(4-{2-[(2E)-2-(N-hydroxyimino)acetamido]ethyl}-1,4-diazepan-1-yl)ethyl]acetamide (LG-703) LC-MS purity: See FIG. 26.

Figure 27:
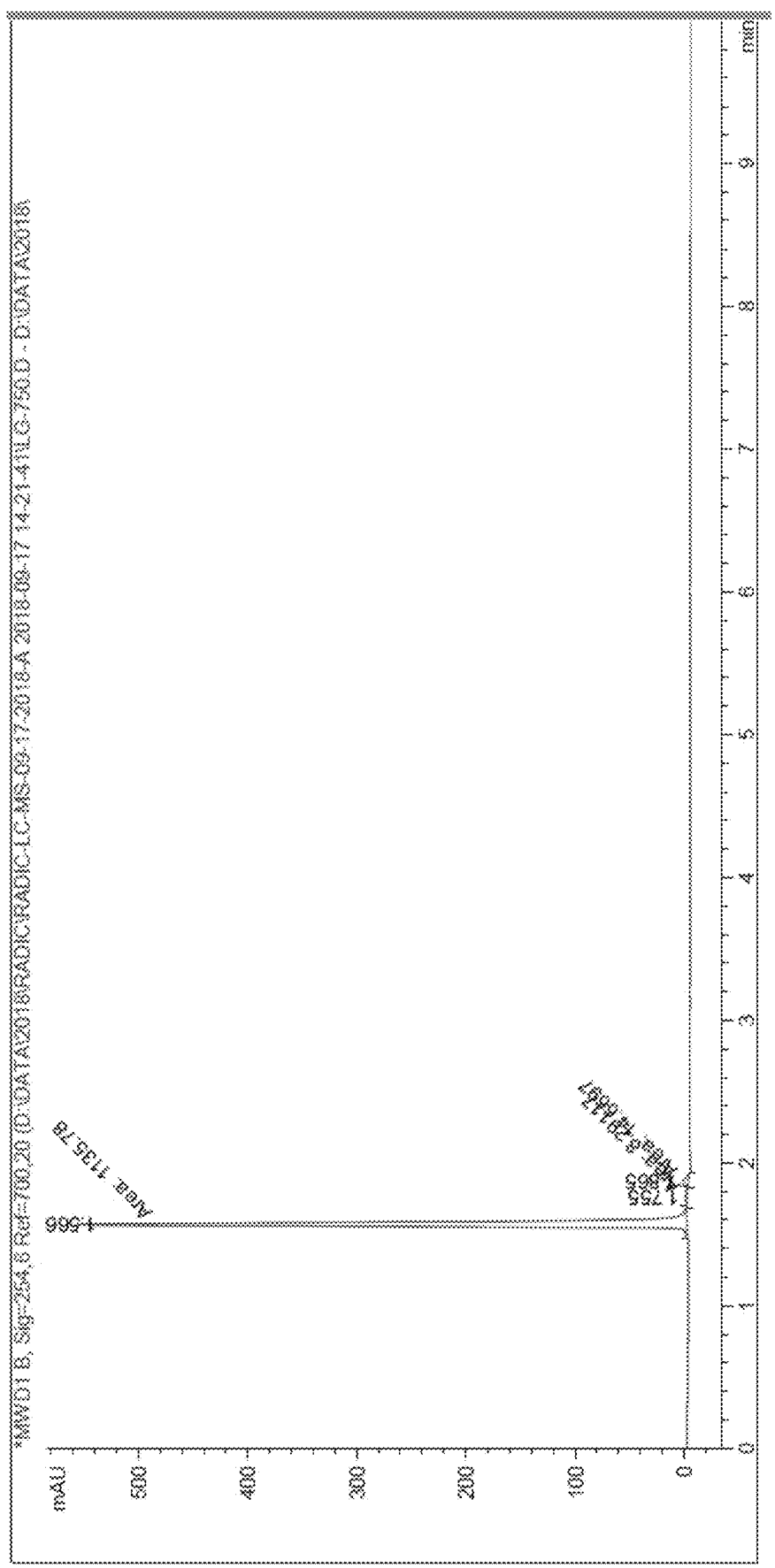
FIG. 27 illustrates an LC-MS analysis of (2E)-2-(N-hydroxyimino)-N-[3-(4-{2-[(2E)-2-(N-hydroxyimino)acetamido]ethyl}piperazin-1-yl)propyl]acetamide (LG-750) LC-MS purity as described in detail in Example 1, below.

(2E)-2-(N-hydroxyimino)-N-[3-(4-{2-[(2E)-2-(N-hydroxyimino)acetamido]ethyl}piperazin-1-yl)propyl]acetamide (LG-750) LC-MS purity: See FIG. 27.

Figure 28:
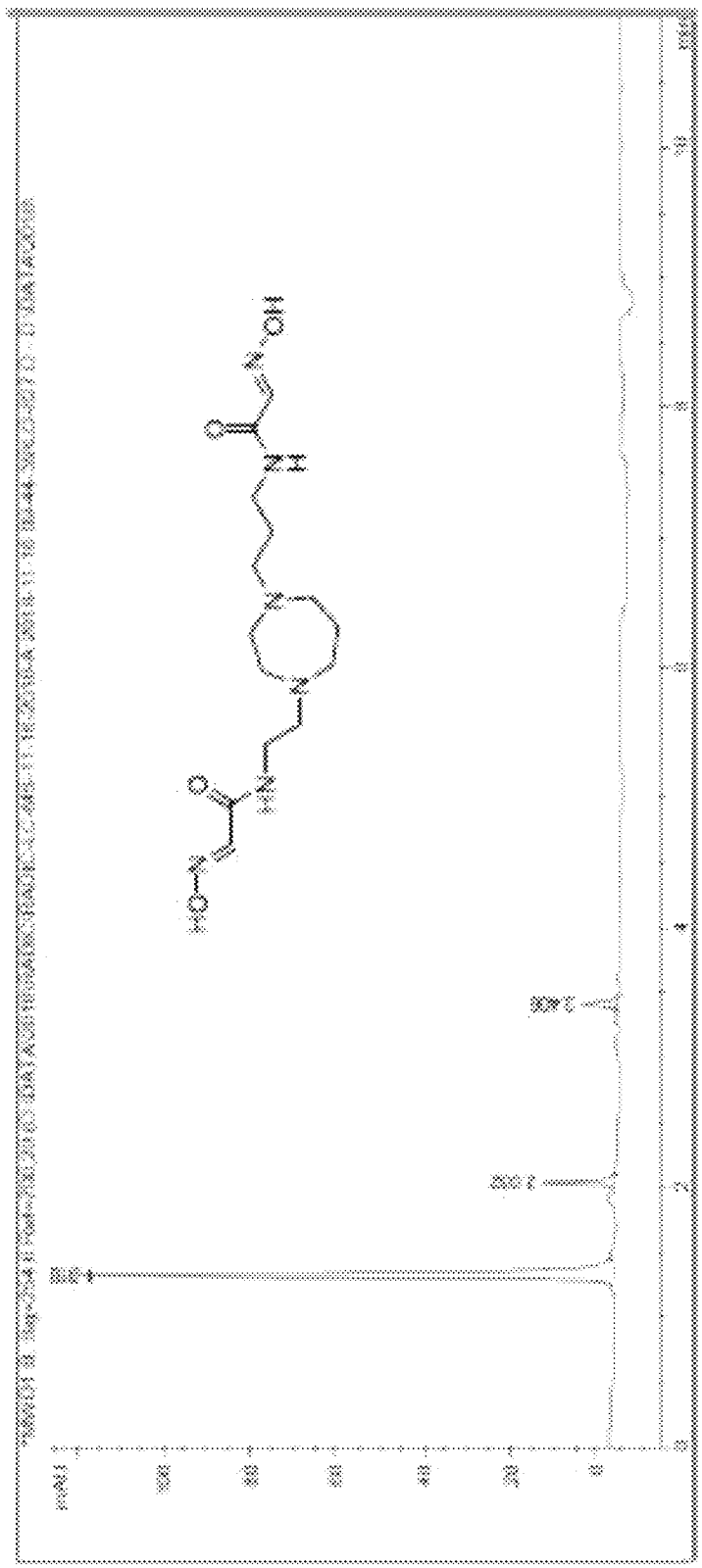
FIG. 28 illustrates an LC-MS analysis of (2E)-2-(N-hydroxyimino)-N-[3-(4-{2-[(2E)-2-(N-hydroxyimino)acetamido]ethyl}-1,4-diazepan-1-yl)propyl]acetamide (LG-838) LC-MS purity as described in detail in Example 1, below.

(2E)-2-(N-hydroxyimino)-N-[3-(4-{2-[(2E)-2-(N-hydroxyimino)acetamido]ethyl}-1,4-diazepan-1-yl)propyl]acetamide (LG-838) LC-MS purity: See FIG. 28.

Figure 29:
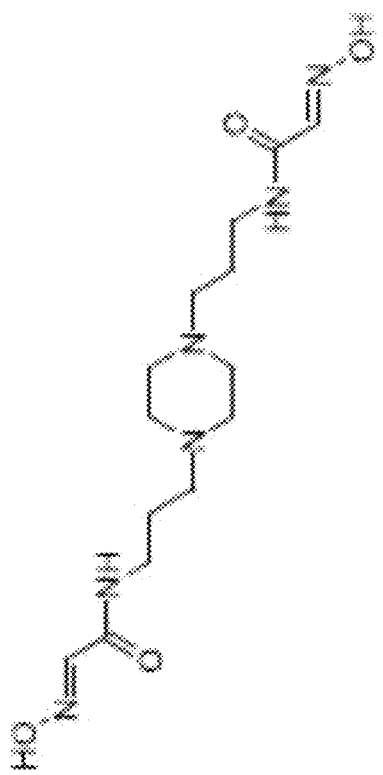
FIG. 29 illustrates an LC-MS analysis of (2E)-2-(N-hydroxyimino)-N-[3-(4-{3-[(2E)-2-(N-hydroxyimino)acetamido]propyl}piperazin-1-yl)propyl]acetamide (LG-747) LC-MS purity as described in detail in Example 1, below.

(2E)-2-(N-hydroxyimino)-N-[3-(4-{3-[(2E)-2-(N-hydroxyimino)acetamido]propyl}piperazin-1-yl)propyl]acetamide (LG-747) LC-MS purity: See FIG. 29.

Figure 30:
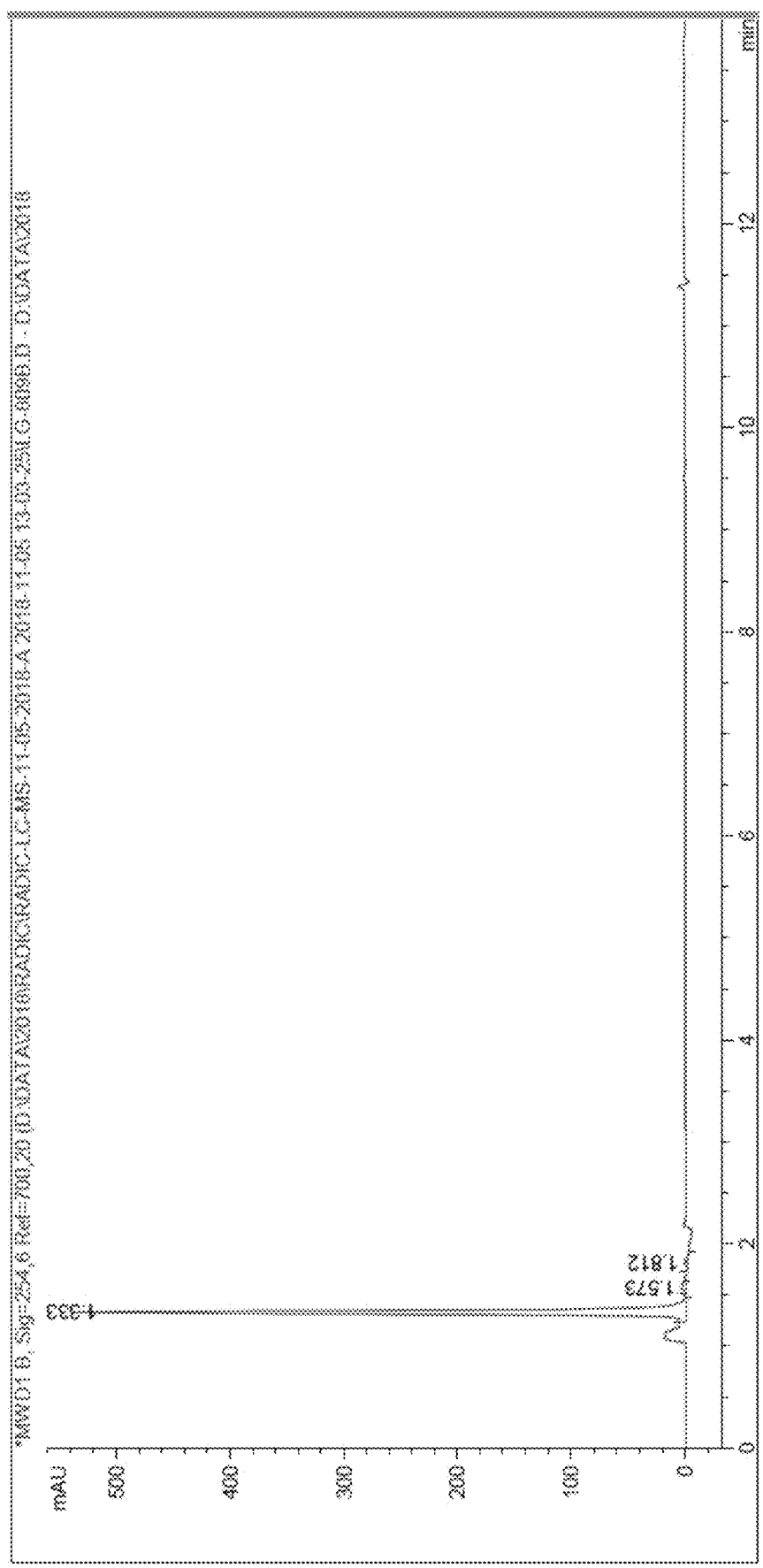
FIG. 30 illustrates an LC-MS analysis of (2E)-2-(N-hydroxyimino)-N-[3-(4-{3-[(2E)-2-(N-hydroxyimino)acetamido]propyl}-1,4-diazepan-1-yl)propyl]acetamide (LG-804) LC-MS purity as described in detail in Example 1, below.

(2E)-2-(N-hydroxyimino)-N-[3-(4-{3-[(2E)-2-(N-hydroxyimino)acetamido]propyl}-1,4-diazepan-1-yl)propyl]acetamide (LG-804) LC-MS purity: See FIG. 30.

Figure 31:
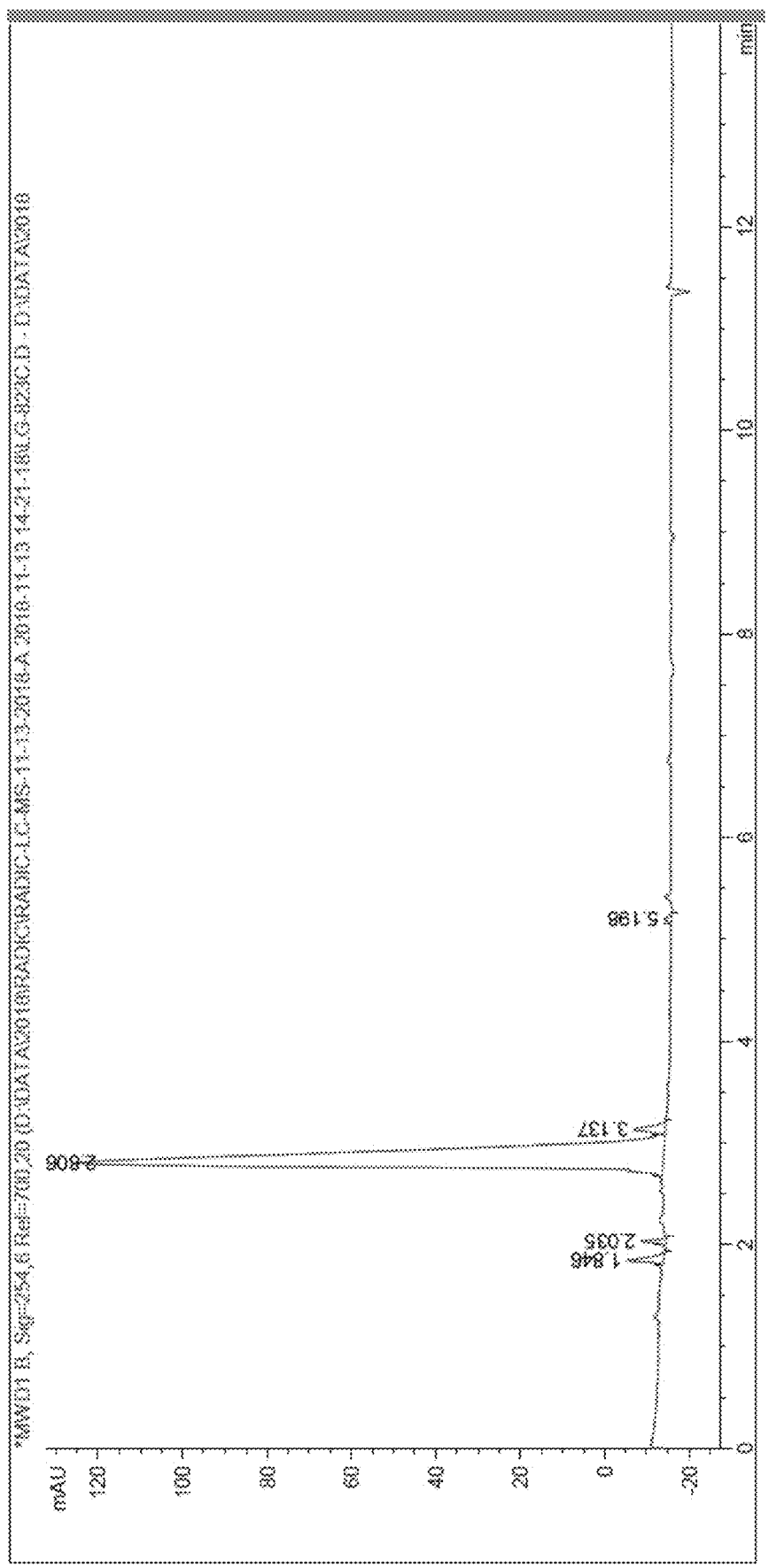
FIG. 31 illustrates an LC-MS analysis of (2E)-2-(N-hydroxyimino)-N-[2-(1-{2-[(2E)-2-(N-hydroxyimino)acetamido]ethyl}piperidin-4-yl)ethyl]acetamide (LG-823) LC-MS purity as described in detail in Example 1, below.

(2E)-2-(N-hydroxyimino)-N-[2-(1-{2-[(2E)-2-(N-hydroxyimino)acetamido]ethyl}piperidin-4-yl)ethyl]acetamide (LG-823) LC-MS purity: See FIG. 31.

Figure 32:
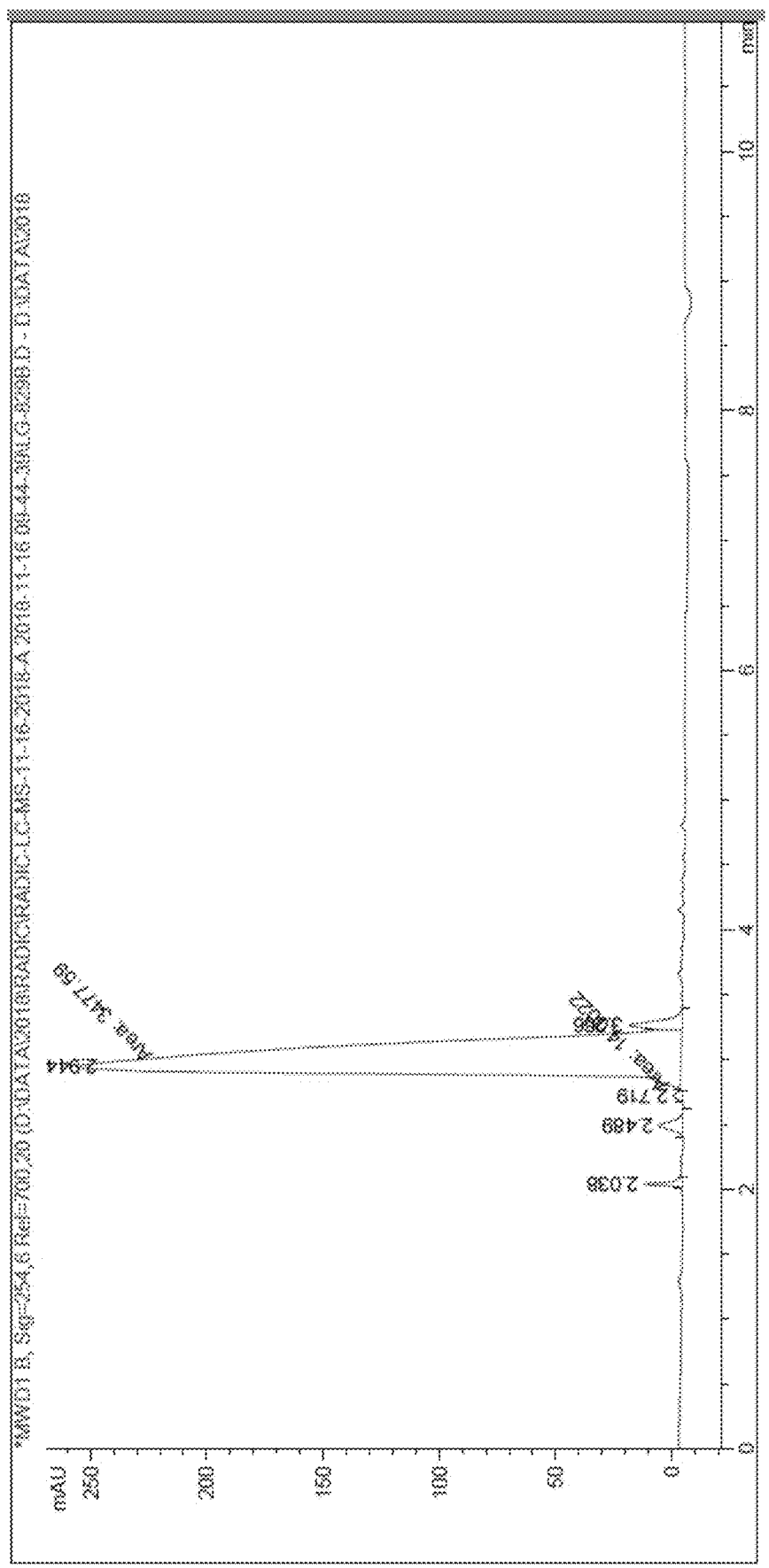
FIG. 32 illustrates an LC-MS analysis of (2E)-2-(N-hydroxyimino)-N-[3-(4-{2-[(2E)-2-(N-hydroxyimino)acetamido]ethyl}piperidin-1-yl)propyl]acetamide (LG-829) LC-MS purity as described in detail in Example 1, below.

(2E)-2-(N-hydroxyimino)-N-[3-(4-{2-[(2E)-2-(N-hydroxyimino)acetamido]ethyl}piperidin-1-yl)propyl]acetamide (LG-829) LC-MS purity: See FIG. 32.

Reactivation kinetics. Covalent conjugates of hAChE identical to those inhibited by nerve agent organophosphates (OPs) VX, sarin and cyclosarin were prepared using low toxicity, nonvolatile fluorescent methylphosphonate (Flu-MP) [13] analogues of nerve agents. The Flu-MPs differ from actual nerve agent OPs only by the structure of their respective leaving groups that are excluded from the resulting OP-hAChE structures. Inhibition of hAChE by Flu-MPs results in OP-hAChE covalent conjugates identical to the ones formed upon inhibition with the corresponding volatile OPs. Four to ten-fold stoichiometric excess of Flu-MPs or paraoxon was used to inhibit hAChE (approximately 20 uM) for several minutes at the room temperature resulting in greater than or equal to 99% loss of catalytic activity, to ensure homogeneous inhibition by the more potent $S_P$ enantiomer of Flu-MPs. Excess unreacted Flu-MP was removed from the inhibition mixture by Sephadex G-50 separation on two consecutive spin columns (BioRad). Time dependent recovery of hAChE activity was monitored spectrophotometrically [14] in 0.1M Phosphate buffer pH 7.4 (containing 0.01% BSA) upon addition of LG bis-oximes at 37° C. The first order reactivation rate constant ($k_{obs}$) for each oxime+OP-hAChE conjugate combination was calculated by nonlinear regression. The dependence of reactivation rates on oxime concentrations and determination of maximal reactivation rate constant $k_2$, Michaelis-Menten type constant $K_{ox}$, and the overall second order reactivation rate constant $k_r$ were conducted as previously described [12].

Results and Discussion

X-Ray Structures of RS194B in Complexes with Apo hAChE and VX-hAChE Conjugate

Figure 1A:
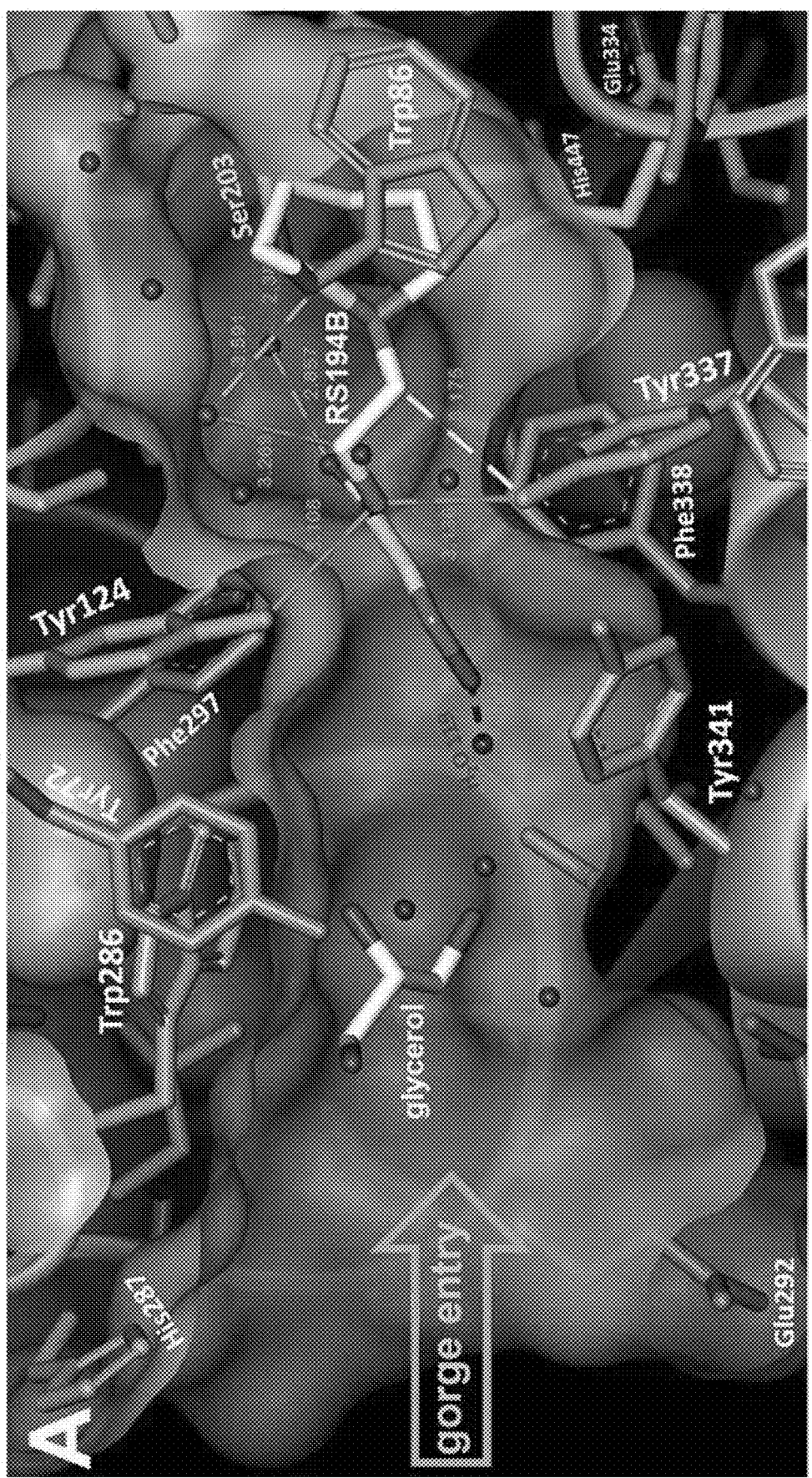
Figure 1B:
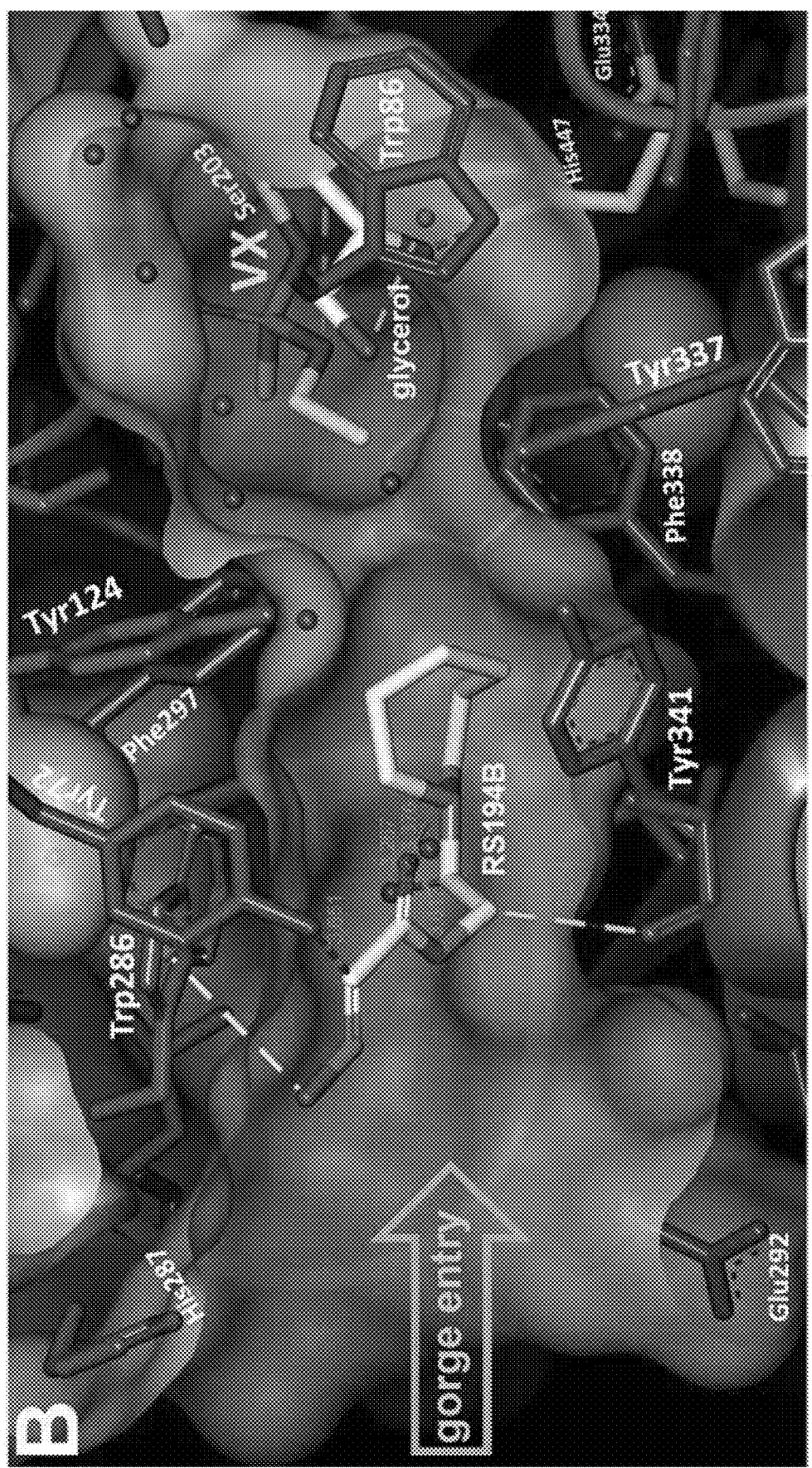

In order to develop structural template for design of accelerated uncharged antidotes of OP conjugated hAChE we have solved atomic structures of RS194B, one of most promising uncharged oxime reactivators [15], in complexes with native hAChE (FIG. 1A, C) and with VX-hAChE conjugate (FIG. 1B, D). Co-crystals of the binary RS194B*hAChE complex revealed molecule of RS194B bound to the choline binding site at the base of the hAChE active center gorge (FIG. 1A, C) that upon brief soak in VX analogue solution shifted upwards, above the "choke point" narrow defined by rings of Tyr124 and Tyr337, towards the peripheral site at the opening of the gorge (FIG. 1B, D). In both structures reactive oxime moiety of RS194B is pointing towards the gorge entry and away from the native or VX-conjugated active Ser203, its intended reactivation target. A molecule of glycerol, cryoprotectant used in flash-freezing of crystals, was found well defined in each of complexes but at different binding sites, alternating with RS194B between the choline binding site in the native hAChE and the peripheral site in the VX-hAChE conjugate (FIG. 1).

FIG. 1. X-ray structures of RS194B in complex with FIG. 1A) native hAChE and FIG. 1B) VX-hAChE conjugate. Connolly surfaces created using 1.4 Å sphere were partially removed to reveal interior of the active center gorge. Molecule of glycerol and selected, functionally important amino acid side-chains are represented as sticks and labelled, along with Glu334-His447-Ser203 catalytic triad. Stabilizing H-bonding is indicated by dashed lines in panels A and B. are from the P3$_1$ complex. $2F_O$-$F_C$ electron density maps (blue) contoured at 1σ level are given for each of the complexes in the lower panels, C and D.

Figure 1C:
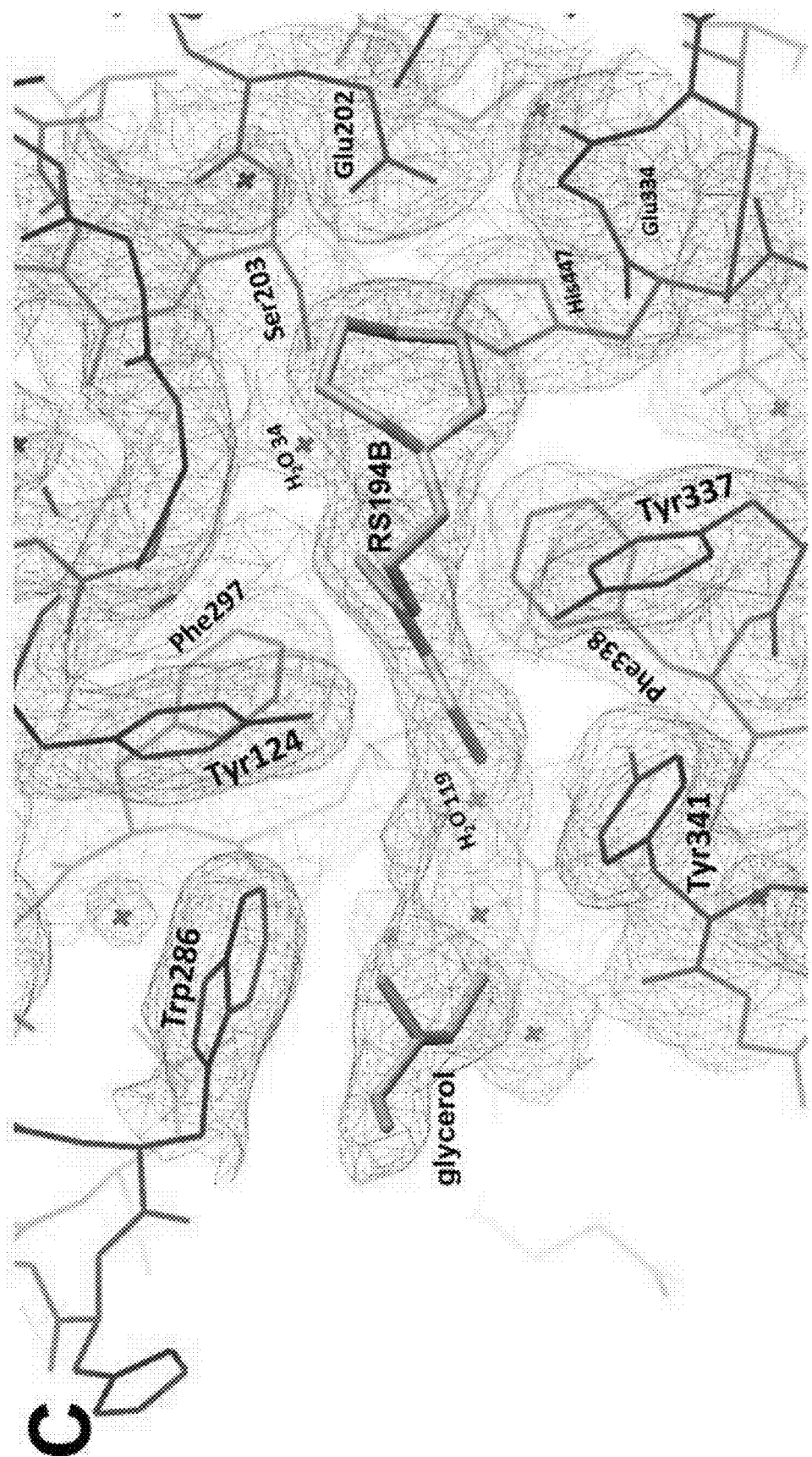
Figure 1D:
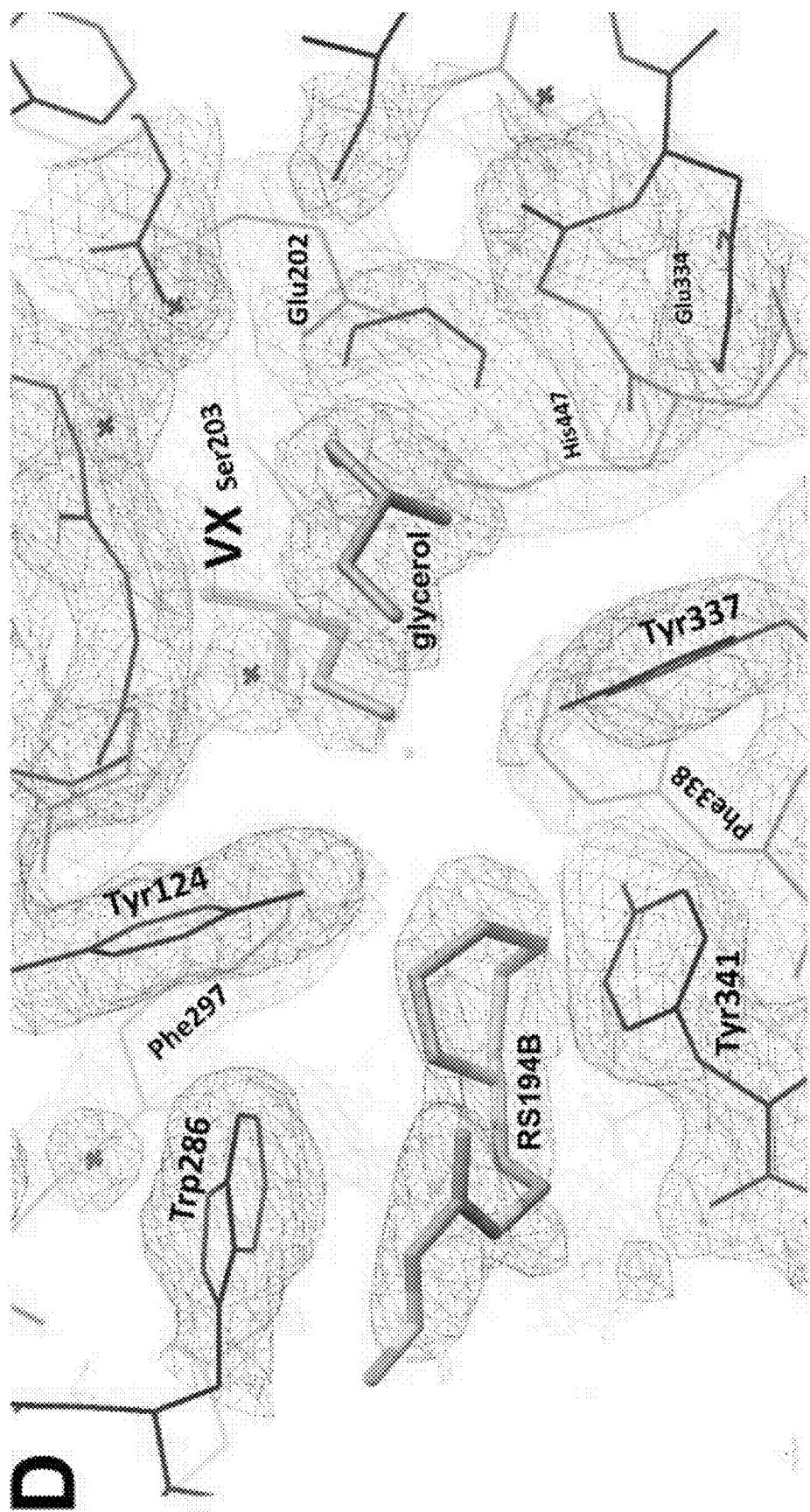

The molecule of RS194B appears well stabilized within the choline binding site of the native hAChE (FIG. 1A) by hydrophobic alkyl-π interactions between the azepine ring and 4.1 Å-4.5 Å distant aromatic indole of Trp 86 and in the "choke point" narrow by two 3.1 Å H-bonds between the amido nitrogen of RS194B and hydroxyls on tyrosines 337 and 124. In the VX-hAChE conjugate, however, RS194B is pushed upwards towards hAChE gorge entry where hydrophobic interaction between the azepine ring and 4.6 Å distant Tyr341 appears weaker and only one H-bond between 3.3 Å far backbone carbonyl of Tyr 341 and RS194B alkyl chain carbon can be identified. Some additional stabilization is provided by π-π interaction between acetamido-oxime conjugated double bonds and approximately 4 Å far indole of Trp 286. Overall weaker stabilization of RS194B at the peripheral site of the VX-hAChE is consistent with millimolar $K_{ox}$ value determined from the kinetics of VX-hAChE reactivation by RS194B [12] that are up to an order of magnitude higher than the $K_i$ constant of 157 uM determined for the reversible inhibition of hAChE by RS194B. Conformation of RS194B molecule in two structures was slightly different with acetamido-oxime "tail" being rotated by approximately 78 degree angle side-ways around the substituted azepine N—C single bond from its near symmetric, "curly" position in the Apo hAChE complex to the near in-plane more "extended" position with azepine ring of the VX-hAChE complex (FIG. 1B). In the "curly" conformation distance between carbonyl oxygen and hypothetic H+ of the protonated azepine ring nitrogen was nearly one Ångstrom smaller, and at just below 3 Å allowed for more efficient intramolecular H-bond stabilization. Also, positioning of the azepine N, centrally in apposition to the Trp86 indole ring and close (less than 6 Å) to the anionic Glu202 further suggests that the RS194B azepine bound to hAChE is in the protonated state. The RS194B molecule also hydrogen bonds with water molecules in the active center gorge of Apo hAChE. The carbonyl oxygen of the RS194B amide forms strong 2.86 Å H-bond with water molecule firmly stabilized in the hAChE oxyanion hole between Ser203 Oγ and Gly122 backbone N—H. The oximate oxygen, at the same time, is extending through the "choke point" narrow towards the gorge entry within a contiguous electron density that includes strongly (at 2.3 Å) H-bond associated water molecule HOH119, a part of the H-bonded networked molecules (HOH113, HOH23) that extend towards the bulk solvent (FIG. 1C). The HOH119 is also H-bonded to the peptide bond carbonyl of Phe295 (at 2.6 Å) suggesting that one of its hydrogens has to serve as a proton donor towards RS194B oximate oxygen. The close 2.3 Å vicinity of the oximate and HOH119 oxygen atoms and likely orientation of HOH119 proton towards oximate, that has to fit within that distance suggest that the RS194B oximate is bound in the dissociated, non-protonated state. In the case RS194B oximate was protonated the two protons would find themselves at the unlikely, less than 2 Å distance.

Overall structural information, thus, suggests that the RS194B molecule co-crystallizes with Apo hAChE as a zwitterion. Interactions of RS194B within the VX-hAChE conjugate, upon VX analogue soak, are less extensive and could not support similar conclusion.

In Silico Design and Screening of Uncharged Bis-Oxime Library

The non-productive orientation of the RS194B oximate group in X-ray structures of its both complexes, with apo hAChE and with VX-hAChE conjugate is opposite from the one expected for an effective nucleophilic reactivator of OP-hAChE conjugates. It may, however, be consistent with low affinity of RS194B for OP-hAChEs reflected in milli-molar $K_{ox}$ values obtained from reactivation kinetics [12]. One possible remedy to avoid non-productive binding orientation in reactivation is to introduce additional reactive oximate group on the opposite side of the central RS194B heterocycle.

Table 2, illustrated in FIG. 33, illustrates the in silico design and evaluation of uncharged bis-oximes by computational docking into the VX-hAChE X-ray structure. Each compound was docked in four different bis-oxime protonation states. Compounds are rank-ordered using an average score.

We have created in silico seventeen uncharged heterocyclic bis-oximes (Table 2, FIG. 33). Both six and seven membered central heterocycles were considered to create homopiperazine, piperazine and piperidine bis-oximes. For the in silico bis-oxime evaluation, molecule of RS194B was replaced in the VX-hAChE conjugate X-ray structure with each of bis-oximes and computationally docked with its oxime groups adjusted to either doubly-, singly- or non-protonated oxime group configuration. Composite docking scores were used for rank-ordering by combining resulting distances between the closer oximate and conjugated phosphorus, the oxime attack angle and an overall bis-oxime compound stabilization energy. Homopiperazine compound #5 symmetrically substituted with acetamido alkyl chains of the same size as those in RS194B scored best in the docking analysis (Table 2), practically irrespectively of the ionization state of two oxime groups. This compound was chosen as a lead for chemical synthesis and further in vitro evaluation.

Chemical Synthesis of Uncharged Bis-Oxime Library

Starting with compound #5 (Table 2) as a lead we synthesized seven novel uncharged bis-oximes by N-alkylation of central homopiperazine, piperazine or piperidine heterocycles (see Table 3, illustrated in FIG. 34). Detailed synthetic procedures and structural characterization are discussed above.

Table 3, illustrated in FIG. 34: Synthesized library of uncharged bis-oximes based on homopiperazine (LG-703, LG-804), piperazine (LG-700, LG-750, LG-747) and piperidine (LG-823, LG-829) central heterocycles. Values of $pK_a$, $logD_{7.4}$ and $logP_{neutral}$ constants were obtained by solid state potentiometric titration. Synthesis of between 20 mg and 150 mg quantities of pure material allowed initial characterization of ionization states (pKa values) for each compound using solid state potentiometric titration. The evaluated individual pKa values for each of oxime groups and protonated heterocyclic nitrogens could be used to predict elements of their physiological antidotal efficacy. The lowest determined pKa value, for example, should reflect nucleophilicity of the most reactive oximate. The closer those values are to physiological pH of 7.4 the larger fraction of the reactivator should be in dissociated, reactive state and one could predict that compound will be more effective antidote under physiological conditions. Using that criterion all of novel bis-oximes should have larger fraction of reactive dissociated form of their nucleophiles and be better reactivators than RS194B since all of their "Base pKa" values are lower than pKa of 8.66 determined for RS194B. FIG. 34 shows experimentally determined acidity ($pK_a$); distribution coefficient ($logD_{7.4}$) and partition coefficient ($logP_{neutral}$) between water and n-octanol were obtained via potentiometric titrations (SiriusT3, Pion, Inc.); calculated values (in italics) including topological polar surface area (TPSA in Å$^2$) and number of hydrogen bond donors (HBD) were determined using MarvinView 5.4.1.2 (ChemAxon Ltd). The CNS MPO analysis was conducted as described by Wager et al., *ACS Chem Neurosci.* 2010,1:435.

With four ionizable groups (LG-823 and LG-829 have only three) each of novel bis-oximes can equilibrate between sixteen ionization states with total net charge of −2, −1, 0, +1 and +2. The −1, 0 and +1 will be most likely states at around pH 7.4. Ideally, all three states should be significantly represented for an effective in vivo reactivator in a variety of tissues, as observed (see FIG. 40A-B). Protonated and zwitterionic state will be important for effective binding interaction with OP-hAChE, a molecular environment that prefers cationic ligands, as well as nucleophilic reactivity. As pH of the environment rises ionizable groups with lower pKa values will protonate and loose negative charge followed by addition of protons and positive charge to the groups with higher pKa values. Somewhere between the central two pKa values compound will have all negative oximates protonated and thus uncharged before heterocyclic nitrogens start to protonate (see FIG. 40A). The wider and closer that pH interval to physiological pH the higher fraction of the bis-oxime will be uncharged and able to diffuse through biological membranes, including the blood-brain-barrier (BBB). The pKa values from the Table 3 suggest that five of seven bis-oximes should be uncharged in a wider pH interval, closer to pH 7.4 compared to RS194B. In other words, fraction of uncharged species for those bis-oximes at pH 7.4 should be larger than for RS194B (see FIG. 40A) allowing them to diffuse faster and to larger extent through biological membranes rendering them both more centrally active and more bioavailable than RS194B.

In Vitro Efficacy of Novel Bis-Oximes for Reactivation of OP-Hache Conjugates

More than half of novel bis-oximes showed superior in vitro reactivation kinetics when compared to monoxime RS194B. We studied dependence of reaction rates on oxime concentrations in reactivation of inhibited OP-hAChEs (see FIG. 35). The studied conjugates accurately resembled structures of hAChE inhibited by nerve agents sarin, cyclosarin (CS) or VX (FIG. 1B).

FIG. 35 graphically illustrates data presented in FIG. 38, showing in vitro reactivation kinetics of four OP-hAChE conjugates by seven exemplary uncharged LG bisoximes compared to the monoxime RS194B (dashed curves). Dependence of the first order reactivation rate constant ($k_{obs}$) on oxime concentration. The larger $k_{obs}$ values indicate more efficient reactivation. All reactions were done in 0.1M Phosphate buffer pH 7.4 at 37° C.

The most efficient reactivators for all four OP conjugates appeared to be two piperidine bis-oximes, LG-829 and one methylene group shorter LG-823, followed by homopiperazine LG-804. The two piperazines LG-747 and LG-700 were generally similar to RS194B or slower. Nevertheless LG-747 showed important enhancement of VX-hAChE reactivation rate at the lowest 100 uM concentration over several other bis-oximes and over RS194B. This is significant since 100 uM is closest to the expected bis-oxime concentration in tissue upon therapeutic administration of an antidote in vivo [12]. We expect to see similar effect of LG-747 for reactivation of other OP-hAChE conjugates, as well.

Overall, the initial in vitro analysis reveals that all seven bis-oximes are promising antidotes for ex vivo and in vivo settings, including—in order of their in vivo potency: LG-829 greater than LG-823 greater than LG-804 greater than LG-703 greater than RS194B greater than LG-750 greater than LG-747 greater than LG-700.

X-Ray Structure of Bis-Oxime LG-703 in Complex with Apo hAChE

The enhanced in vitro reactivation efficacy of uncharged bis-oximes compared to the monoxime RS194B is raising a question on whether the enhancement indeed came as a consequence of improved, productive orientation of the second oxime group as opposed to the one found in RS194B complexes with Apo hAChE and VX-hAChE conjugate. To address that issue we solved X-ray structure of the Apo hAChE in complex with LG-703, a bis-oxime structurally closest to RS194B where the additional acetamido alkyl change was substituted into central seven membered heterocyclic homopiperazine core (Table 3). As expected, while one of the oxime groups was pointing outwards from the active center gorge opening, similar to the RS194B monoxime (FIG. 3A,B), the additional oxime assumed productive orientation extending into the active center gorge interior close to the active Ser203 (FIG. 36).

FIG. 36A: X-ray structure of LG-703 in complex with native hAChE.

FIG. 36B: overlay with RS194B from the VX-hAChE*RS194B complex. Connolly surfaces were partially removed to reveal interior of the active center gorge. Selected amino acid side-chains are represented as sticks, along with Glu334-His447-Ser203 catalytic triad. Stabilizing H-bonding is indicated by dashed lines in panel A.

FIG. 36C: $2F_O$-$F_C$ electron density map (blue) contoured at 1σ level.

The main stabilizing interaction of bound LG-703 comes from the alkyl-π interaction between its homopiperazine ring and Tyr341 including an additional H-bond with Tyr124. This is similar to RS194B binding to the VX-hAChE complex (FIG. 1B). Also, the amido nitrogen of the extended, internally bound acetamido substituent forms hydrogen bond with $H_2O$ 2, well stabilized within the active center oxyanion hole (FIG. 3A). Although the central heterocycle in LG-703 is substituted symmetrically conformations of two identical substituents differ significantly. The outside-pointing substituent is curled and allows for the internal H-bond formation between its amide carbonyl and hypothetically protonated ring nitrogen. The hAChE gorge stabilized substituent, is however fully extended, pointing to the choline binding site, nearly equidistantly between the Ser203 and Trp86. This reactive, oxime-bearing arm would have capacity to nucleophilically attack OPs conjugated to the Ser203. In this structure, however the oximate oxygen of LG-703 appears at 3.2 Å distance from the fully dissociated Glu202 carboxylate suggesting that it is bound in the protonated state forming a strong hydrogen bond with Glu202. This interaction also points to the potential role that Glu202, alongside nearby His447 could play in enhancing nucleophylicity of the incoming LG-703 oxime group for faster reactivation in the OP conjugated hAChE.

Overall, the X-ray structure of the LG-703*hAChE complex not only confirmed validity of our initial strategy to improve productive orientation of the uncharged azepine acetamidoxime RS194B. It also revealed Glu202 and His447 as contributing amino acids in potentiation of nucleophilicity for the attacking LG oxime resulting in accelerated reactivation in OP intoxication.

Conclusion

In this study we demonstrated successful design, synthesis and initial in vitro functional characterization of a small directed library of seven novel uncharged bis-oximes. Starting with X-ray structural analysis of the prototype uncharged acetamido monoxime RS194B we revealed as dominant suboptimal, nonproductive orientations of RS194B molecule when bound to either, native or VX-inhibited hAChEs. Using simple rationale that its reactivation efficacy should be improved upon introduction of an additional reactive oxime group we created a small library of seventeen bis-oximes built on six- or seven-ring saturated heterocycles. The in silico analysis guided us to select and synthesize in 20 mg to 150 mg quantities seven novel compounds, two piperidines, three piperazines and two homopiperazines doubly substituted with alkyl acetamido oximes. Four of the seven novel bis-oximes were faster in vitro reactivators of sarin, VX, cyclosarin and paraoxon derived OP-hAChE conjugates, compared to the monoxime RS194B. By solving X-ray structure of one of improved bisoximes, LG-703, in complex with hAChE we were able to confirm that improved reactivation efficacy was consistent with productive orientation of one of the two nucleophilically reactive oxime groups of LG-703.

This library of bis-oximes represents a promising starting point for advanced, ex vivo and in vivo testing as efficacious yet uncharged reactivator antidotes against OP intoxication. Preliminary testing in mice showed low toxicity $LD_{50}$ greater than (>) 200 mg/kg (i.m., or intramuscular) for two of the bis-oximes (LG-703 and LG-829), less toxic than 2PAM (106 mg/kg) and approaching low toxicity of RS194B (approximately 400 mg/kg).

References

[1] Schumacher, M., et al. Primary structure of *Torpedo californica* acetylcholinesterase deduced from its cDNA sequence. *Nature.* 319 (1986) 407-409.

[2] Sussman, J. L., et al. Atomic structure of acetylcholinesterase from *Torpedo californica*: a prototypic acetylcholine-binding protein. *Science.* 253 (1991) 872-879.

[3] Kryger, G. I., et al. Structure of acetylcholinesterase complexed with E2020 (Aricept): implications for the design of new anti-Alzheimer drugs. Structure. 7 (1999) 297-307.

[4] Dym, O., et al. The impact of crystallization conditions on structure-based drug design: A case study on the methylene blue/acetylcholinesterase complex. *Protein Sci.* 25 (2016) 1096-1114.

[5] Cochran, R., et al. Oxime-assisted acetylcholinesterase catalytic scavengers of organophosphates that resist aging. *J Biol Chem.* 286 (2011) 29718-29724.

[6] Minor, W., et al. HKL-3000: the integration of data reduction and structure solution from diffraction images to an initial model in minutes. *Acta Crystallogr. D* 2006, 62, 859-866.

[7] Collaborative, C. P. The CCP4 suite: programs for protein crystallography. *Acta crystallogr. D* 1994, 50, 760-763.

[8] Cheung, J., et al. Structures of human acetylcholinesterase in complex with pharmacologically important ligands. *J. Med. Chem.* 2012, 55, 10282-10286.

[9] Adams, P. D., et al, PHENIX: a comprehensive Python-based system for macromolecular structure solution. *Acta Crystallogr. D* 2010, 66, 213-221.

[10] Davis, I. W., et al. MolProbity: all-atom contacts and structure validation for proteins and nucleic acids. *Nucleic acids res.* 2007, 35, W375-W383.

[11] Emsley, P., et al. Features and development of Coot. *Acta Crystallogr. D* 2010, 66, 486-501.

[12] Radio Z, et al.: Refinement of structural leads for centrally acting oxime reactivators of phosphylated cholinesterases. *J Biol Chem* 287(2012) 11798-11809.

[13] Amitai G, et al. Characterization of asymmetric fluorogenic phosphonates as probes for developing organophosphorus hydrolases with broader stereoselectivity. *Chem. Biol. Interact.* 175(2008) 249-254.

[14] Ellman G L, et al: A new and rapid colorimetric determination of acetylcholinesterase activity. *Biochem Pharmacol.* 7 (1961) 88-95.

[15] Rosenberg Y J, et al. Post-exposure treatment with the oxime RS194B rapidly reverses early and advanced symptoms in macaques exposed to sarin vapor. *Chem. Biol. Interact.* 274 (2017) 50-57.

A number of embodiments as provided herein have been described. Nevertheless, it can be understood that various modifications may be made without departing from the spirit and scope of the invention. Accordingly, other embodiments are within the scope of the following claims.

What is claimed is:

1. A compound having one of the following structures or compositions having one or more compounds of the following structures, optical isomer or a stereoisomer thereof, a racemate or racemic mixture thereof, an enantiomer, an individual diastereomer or a diastereomeric mixture thereof, or a crystalline product, or a pharmaceutically acceptable salt thereof, or prodrug thereof; or a composition comprising:

(a) a compound having the formula:

(i)

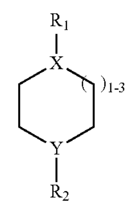

wherein X and Y are independently selected from C and N, and wherein $R_1$ and $R_2$ are independently selected from:

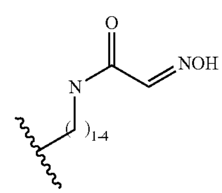

or

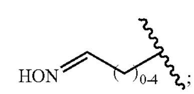

;

(ii)

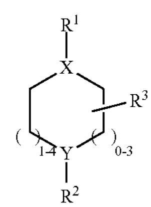

wherein X and Y are independently selected from C and N, wherein $R_1$ and $R_2$ are independently selected from:

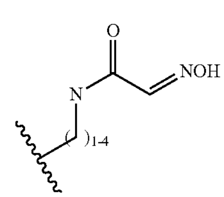

or

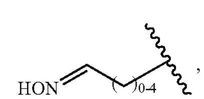

, and $R_3$ is independent selected from:
an alkyl, an alkenyl, an alkynyl, an alkyloxy, an alkylamino, an alkylthio, a cycloalkyl, a heterocycloalkyl, a phenyl, a heteroaryl, an acyl, a sulfonyl, a lactam, a sultam, a cyano, a hydroxy and a halogen; or (iii)

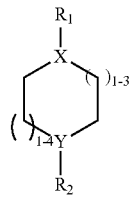

wherein X and Y are independently selected from C and N, and wherein $R_1$ and $R_2$ are independently selected from:

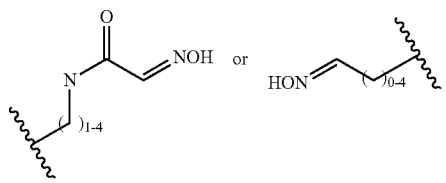

Provide that when X and Y are both N in formulas (i), (ii), and (iii), then $R_1$ and $R_2$ are independently selected from:

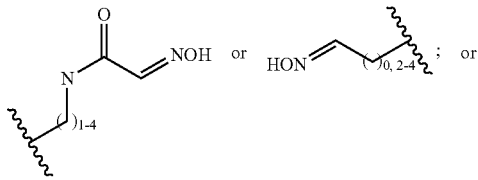

(b) a compound having the formula:

(i)

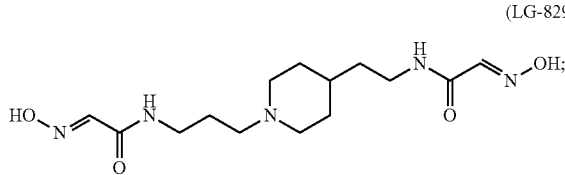
(LG-829)

(ii) a compound having the formula:

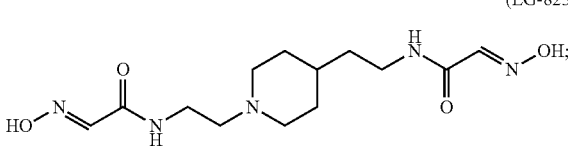
(LG-823)

(iii) a compound having the formula:

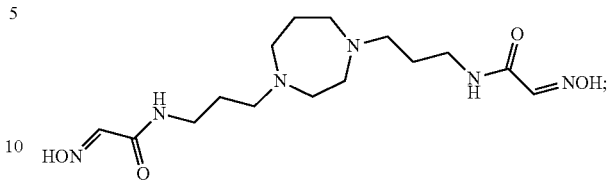
(LG-804)

(iv) a compound having the formula:

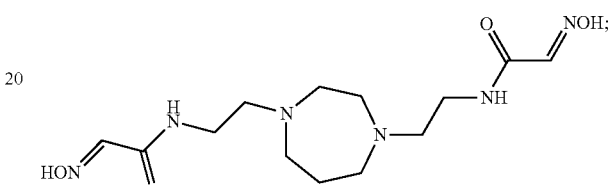
(LG-703)

(v) a compound having the formula:

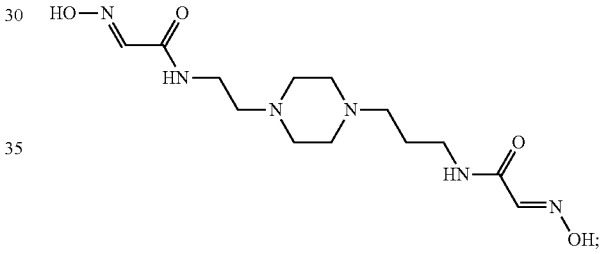
(LG-750)

(vi) a compound having the formula: or

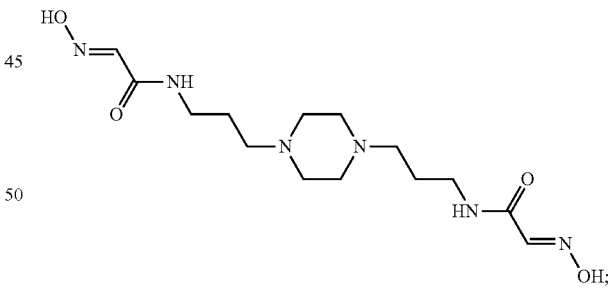
(LG-747)

or
(vii) a compound having the formula:

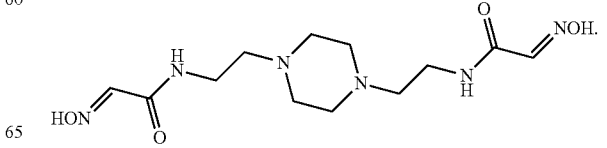
(LG-700)

2. A formulation or pharmaceutical composition comprising a compound or composition as set forth in claim 1, wherein optionally the formulation further comprises a pharmaceutically acceptable excipient, and optionally the pharmaceutically acceptable excipient comprises a sterile saline, a sterile buffer and/or a sterile water.

3. The formulation or pharmaceutical composition of claim 2, wherein formulation or the pharmaceutical composition is formulated for enteral or parenteral administration.

4. The formulation or pharmaceutical composition of claim 2, wherein the formulation or pharmaceutical composition is formulated for administration orally, parenterally, by inhalation spray or mist, nasally, topically, intrathecally, intrathecally, intracerebrally, epidurally, intracranially or rectally, or the formulation is a solid, liquid, aerosol, mist, powder or emulsion formulation.

5. The formulation or pharmaceutical composition of claim 1, formulated as or in or on: a liquid, a powder, an emulsion, a lyophilized powder, a spray, a cream, a lotion, a controlled release formulation, a tablet, a pill, a capsule, a gel, a geltab, a patch, an implants, an applicator stick, a solutions, a suspension, an ointment, a paste, a jelly, a paint, a powder, a mists an aerosol, an elixirs, a syrup, a liposome, a nanoliposome, a nanoparticle or a particle.

6. A product of manufacture comprising: a compound as set forth in claim 1.

7. The product of manufacture of claim 6, fabricated or manufactured as a pump, a device, a subcutaneous infusion device, a continuous subcutaneous infusion device, an infusion pen, a needle, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector, comprising: a compound as set forth in claim 1.

8. The product of manufacture of claim 6, fabricated or manufactured as a nebulizer or an inhaler comprising: a compound as set forth in claim 1.

9. A method for treating an organophosphate toxicity or poisoning or toxic exposure, or for treating organophosphate inhibition of an acetylcholinesterase (AChE), comprising:
administering to a patient or an individual in need thereof, a compound as set forth in claim 1, wherein optionally the compound or formulation is administered enterally or parenterally,
wherein optionally the compound or formulation is administered orally, parenterally, by inhalation spray, nasally, topically, intrathecally, intrathecally, intracerebrally, epidurally, intracranially or rectally, or
administering the compound as set forth in claim 1, using a pump, a device, a subcutaneous infusion device, a continuous subcutaneous infusion device, an infusion pen, a needles, a reservoir, an ampoules, a vial, a syringe, a cartridge, a disposable pen or jet injector, a prefilled pen or a syringe or a cartridge, a cartridge or a disposable pen or jet injector, a two chambered or multi-chambered pump, a syringe, a cartridge or a pen or a jet injector.

10. The method of claim 9, wherein the organophosphate toxicity, poisoning or toxic exposure is caused by exposure of the patient or individual to an alkyl methylphosphonate or related nerve agent, or an alkylphosphorate insecticide,
and optionally the organophosphate (OP) is or is a component of a toxin, an herbicide, an insecticide, or a nerve gas or nerve agent,
and optionally the organophosphate (OP) is or comprises a parathion, a malathion, a methyl parathion, a chlorpyrifos, a diazinon, a dichlorvos, a phosmet, a fenitrothion, a tetrachlorvinphos, an azamethiphos or an azinphos methyl, or the nerve agent is a soman (O-Pinacolyl methylphosphonofluoridate), a tabun (Ethyl N,N Dimethyl-phosphoramido-cyanidate) or a sarin ((RS)-propan-2-yl methylphosphonofluoridate).

11. The method of claim 9, wherein the acetylcholinesterase (AChE) is in the central nerve system (CNS), or the acetylcholinesterase (AChE) is a human acetylcholinesterase (hAChE).

12. A method for treating excessive acetylcholine stimulation in the brain, comprising: administering to a patient or an individual in need thereof, a compound as set forth in claim 1.

13. The method of claim 12, wherein the excessive acetylcholine stimulation in the brain, the CNS or the PNS is caused by a drug, a drug overdose, or a poisoning or a toxic exposure to a drug, and optionally the drug, drug overdose or poisoning causing the excessive acetylcholine stimulation is caused at least in part by a carbamate (wherein optionally the carbamate is or comprises physostigmine or eserine, neostigmine, pyridostigmine, carbaryl, carbaril or 1-naphthyl methylcarbamate; or, an organophosphate agent such as a pesticide or poison (wherein optionally the organophosphate agent is or comprises diisopropyl-fluorophosphate (DFP) or isoflurophate, and/or echothiophate.

14. The method of claim 12, wherein the compound or formulation is administered enterally or parenterally.

15. The method of claim 12, wherein the compound or formulation is administered orally, parenterally, by inhalation spray or mist, nasally, topically, intrathecally, intrathecally, intracerebrally, epidurally, intracranially or rectally.

16. The compound or composition of claim 1, having the formula:

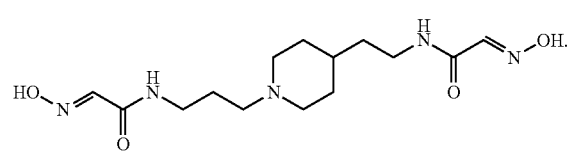

(LG-829)

17. The compound or composition of claim 1, having the formula:
(LG-823)
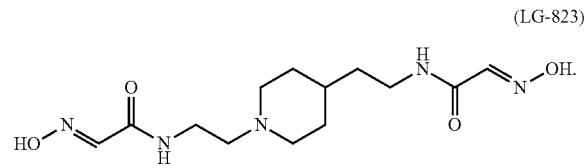 [SMILES: O=C(/C=N/O)NCCC1CCN(CCNC(=O)/C=N/O)CC1]
18. The compound or composition of claim 1, having the formula:
(LG-804)
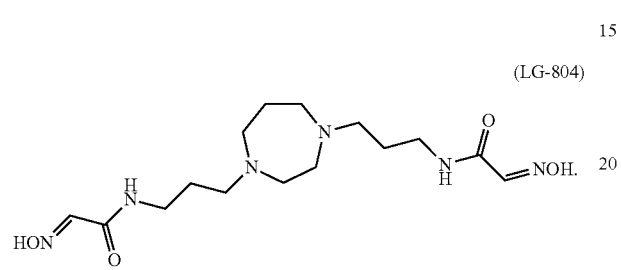
19. The compound or composition of claim 1, having the formula:
(LG-703)
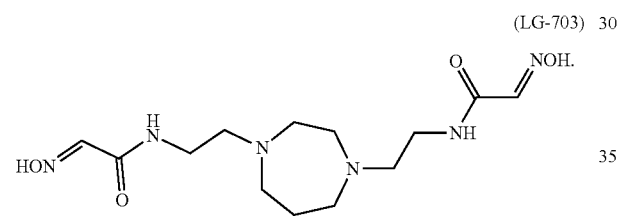
20. The compound or composition of claim 1, having the formula:
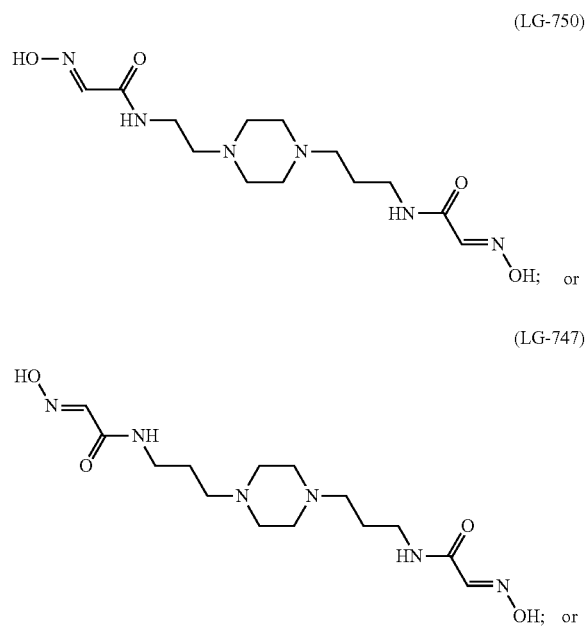
* * * * *